US012765940B2

(12) United States Patent
Wright et al.

(10) Patent No.: US 12,765,940 B2
(45) Date of Patent: Oct. 20, 2026

(54) SYSTEMS FOR RADIOFREQUENCY NEUROTOMY

(71) Applicant: Stratus Medical, LLC, Magnolia, TX (US)

(72) Inventors: Robert E. Wright, Clayton (AU); Scott A. Brandt, Denver, CO (US)

(73) Assignee: Stratus Medical, LLC, Magnolia, TX (US)

( * ) Notice: Subject to any disclaimer, the term of this patent is extended or adjusted under 35 U.S.C. 154(b) by 0 days.

(21) Appl. No.: 18/378,138

(22) Filed: Oct. 9, 2023

(65) Prior Publication Data

US 2024/0032990 A1 Feb. 1, 2024

Related U.S. Application Data

(63) Continuation of application No. 17/126,675, filed on Dec. 18, 2020, now Pat. No. 11,806,070, which is a (Continued)

(51) Int. Cl.
*A61B 18/14* (2006.01)
*A61B 18/12* (2006.01)
(Continued)

(52) U.S. Cl.
CPC ...... *A61B 18/1477* (2013.01); *A61B 18/1206* (2013.01); *A61B 2018/00434* (2013.01); (Continued)

(58) Field of Classification Search
CPC .. A61B 2018/0044; A61B 2018/00577; A61B 2018/1253; A61B 2018/1467; A61B 18/1477
See application file for complete search history.

(56) References Cited

U.S. PATENT DOCUMENTS 4,011,872 A 3/1977 Kamiya
4,206,761 A 6/1980 Cosman
(Continued)

FOREIGN PATENT DOCUMENTS

AU 2010314930 B2 10/2013
AU 2011256709 B2 10/2013
(Continued)

OTHER PUBLICATIONS

Amendment and Response to Office Action Dated Mar. 6, 2014, U.S. Appl. No. 13/101,009 (Jun. 3, 2014).
(Continued)

*Primary Examiner* — Eun Hwa Kim
(74) *Attorney, Agent, or Firm* — Laurence & Phillips IP Law

(57) ABSTRACT

Methods and systems for spinal radio frequency neurotomy. Systems include needles capable of applying RF energy to target volumes within a patient. Such target volumes may contain target medial branch nerves along vertebrae or rami proximate the sacrum. Such procedures may be used to ablate or cauterize a portion of the targeted nerve, thus blocking the ability of the nerve to transmit signals to the central nervous system. Disclosed needles may be operable to asymmetrically, relative to a central longitudinal axis of the needle, apply RF energy. Such asymmetry facilitates procedures where a tip of the needle is placed proximate to anatomical structures for location verification. Then RF energy may be applied in a selectable direction relative to the needle tip to ablate volumes that include the targeted medial branch nerves or rami, thus denervating facet joints or the sacroiliac joint, respectively, to relieve pain in a patient.

39 Claims, 19 Drawing Sheets

Related U.S. Application Data continuation of application No. 16/933,995, filed on Jul. 20, 2020, now Pat. No. 10,925,664, which is a continuation of application No. 15/098,673, filed on Apr. 14, 2016, now Pat. No. 10,736,688, which is a continuation of application No. 12/940,974, filed on Nov. 5, 2010, now abandoned.

(60) Provisional application No. 61/347,351, filed on May 21, 2010, provisional application No. 61/280,557, filed on Nov. 5, 2009.

(51) Int. Cl.
*A61B 18/00* (2006.01)
*A61B 90/00* (2016.01)

(52) U.S. Cl.
CPC ............... *A61B 2018/00577* (2013.01); *A61B 2018/00595* (2013.01); *A61B 2018/00642* (2013.01); *A61B 2018/00791* (2013.01); *A61B 2018/00821* (2013.01); *A61B 2018/00875* (2013.01); *A61B 2018/1253* (2013.01); *A61B 2018/126* (2013.01); *A61B 2018/1467* (2013.01); *A61B 2090/376* (2016.02); *A61B 2090/3762* (2016.02)

(56) References Cited

U.S. PATENT DOCUMENTS 4,206,762 A 6/1980 Cosman
4,281,667 A 8/1981 Cosman
4,353,371 A 10/1982 Cosman
4,375,220 A 3/1983 Matvias
4,378,809 A 4/1983 Cosman
4,385,636 A 5/1983 Cosman
4,411,266 A 10/1983 Cosman
4,565,200 A 1/1986 Cosman
4,573,980 A 3/1986 Karrasch et al.
4,583,538 A 4/1986 Onik et al.
4,593,703 A 6/1986 Cosman
4,618,978 A 10/1986 Cosman
4,646,752 A 3/1987 Swann et al.
4,653,508 A 3/1987 Cosman
4,660,568 A 4/1987 Cosman
4,676,255 A 6/1987 Cosman
4,698,207 A 10/1987 Bringham et al.
4,787,886 A 11/1988 Cosman
4,796,615 A 1/1989 Bullock et al.
4,827,927 A 5/1989 Newton
4,838,265 A 6/1989 Cosman et al.
4,886,506 A 12/1989 Lovgren et al.
4,907,589 A 3/1990 Cosman
4,966,597 A 10/1990 Cosman
5,010,897 A 4/1991 Leveen
5,160,337 A 11/1992 Cosman
5,217,457 A 6/1993 Delahuerga et al.
5,230,623 A 7/1993 Guthrie et al.
5,233,515 A 8/1993 Cosman
5,244,462 A 9/1993 Delahuerga et al.
5,257,630 A 11/1993 Braitman et al.
5,291,896 A 3/1994 Fonger et al.
5,304,114 A 4/1994 Cosman et al.
5,304,115 A 4/1994 Pflueger et al.
5,312,329 A 5/1994 Beaty et al.
5,312,391 A 5/1994 Wilk
5,318,013 A 6/1994 Wilk
5,324,255 A 6/1994 Passafaro et al.
5,334,183 A 8/1994 Wuchinich
5,342,292 A 8/1994 Nita et al.
5,370,645 A 12/1994 Klicek et al.
5,370,675 A 12/1994 Edwards et al.
5,372,596 A 12/1994 Klicek et al.
5,377,685 A 1/1995 Kazi et al.
5,383,917 A 1/1995 Desai et al.
5,397,301 A 3/1995 Pflueger et al.
5,401,272 A 3/1995 Perkins
5,421,923 A 6/1995 Clarke et al.
5,422,567 A 6/1995 Matsunaga
5,423,809 A 6/1995 Klicek
5,433,739 A 7/1995 Sluijter et al.
5,447,417 A 9/1995 Kuhl et al.
5,458,597 A 10/1995 Edwards et al.
5,472,441 A 12/1995 Edwards et al.
5,472,442 A 12/1995 Klicek
5,474,057 A 12/1995 Makower et al.
5,484,398 A 1/1996 Stoddard
5,486,161 A 1/1996 Lax et al.
5,496,312 A 3/1996 Klicek
5,507,743 A 4/1996 Edwards et al.
5,507,802 A * 4/1996 Imran ..................... A61N 1/05 607/128
5,511,564 A 4/1996 Wilk
5,514,129 A 5/1996 Smith
D372,086 S 7/1996 Grasso et al.
5,536,267 A 7/1996 Edwards et al.
5,541,376 A 7/1996 Ladtkow et al.
5,560,358 A 10/1996 Arnold et al.
5,562,703 A 10/1996 Desai
5,571,147 A 11/1996 Sluijter et al.
5,580,665 A 12/1996 Taguchi et al.
5,599,345 A 2/1997 Edwards et al.
5,599,346 A 2/1997 Edwards et al.
5,611,709 A 3/1997 McAnulty
5,613,966 A 3/1997 Makower et al.
5,628,743 A 5/1997 Cimino
5,662,111 A 9/1997 Cosman
5,662,620 A 9/1997 Lieber et al.
5,662,680 A 9/1997 Desai
5,667,488 A 9/1997 Lundquist et al.
5,669,904 A 9/1997 Platt, Jr. et al.
5,672,173 A 9/1997 Gough et al.
5,672,174 A 9/1997 Gough et al.
5,683,349 A 11/1997 Makower et al.
5,683,384 A 11/1997 Gough et al.
5,701,575 A 12/1997 Taguchi et al.
5,720,744 A 2/1998 Eggleston et al.
5,728,143 A 3/1998 Gough et al.
5,735,847 A 4/1998 Gough et al.
5,738,648 A 4/1998 Lands et al.
5,748,703 A 5/1998 Cosman
5,749,689 A 5/1998 Konig
5,749,846 A 5/1998 Edwards et al.
5,755,754 A 5/1998 Rudie et al.
5,768,679 A 6/1998 Taguchi et al.
5,772,659 A 6/1998 Becker et al.
5,778,043 A 7/1998 Cosman
5,782,827 A 7/1998 Gough et al.
5,792,146 A 8/1998 Cosman
5,797,906 A 8/1998 Rhum et al.
5,800,484 A 9/1998 Gough et al.
5,807,309 A 9/1998 Lundquist et al.
5,810,804 A 9/1998 Gough et al.
5,827,271 A 10/1998 Buysse et al.
5,827,276 A * 10/1998 LeVeen ............. A61B 18/1477 606/49
5,848,967 A 12/1998 Cosman
5,855,576 A 1/1999 LeVeen et al.
5,863,290 A 1/1999 Gough et al.
5,868,740 A 2/1999 LeVeen et al.
5,893,847 A 4/1999 Kordis
5,911,739 A 6/1999 Kordis et al.
5,913,855 A 6/1999 Gough et al.
5,921,992 A 7/1999 Costales et al.
5,925,042 A 7/1999 Gough et al.
5,928,229 A 7/1999 Gough et al.
5,935,123 A 8/1999 Edwards et al.
5,951,547 A 9/1999 Gough et al.
5,968,040 A 10/1999 Swanson et al.
5,980,517 A 11/1999 Gough
5,983,141 A 11/1999 Sluijter et al.
6,006,126 A 12/1999 Cosman
6,013,076 A 1/2000 Goble et al.
6,014,590 A 1/2000 Whayne et al.

(56) References Cited

U.S. PATENT DOCUMENTS

| | | | |
|---|---|---|---|
| 6,015,406 | A | 1/2000 | Goble et al. |
| 6,016,452 | A | 1/2000 | Kasevich |
| 6,039,733 | A | 3/2000 | Buysse et al. |
| 6,041,260 | A | 3/2000 | Stern et al. |
| 6,044,846 | A | 4/2000 | Edwards |
| 6,045,532 | A | 4/2000 | Eggers et al. |
| 6,050,992 | A | 4/2000 | Nichols |
| 6,053,937 | A | 4/2000 | Edwards et al. |
| 6,059,780 | A | 5/2000 | Gough et al. |
| 6,068,627 | A | 5/2000 | Orszulak et al. |
| 6,071,280 | A | 6/2000 | Edwards et al. |
| 6,080,149 | A | 6/2000 | Huang et al. |
| 6,080,150 | A | 6/2000 | Gough |
| 6,090,105 | A | 7/2000 | Zepeda et al. |
| 6,105,581 | A | 8/2000 | Eggers et al. |
| 6,106,521 | A | 8/2000 | Blewett et al. |
| 6,117,134 | A | 9/2000 | Cunningham et al. |
| 6,122,341 | A | 9/2000 | Butler et al. |
| 6,129,726 | A | 10/2000 | Edwards et al. |
| 6,132,425 | A | 10/2000 | Gough |
| 6,139,519 | A | 10/2000 | Blythe |
| 6,139,545 | A | 10/2000 | Utley et al. |
| 6,139,547 | A | 10/2000 | Lontine et al. |
| 6,143,003 | A | 11/2000 | Cosman |
| 6,146,380 | A | 11/2000 | Racz et al. |
| 6,161,048 | A | 12/2000 | Sluijter et al. |
| 6,165,169 | A | 12/2000 | Panescu et al. |
| 6,167,295 | A | 12/2000 | Cosman |
| 6,179,834 | B1 | 1/2001 | Buysse et al. |
| 6,210,403 | B1 | 4/2001 | Klicek |
| 6,210,406 | B1 | 4/2001 | Webster |
| 6,213,999 | B1 | 4/2001 | Platt, Jr. et al. |
| 6,216,043 | B1 | 4/2001 | Swanson et al. |
| 6,217,554 | B1 | 4/2001 | Green |
| 6,221,071 | B1 | 4/2001 | Sherry et al. |
| 6,228,080 | B1 | 5/2001 | Gines |
| 6,228,083 | B1 | 5/2001 | Lands et al. |
| 6,231,570 | B1 | 5/2001 | Tu et al. |
| 6,234,178 | B1 | 5/2001 | Goble et al. |
| 6,235,023 | B1 | 5/2001 | Lee et al. |
| 6,241,725 | B1 | 6/2001 | Cosman |
| 6,241,726 | B1 | 6/2001 | Chia et al. |
| 6,246,912 | B1 | 6/2001 | Sluijter et al. |
| 6,251,106 | B1 | 6/2001 | Becker et al. |
| 6,259,952 | B1 | 7/2001 | Sluijter et al. |
| 6,261,311 | B1 | 7/2001 | Sharkey et al. |
| 6,264,651 | B1 | 7/2001 | Underwood et al. |
| 6,268,200 | B1 | 7/2001 | Tucker et al. |
| 6,275,725 | B1 | 8/2001 | Cosman |
| 6,277,117 | B1 | 8/2001 | Tetzlaff et al. |
| 6,280,441 | B1 | 8/2001 | Ryan |
| 6,283,961 | B1 | 9/2001 | Underwood et al. |
| 6,287,304 | B1 | 9/2001 | Eggers et al. |
| 6,312,426 | B1 | 11/2001 | Goldberg et al. |
| 6,330,478 | B1 | 12/2001 | Lee et al. |
| 6,331,180 | B1 | 12/2001 | Cosman et al. |
| 6,334,861 | B1 | 1/2002 | Chandler et al. |
| 6,352,536 | B1 | 3/2002 | Buysse et al. |
| 6,402,743 | B1 | 6/2002 | Orszulak et al. |
| 6,402,747 | B1 | 6/2002 | Lindermann et al. |
| 6,405,072 | B1 | 6/2002 | Cosman |
| 6,416,520 | B1 | 7/2002 | Kynast et al. |
| 6,419,653 | B2 | 7/2002 | Edwards et al. |
| 6,419,680 | B1 | 7/2002 | Cosman et al. |
| 6,419,798 | B1 | 7/2002 | Topolkaraev et al. |
| 6,425,887 | B1 | 7/2002 | McGuckin et al. |
| 6,440,127 | B2 | 8/2002 | McGovern et al. |
| 6,447,477 | B2 | 9/2002 | Burney et al. |
| 6,447,505 | B2 | 9/2002 | McGovern et al. |
| 6,451,018 | B1 | 9/2002 | Lands et al. |
| 6,454,765 | B1 | 9/2002 | Leveen et al. |
| 6,458,130 | B1 | 10/2002 | Frazier et al. |
| 6,459,769 | B1 | 10/2002 | Cosman |
| 6,461,314 | B1 | 10/2002 | Pant et al. |
| 6,464,704 | B2 | 10/2002 | Schmaltz et al. |
| 6,468,273 | B1 | 10/2002 | Leveen et al. |
| 6,471,695 | B1 | 10/2002 | Behl |
| 6,471,698 | B1 | 10/2002 | Edwards et al. |
| 6,478,793 | B1 | 11/2002 | Cosman et al. |
| 6,500,175 | B1 | 12/2002 | Gough et al. |
| 6,506,189 | B1 | 1/2003 | Rittman, III et al. |
| 6,517,534 | B1 | 2/2003 | McGovern et al. |
| 6,530,922 | B2 | 3/2003 | Cosman et al. |
| 6,533,987 | B2 | 3/2003 | Topolkaraev et al. |
| 6,551,302 | B1 | 4/2003 | Rosinko et al. |
| 6,551,311 | B2 | 4/2003 | Lee et al. |
| 6,562,033 | B2 | 5/2003 | Shah et al. |
| 6,565,562 | B1 | 5/2003 | Shah et al. |
| 6,569,159 | B1 | 5/2003 | Edwards et al. |
| 6,575,967 | B1 | 6/2003 | Leveen et al. |
| 6,575,969 | B1 | 6/2003 | Rittman, III et al. |
| 6,585,735 | B1 | 7/2003 | Frazier et al. |
| 6,602,249 | B1 | 8/2003 | Stoddard et al. |
| 6,605,085 | B1 | 8/2003 | Edwards |
| 6,610,054 | B1 | 8/2003 | Edwards et al. |
| 6,622,731 | B2 | 9/2003 | Daniel et al. |
| 6,623,481 | B1 | 9/2003 | Garbagnati et al. |
| 6,632,221 | B1 | 10/2003 | Edwards et al. |
| 6,632,222 | B1 | 10/2003 | Edwards et al. |
| 6,638,275 | B1 | 10/2003 | McGaffigan et al. |
| 6,641,580 | B1 | 11/2003 | Edwards et al. |
| 6,645,201 | B1 | 11/2003 | Utley et al. |
| 6,652,515 | B1 | 11/2003 | Maguire et al. |
| 6,652,516 | B1 | 11/2003 | Gough |
| 6,660,002 | B1 | 12/2003 | Edwards et al. |
| 6,660,362 | B1 | 12/2003 | Lindsay et al. |
| 6,663,624 | B2 | 12/2003 | Edwards et al. |
| 6,669,693 | B2 | 12/2003 | Friedman |
| 6,682,526 | B1 | 1/2004 | Jones et al. |
| 6,682,528 | B2 | 1/2004 | Frazier et al. |
| 6,685,701 | B2 | 2/2004 | Orszulak et al. |
| 6,685,703 | B2 | 2/2004 | Pearson et al. |
| 6,689,127 | B1 | 2/2004 | Gough et al. |
| 6,690,210 | B2 | 2/2004 | Hadjizada et al. |
| 6,692,490 | B1 | 2/2004 | Edwards |
| 6,699,242 | B2 | 3/2004 | Heggeness |
| 6,706,152 | B2 | 3/2004 | Burazin et al. |
| 6,723,092 | B2 | 4/2004 | Brown et al. |
| 6,740,080 | B2 | 5/2004 | Jain et al. |
| 6,743,226 | B2 | 6/2004 | Cosman et al. |
| 6,743,229 | B2 | 6/2004 | Buysse et al. |
| 6,746,570 | B2 | 6/2004 | Burazin et al. |
| 6,749,719 | B2 | 6/2004 | Burazin et al. |
| 6,752,804 | B2 | 6/2004 | Simpson et al. |
| 6,770,070 | B1 | 8/2004 | Balbierz |
| 6,780,180 | B1 | 8/2004 | Goble et al. |
| 6,803,549 | B2 | 10/2004 | Yu |
| 6,814,712 | B1 | 11/2004 | Edwards et al. |
| 6,837,956 | B2 | 1/2005 | Cowell et al. |
| 6,846,448 | B2 | 1/2005 | Rymer et al. |
| 6,847,848 | B2 | 1/2005 | Sterzer et al. |
| 6,852,091 | B2 | 2/2005 | Edwards et al. |
| 6,866,663 | B2 | 3/2005 | Edwards et al. |
| 6,881,214 | B2 | 4/2005 | Cosman et al. |
| 6,889,089 | B2 | 5/2005 | Behl et al. |
| 6,896,675 | B2 | 5/2005 | Leung et al. |
| 6,907,884 | B2 | 6/2005 | Pellegrino et al. |
| 6,932,810 | B2 | 8/2005 | Ryan |
| 6,958,062 | B1 | 10/2005 | Gough et al. |
| 6,958,064 | B2 | 10/2005 | Rioux et al. |
| 6,961,602 | B2 | 11/2005 | Fuimaono et al. |
| 6,962,587 | B2 | 11/2005 | Johsnon et al. |
| 6,964,660 | B2 | 11/2005 | Maguire et al. |
| 6,966,908 | B2 | 11/2005 | Maguire et al. |
| 6,974,455 | B2 | 12/2005 | Garabedian et al. |
| 6,989,004 | B2 | 1/2006 | Hinchliffe et al. |
| 6,997,925 | B2 | 2/2006 | Maguire et al. |
| 7,025,767 | B2 | 4/2006 | Schaefer et al. |
| 7,033,353 | B2 | 4/2006 | Stoddard et al. |
| 7,044,949 | B2 | 5/2006 | Orszulak et al. |
| 7,048,733 | B2 | 5/2006 | Hartley et al. |
| 7,056,320 | B2 | 6/2006 | Utley et al. |
| 7,074,484 | B2 | 7/2006 | Topolkaraev et al. |
| 7,076,399 | B2 | 7/2006 | Godara |

(56) References Cited

U.S. PATENT DOCUMENTS

| | | | |
|---|---|---|---|
| 7,087,051 | B2 | 8/2006 | Bourne et al. |
| 7,099,712 | B2 | 8/2006 | Fuimaono et al. |
| 7,108,696 | B2 | 9/2006 | Daniel et al. |
| 7,112,197 | B2 | 9/2006 | Hartley et al. |
| 7,115,124 | B1 | 10/2006 | Xiao |
| 7,138,088 | B2 | 11/2006 | Wariar et al. |
| 7,150,743 | B2 | 12/2006 | Zvuloni et al. |
| 7,150,744 | B2 | 12/2006 | Edwards et al. |
| 7,160,296 | B2 | 1/2007 | Pearson et al. |
| 7,163,536 | B2 | 1/2007 | Godara |
| 7,179,256 | B2 | 2/2007 | Mest |
| 7,179,258 | B2 | 2/2007 | Buysse et al. |
| 7,195,629 | B2 | 3/2007 | Behl et al. |
| 7,207,990 | B2 | 4/2007 | Lands et al. |
| 7,229,438 | B2 | 6/2007 | Young |
| 7,258,688 | B1 | 8/2007 | Shah et al. |
| 7,266,414 | B2 | 9/2007 | Cornelius et al. |
| 7,270,660 | B2 | 9/2007 | Ryan |
| 7,270,661 | B2 | 9/2007 | Dahla et al. |
| 7,270,662 | B2 | 9/2007 | Visram et al. |
| 7,276,064 | B2 | 10/2007 | Paul et al. |
| 7,281,666 | B2 | 10/2007 | Smith |
| 7,294,127 | B2 | 11/2007 | Leung et al. |
| 7,306,596 | B2 | 12/2007 | Hillier et al. |
| 7,311,702 | B2 | 12/2007 | Tallarida et al. |
| 7,318,822 | B2 | 1/2008 | Darmos et al. |
| 7,340,307 | B2 | 3/2008 | Maguire et al. |
| 7,344,533 | B2 | 3/2008 | Pearson et al. |
| RE40,279 | E | 4/2008 | Sluijter et al. |
| 7,354,436 | B2 | 4/2008 | Rioux et al. |
| 7,357,798 | B2 | 4/2008 | Sharps et al. |
| 7,371,234 | B2 | 5/2008 | Young |
| RE40,388 | E | 6/2008 | Gines |
| 7,387,626 | B2 | 6/2008 | Edwards et al. |
| 7,387,630 | B2 | 6/2008 | Mest |
| 7,393,351 | B2 | 7/2008 | Woloszko et al. |
| 7,399,299 | B2 | 7/2008 | Daniel et al. |
| 7,416,549 | B2 | 8/2008 | Young et al. |
| 7,419,487 | B2 | 9/2008 | Johnson et al. |
| 7,449,020 | B2 | 11/2008 | Edwards et al. |
| 7,458,971 | B2 | 12/2008 | Zerfas et al. |
| 7,468,062 | B2 | 12/2008 | Oral et al. |
| 7,480,533 | B2 | 1/2009 | Cosman et al. |
| 7,517,346 | B2 | 4/2009 | Sloan et al. |
| 7,524,318 | B2 | 4/2009 | Young et al. |
| 7,533,002 | B2 | 5/2009 | Godara |
| 7,549,986 | B2 | 6/2009 | Rioux et al. |
| 7,561,907 | B2 | 7/2009 | Fuimaono et al. |
| 7,593,778 | B2 | 9/2009 | Chandran et al. |
| 7,596,469 | B2 | 9/2009 | Godara |
| 7,601,149 | B2 | 10/2009 | DiCarlo et al. |
| 7,615,050 | B2 | 11/2009 | Cross et al. |
| 7,670,336 | B2 | 3/2010 | Young et al. |
| 7,670,337 | B2 | 3/2010 | Young |
| 7,678,106 | B2 | 3/2010 | Lee |
| 7,678,107 | B2 | 3/2010 | Young |
| 7,699,844 | B2 | 4/2010 | Utley et al. |
| 7,704,248 | B2 | 4/2010 | Dicarlo |
| 7,749,218 | B2 | 7/2010 | Pellegrino et al. |
| 7,771,420 | B2 | 8/2010 | Butty et al. |
| 7,794,458 | B2 | 9/2010 | McIntyre et al. |
| 7,794,459 | B2 | 9/2010 | Faure |
| 7,797,049 | B2 | 9/2010 | Christopherson et al. |
| 7,799,021 | B2 | 9/2010 | Leung et al. |
| 7,815,571 | B2 | 10/2010 | Deckman et al. |
| 7,819,869 | B2 | 10/2010 | Godara et al. |
| 7,819,871 | B2 | 10/2010 | Paul et al. |
| 7,824,404 | B2 | 11/2010 | Godara et al. |
| 7,828,796 | B2 | 11/2010 | Wong et al. |
| 7,846,157 | B2 | 12/2010 | Kozel |
| 7,874,986 | B2 | 1/2011 | Deckman et al. |
| 7,875,025 | B2 | 1/2011 | Cockburn et al. |
| 7,892,231 | B2 | 2/2011 | Elliott |
| 7,896,871 | B2 | 3/2011 | Bhushan et al. |
| 7,896,872 | B2 | 3/2011 | Finch et al. |
| 7,896,874 | B2 | 3/2011 | Young et al. |
| 7,918,852 | B2 | 4/2011 | Tullis et al. |
| 7,976,542 | B1 | 7/2011 | Cosman et al. |
| 8,052,679 | B2 | 11/2011 | Young |
| 8,080,009 | B2 | 12/2011 | Lee et al. |
| 8,262,574 | B2 | 9/2012 | Placek et al. |
| 8,361,067 | B2 | 1/2013 | Pellegrino et al. |
| 8,414,571 | B2 | 4/2013 | Pellegrino et al. |
| 8,419,730 | B2 | 4/2013 | Pellegrino et al. |
| 8,419,731 | B2 | 4/2013 | Pellegrino et al. |
| 8,425,507 | B2 | 4/2013 | Pellegrino et al. |
| 8,512,330 | B2 | 8/2013 | Epstein et al. |
| 8,512,333 | B2 | 8/2013 | Epstein et al. |
| 8,518,036 | B2 | 8/2013 | Leung et al. |
| 8,518,037 | B2 | 8/2013 | Young |
| 8,535,309 | B2 | 9/2013 | Pellegrino et al. |
| 8,591,507 | B2 | 11/2013 | Kramer et al. |
| 8,613,744 | B2 | 12/2013 | Pellegrino et al. |
| 8,623,014 | B2 | 1/2014 | Pellegrino et al. |
| 8,628,528 | B2 | 1/2014 | Pellegrino et al. |
| 8,663,226 | B2 | 3/2014 | Germain |
| 8,753,335 | B2 | 6/2014 | Moshe et al. |
| 8,758,349 | B2 | 6/2014 | Germain et al. |
| 8,808,284 | B2 | 8/2014 | Pellegrino et al. |
| 8,992,522 | B2 | 3/2015 | Pellegrino et al. |
| 8,992,523 | B2 | 3/2015 | Pellegrino et al. |
| 9,017,325 | B2 | 4/2015 | Pellegrino et al. |
| 9,023,038 | B2 | 5/2015 | Pellegrino et al. |
| 9,039,701 | B2 | 5/2015 | Pellegrino et al. |
| 9,078,678 | B2 | 7/2015 | Zerfas et al. |
| 9,125,671 | B2 | 9/2015 | Germain et al. |
| 9,144,457 | B2 | 9/2015 | Young |
| 9,173,676 | B2 | 11/2015 | Pellegrino et al. |
| 9,173,700 | B2 | 11/2015 | Godara et al. |
| 9,241,760 | B2 | 1/2016 | Godara et al. |
| 9,259,241 | B2 | 2/2016 | Pellegrino et al. |
| 9,265,522 | B2 | 2/2016 | Pellegrino et al. |
| 9,345,537 | B2 | 5/2016 | Harrison et al. |
| 9,402,560 | B2 | 8/2016 | Organ et al. |
| 9,421,064 | B2 | 8/2016 | Pellegrino et al. |
| 9,486,279 | B2 | 11/2016 | Pellegrino et al. |
| RE46,356 | E | 4/2017 | Pellegrino et al. |
| 9,675,406 | B2 | 6/2017 | Moss et al. |
| 9,724,107 | B2 | 8/2017 | Pellegrino et al. |
| 9,775,627 | B2 | 10/2017 | Patel et al. |
| 10,028,753 | B2 | 7/2018 | Pellegrino et al. |
| 10,028,784 | B2 | 7/2018 | Kramer et al. |
| 10,085,783 | B2 | 10/2018 | Emery et al. |
| 10,111,704 | B2 | 10/2018 | Pellegrino et al. |
| 10,258,406 | B2 | 4/2019 | Long |
| 10,265,099 | B2 | 4/2019 | Pellegrino et al. |
| 10,357,307 | B2 | 7/2019 | Harrison et al. |
| 10,661,078 | B2 | 5/2020 | Crosby et al. |
| 10,716,618 | B2 | 7/2020 | Wright et al. |
| 10,736,688 | B2 | 8/2020 | Wright et al. |
| 10,905,440 | B2 | 2/2021 | Pellegrino et al. |
| 10,925,664 | B2 | 2/2021 | Wright et al. |
| RE48,460 | E | 3/2021 | Pellegrino et al. |
| 10,966,782 | B2 | 4/2021 | Wright et al. |
| 11,471,171 | B2 | 10/2022 | Pellegrino et al. |
| 11,806,070 | B2 | 11/2023 | Wright et al. |
| 2001/0012956 | A1 | 8/2001 | Behl et al. |
| 2002/0022864 | A1 | 2/2002 | Mahvi et al. |
| 2002/0026185 | A1 | 2/2002 | Gough |
| 2002/0029037 | A1 | 3/2002 | Kim |
| 2002/0133148 | A1 | 9/2002 | Daniel et al. |
| 2002/0143302 | A1 | 10/2002 | Hinchliffe et al. |
| 2002/0156472 | A1 | 10/2002 | Lee et al. |
| 2002/0188275 | A1 | 12/2002 | McGuckin, Jr. |
| 2002/0188284 | A1 | 12/2002 | To et al. |
| 2003/0018332 | A1 | 1/2003 | Schmaltz et al. |
| 2003/0078595 | A1 | 4/2003 | Cosman |
| 2003/0199862 | A1 | 10/2003 | Simpson et al. |
| 2003/0225364 | A1 | 12/2003 | Kraft et al. |
| 2004/0006336 | A1 | 1/2004 | Swanson |
| 2004/0015176 | A1 | 1/2004 | Cosman |
| 2004/0015218 | A1 | 1/2004 | Finch et al. |
| 2004/0059328 | A1 | 3/2004 | Daniel et al. |
| 2004/0064137 | A1 | 4/2004 | Pellegrino et al. |

(56) References Cited

U.S. PATENT DOCUMENTS

2004/0100376 A1 5/2004 Lye et al.
2004/0122482 A1 6/2004 Tung et al.
2004/0143262 A1 7/2004 Visram et al.
2004/0158239 A1 8/2004 Behl et al.
2004/0176759 A1 9/2004 Krishnamurthy et al.
2004/0199179 A1 10/2004 Elliott
2004/0230187 A1 11/2004 Lee et al.
2004/0260282 A1 12/2004 Gough et al.
2005/0033279 A1 2/2005 Edwards et al.
2005/0059964 A1 3/2005 Fitz
2005/0080410 A1 4/2005 Rioux et al.
2005/0085804 A1 4/2005 McGaffigan
2005/0101944 A1 5/2005 Williams
2005/0101950 A1 5/2005 Gough et al.
2005/0159757 A1 7/2005 Shluzas et al.
2005/0165391 A1 7/2005 Maguire et al.
2005/0171522 A1 8/2005 Christopherson
2005/0177209 A1 8/2005 Leung et al.
2005/0177211 A1 8/2005 Leung et al.
2005/0203503 A1 9/2005 Edwards et al.
2005/0234445 A1 10/2005 Conquergood et al.
2005/0240174 A1 10/2005 Pearson et al.
2005/0267552 A1 12/2005 Conquergood et al.
2005/0277918 A1 12/2005 Shah et al.
2006/0015161 A1 1/2006 Longo et al.
2006/0084965 A1* 4/2006 Young .................. A61B 18/148 606/41
2006/0089635 A1 4/2006 Young et al.
2006/0095029 A1* 5/2006 Young .................. A61B 18/148 606/41
2006/0095115 A1 5/2006 Bladillah et al.
2006/0106376 A1 5/2006 Godara
2006/0111702 A1 5/2006 Oral et al.
2006/0122686 A1 6/2006 Gilad et al.
2006/0122692 A1 6/2006 Gilad et al.
2006/0142756 A1 6/2006 Davies et al.
2006/0173359 A1 8/2006 Lin et al.
2006/0189972 A1 8/2006 Grossman
2006/0200121 A1 9/2006 Mowery
2006/0206111 A1 9/2006 Young
2006/0206127 A1 9/2006 Conquergood et al.
2006/0206128 A1 9/2006 Conquergood et al.
2006/0206129 A1 9/2006 Conquergood et al.
2006/0206130 A1 9/2006 Conquergood et al.
2006/0206131 A1 9/2006 Conquergood et al.
2006/0206132 A1 9/2006 Conquergood et al.
2006/0206133 A1 9/2006 Conquergood et al.
2006/0206134 A1 9/2006 Conquergood et al.
2006/0217705 A1 9/2006 Godara et al.
2006/0229645 A1 10/2006 Bonnette et al.
2006/0247616 A1 11/2006 Edwards et al.
2006/0259026 A1 11/2006 Godara et al.
2006/0259027 A1 11/2006 Kwan et al.
2006/0271036 A1 11/2006 Garabedian et al.
2007/0006215 A1 1/2007 Epstein et al.
2007/0010809 A1 1/2007 Hovda et al.
2007/0016183 A1 1/2007 Lee et al.
2007/0027449 A1 2/2007 Godara et al.
2007/0060921 A1 3/2007 Janssen et al.
2007/0112340 A1 5/2007 Thomas et al.
2007/0112342 A1 5/2007 Pearson et al.
2007/0118191 A1 5/2007 Godara
2007/0123964 A1 5/2007 Davies et al.
2007/0156136 A1 7/2007 Godara et al.
2007/0161905 A1 7/2007 Munrow
2007/0167943 A1 7/2007 Janssen et al.
2007/0179380 A1 8/2007 Grossman
2007/0179491 A1 8/2007 Kratoska et al.
2007/0185522 A1 8/2007 Davies et al.
2007/0203402 A1 8/2007 Godara et al.
2007/0203486 A1 8/2007 Young
2007/0213703 A1 9/2007 Naam et al.
2007/0260223 A1 11/2007 Scheibe et al.
2007/0260234 A1 11/2007 Mccullagh et al.
2007/0282321 A1 12/2007 Shah et al.
2007/0287996 A1 12/2007 Rioux
2008/0009747 A1 1/2008 Saadat et al.
2008/0015569 A1 1/2008 Saadat et al.
2008/0033493 A1 2/2008 Deckman et al.
2008/0045939 A1 2/2008 Lee
2008/0045940 A1 2/2008 Lee
2008/0048786 A1 2/2008 Feldkamp et al.
2008/0065062 A1 3/2008 Leung et al.
2008/0154259 A1 6/2008 Gough et al.
2008/0161804 A1 7/2008 Rioux et al.
2008/0167646 A1 7/2008 Godara et al.
2008/0167649 A1 7/2008 Edwards et al.
2008/0200972 A1 8/2008 Rittman et al.
2008/0208121 A1 8/2008 Youssef et al.
2008/0228180 A1 9/2008 Epstein
2008/0228181 A1 9/2008 Godara et al.
2008/0249392 A1 10/2008 Mest
2008/0249523 A1 10/2008 McPherson et al.
2008/0269558 A1 10/2008 Yahagi et al.
2008/0269739 A1 10/2008 Young et al.
2008/0269774 A1 10/2008 Garcia et al.
2008/0275443 A1 11/2008 Oral et al.
2008/0287944 A1 11/2008 Pearson
2009/0024124 A1 1/2009 Lefler et al.
2009/0054962 A1 2/2009 Lefler et al.
2009/0099544 A1 4/2009 Munrow et al.
2009/0112201 A1 4/2009 Young
2009/0131790 A1 5/2009 Munrow et al.
2009/0138011 A1 5/2009 Epstein
2009/0187177 A1 7/2009 Epstein
2009/0187182 A1 7/2009 Epstein et al.
2009/0187183 A1 7/2009 Epstein
2009/0198232 A1 8/2009 Young et al.
2009/0221998 A1 9/2009 Epstein et al.
2009/0228001 A1 9/2009 Pacey
2009/0287081 A1 11/2009 Grossman et al.
2009/0292259 A1 11/2009 Delano et al.
2009/0299358 A1 12/2009 Lafontaine
2009/0306604 A1 12/2009 Darmos et al.
2009/0318905 A1* 12/2009 Bhargav ................. A61B 18/14 606/1
2010/0004651 A1 1/2010 Biyani
2010/0042098 A1 2/2010 Cross et al.
2010/0049192 A1 2/2010 Holtz et al.
2010/0056926 A1 3/2010 Deckman et al.
2010/0076303 A1 3/2010 McKinley
2010/0076340 A1 3/2010 Eckstein et al.
2010/0099980 A1 4/2010 Godara et al.
2010/0114095 A1 5/2010 Janssen et al.
2010/0130974 A1 5/2010 Young et al.
2010/0185082 A1 7/2010 Chandran et al.
2010/0222677 A1 9/2010 Placek et al.
2011/0184403 A1 7/2011 Brannan
2011/0288540 A1 11/2011 Wright et al.
2012/0239050 A1 9/2012 Linderman et al.
2013/0096549 A1 4/2013 Organ et al.
2015/0335382 A1 11/2015 Pellegrino et al.
2017/0065334 A1 3/2017 Wright et al.
2021/0177502 A1 6/2021 Wright et al.
2025/0345112 A1 11/2025 Wright et al.

FOREIGN PATENT DOCUMENTS

AU 2014200126 A1 1/2014
AU 2014200132 A1 1/2014
AU 2017203519 A1 6/2017
AU 2017203754 A 6/2017
AU 2015261694 B2 10/2018
AU 2019200358 A1 2/2019
AU 2021202406 B2 6/2023
AU 2023229551 A1 9/2023
AU 2025263809 A1 11/2025
BR 11201201019 9-4 B1 12/2021
BR 11201202926 3-3 B1 2/2022
CA 2778997 C 3/2022
CA 2799505 C 4/2022
CN 1211171 A 3/1999
CN 2418844 Y 2/2001
CN 1338909 A 3/2002

(56) References Cited

FOREIGN PATENT DOCUMENTS

| | | | |
|---|---|---|---|
| CN | 103025260 | B | 5/2015 |
| CN | 105167841 | A | 12/2015 |
| CN | 105167844 | A | 12/2015 |
| DE | 2124684 | A1 | 11/1972 |
| EP | 1059067 | B1 | 4/2005 |
| EP | 1645235 | B1 | 8/2010 |
| EP | 2496166 | B1 | 12/2018 |
| EP | 2571439 | B1 | 6/2020 |
| EP | 3556308 | A1 | 12/2023 |
| EP | 3556308 | B1 | 12/2023 |
| EP | 3750501 | A1 | 3/2024 |
| EP | 3750501 | B1 | 3/2024 |
| GB | 2423024 | A | 8/2006 |
| HK | 1183783 | B | 4/2016 |
| HK | 1175388 | B | 2/2020 |
| HK | 40016316 | B | 5/2024 |
| HK | 40042605 | B | 5/2024 |
| IL | 222965 | A | 9/2016 |
| IN | 338591 | B | 6/2020 |
| IN | 371638 | B | 7/2021 |
| JP | 2000-507844 | A | 6/2000 |
| JP | 2001-527428 | A | 12/2001 |
| JP | 2003-527888 | A | 9/2003 |
| JP | 2004-267759 | A | 9/2004 |
| JP | 2008-516667 | A | 5/2008 |
| JP | 2009-504201 | A | 2/2009 |
| JP | 4290894 | B2 | 7/2009 |
| JP | 2013-509966 | A | 3/2013 |
| JP | 2013526940 | A | 6/2013 |
| JP | 5836964 | B2 | 12/2015 |
| JP | 2016019921 | A | 2/2016 |
| JP | 2016064152 | A | 4/2016 |
| KR | 20150031339 | A | 3/2015 |
| KR | 101632429 | B1 | 6/2016 |
| MX | 2012013280 | A | 3/2013 |
| WO | 1996004860 | A1 | 2/1996 |
| WO | 1996016606 | A1 | 6/1996 |
| WO | 1996029946 | A1 | 10/1996 |
| WO | 1997006739 | A2 | 2/1997 |
| WO | 1997006740 | A2 | 2/1997 |
| WO | 1997006855 | A2 | 2/1997 |
| WO | 1997006857 | A2 | 2/1997 |
| WO | 1997029702 | A1 | 8/1997 |
| WO | 1999025260 | A1 | 5/1999 |
| WO | 2000006046 | A1 | 2/2000 |
| WO | 2001028446 | A1 | 4/2001 |
| WO | 0157655 | A2 | 8/2001 |
| WO | 2001057655 | A2 | 8/2001 |
| WO | 2002022032 | A1 | 3/2002 |
| WO | 2002067796 | A1 | 6/2002 |
| WO | 2002054941 | A2 | 7/2002 |
| WO | 2006044105 | A1 | 4/2006 |
| WO | 2006104682 | A1 | 10/2006 |
| WO | 2007005830 | A2 | 1/2007 |
| WO | 2008083044 | A1 | 7/2008 |
| WO | 2011057157 | A1 | 5/2011 |
| WO | 2011113943 | A1 | 9/2011 |
| WO | 2011146243 | A1 | 11/2011 |

OTHER PUBLICATIONS

Request for Reconsideration of Final Office Action Dated Jul. 3, 2014, U.S. Appl. No. 13/101,009 (Sep. 2, 2014).
Applicant-Initiated Interview Summary, U.S. Appl. No. 13/101,009 (Sep. 22, 2014).
Summary of Interview, U.S. Appl. No. 13/101,009 (Oct. 8, 2014).
Amendment and Response to Office Action Dated Oct. 17, 2014, U.S. Appl. No. 13/101,009 (Jan. 16, 2015).
Amendment and Request for Reconsideration of Final Office Action Dated Apr. 6, 2015, U.S. Appl. No. 13/101,009 (Jun. 4, 2015).
Advisory Action Before the Filing of an Appeal Brief, U.S. Appl. No. 13/101,009 (Jun. 12, 2015).
Amendment and Response to Office Action, U.S. Appl. No. 15/092,945 (Dec. 4, 2018).
Amendment and Response to Office Action, U.S. Appl. No. 15/092,945 (Sep. 16, 2019).
Supplemental Amendment, U.S. Appl. No. 15/092,945 (Feb. 24, 2020).
Amendment and Response to Office Action, U.S. Appl. No. 16/933,811 (Nov. 19, 2020).
Preliminary Amendment, U.S. Appl. No. 17/190,224 (Jul. 8, 2024).
Office Action, U.S. Appl. No. 17/190,224 (Jan. 8, 2025).
Amendment and Response to Office Action, U.S. Appl. No. 17/190,224 (Jul. 8, 2025).
Office Action, U.S. Appl. No. 17/190,224 (Oct. 14, 2025).
Preliminary Amendment, U.S. Appl. No. 19/272,521 (Sep. 19, 2025).
Office Action, U.S. Appl. No. 19/272,521 (Dec. 31, 2025).
Examination Report No. 2, Australian Patent Application No. 2015261694 (Sep. 19, 2018).
Examination Report No. 1, Australian Patent Application No. 2023229551 (Nov. 6, 2024).
Govind, J., et al., "Radiofrequency neurotomy for the treatment of third occipital headache," J Neurol Neurosurg Psychiatry, 2003, vol. 74, pp. 88-93.
Lord, S. M., et al., "Percutaneous radio-frequency neurotomy for chronic cervical zygapophyseal-joint pain," The New England Journal of Medicine, Dec. 5, 1996, vol. 335, No. 23, pp. 1721-1726.
Lee, S.-H. et al., "Ultrasound-guided radiofrequency neurotomy in cervical spine: sonoanatomic study of a new technique in cadavers," Clinical Radiology, 2008, vol. 63, pp. 1205-1212.
Communication Pursuant to Article 94(3) EPC, European Patent Application No. 11783944.9 (Feb. 28, 2018).
Communication Regarding Extended European Search Report, European Patent Application No. 20181799.6 (Oct. 20, 2020).
Barauskas et al., Investigation of radiofrequency ablation process in liver tissue by finite element modeling and experiment, *Medicina (Kaunas)*, vol. 43(4), pp. 310-325, 2007.
Berjano, Theoretical modeling for radiofrequency ablation: state-of-the-art and challenges for the future, *BioMedical Engineering OnLine,* vol. 5(24), 17 pages, Apr. 18, 2006.
Burdio et al., Bipolar Saline-enhanced Electrode for Radiofrequency Ablation: Results of Experimental Study of in Vivo Porcine Liver, *Radiology,* vol. 229(2), pp. 447-456, Nov. 2003.
Choi et al., Overlapping Ablation Using a Coaxial Radiofrequency Electrode and Multiple Cannulae System: Experimental Study in ex-Vivo Bovine Liver, *Korean Journal of Radiology,* vol. 4(2), pp. 117-123, Jun. 2003.
Chua, Clinical Anatomy of the Thoracic Dorsal Rami, Thesis at the University of Newcastle, New South Wales, Australia, 220 pages, 1994.
Derby et al., The Efficacy of a Two Needle Electrode Technique in Percutaneous Radiofrequency Rhizotomy: An Investigational Laboratory Study in an Animal Model, *Pain Physician,* vol. 9, pp. 207-214, 2006.
Govind et al., Radiofrequency neurotomy for the treatment of third occipital headache, *Journal of Neurology, Neurosurgery & Psychiatry,* vol. 74(1), pp. 88-93, Jan. 2003.
Liu et al., Abstract, Computer modeling of factors that affect the minimum safety distance required for radiofrequency ablation near adjacent nontarget structures, *Journal of Vascular and Interventional Radiology,* vol. 19(7), pp. 1079-1086, Jul. 2008, Epub. May 27, 2008.
Lord et al., Percutaneous Radio-Frequency Neurotomy for Chronic Cervical Zygapophyseal-Joint Pain, *New England Journal of Medicine,* vol. 335(23), pp. 1721-1726, Dec. 5, 2006.
Mulier et al., Electrodes and multiple electrode systems for radiofrequency ablation: a proposal for updated terminology, *European Radiology,* vol. 15, pp. 798-808, 2005, Epub Feb. 12, 2005.
O'Rourke et al., Current status of liver tumor ablation devices, *Expert Rev. Med. Devices,* vol. 4(4), pp. 523-537, 2007.
AngioDynamics® Incorporated, RITA® StarBurst® Model 75; StarBurst® SOE Electrosurgical Device, StarBurst® XL Electrosurgical Device, MRI Compatible StarBurst® XL Device, MRI Compatible StarBurst® Semi-Flex Electrosurgical Device; Instructions for Use, (no date) in 5 pages.

(56) References Cited

OTHER PUBLICATIONS

AngioDynamics®, StarBurstR XL RFA Device; StarBurst® Semi-Flex RFA Device, http://www.angiodynamics.com/products/starburst-semiflex, 2011, in 2 pages.
Baylis Medical Company, Inc., Pain Management; Sinergy™ System, Apr. 2008, in 6 pages.
Baylis Medical Company, Inc., Pain Management; RF Generator V3 Platform, May 2008, in 6 pages.
Baylis Medical Company, Inc., For Thoracic Medial Branch Neurotomy; ThoraCool™ Pain Management System, 2009, in 3 pages.
Boston Scientific, LeVeen® Needle Electrodes; The Choice for Open, Laparoscopic or Percutaneous Radiofrequency Ablation, 2006, in 2 pages.
Boston Scientific, LeVeen® CoAccess™ Electrode System; Coaxial Radiofrequency Ablation Device, 2006, in 2 pages.
Diros Technology Inc., OWL Pain Management Sets, http://www.dirostech.com/22.php, (no date), in 3 pages.
Diros Technology Inc., OWL Sterile Single Use (Disposable) RF Probes, http://www.dirostech.com/productdetail.php?a=16&b+3, 2007, in 1 page.
Diros Technology Inc., OWL Re-Usable RF Probes, http://www.dirostech.com/productdetail.php?a=17&b=3, 2007, in 1 page.
FDA, Design Control Guidance for Medical Device Manufacturers, Mar. 11, 1997, in 53 pages.
Leibinger®, Electrodes for Neurosurgical Applications, pp. 4-10, 12 (no date).
Leibinger®, Accessories for RF-Electrosurgery; Bipolar and Monoplar Electrodes; Active and Inactive Cannulas; User Manual, Feb. 2000, in 24 pages.
NeuroTherm®, http://www.neurotherm.com/interventional_pain_prod_electrodes.htm, 2007, in 2 pages.
NeuroTherm®, One System, Multiple Applications, Mar. 2007, in 2 pages.
NeuroTherm®, RF for Pain Management; Disposable RF Electrode, (no date) in 2 pages.
NeuroTherm®, RF for Pain Management; Simplicity, (no date) in 2 pages.
Rex Medical, Quadra-Fuse; Multi-pronged Injection Needle, http://www.rexmedical.com/quadrafuse.html, 2010, in 2 pages.
Smith & Nephew Endoscopy, Electrothermal 20S Spine System, http://endo.smithnephew.com/fr/node.asp?NodeId=3592, (no date) in 2 pages.
Stryker Instruments, "MultiGen™ One Machine; Four Lesions; Multiple Options," Jul. 2008, in 8 pages.
International Search Report and Written Opinion of the International Searching Authority for International Application No. PCT/US2010/055744, mailed on Mar. 1, 2011, in 34 pages.
International Search Report and Written Opinion of the International Searching Authority for International Application No. PCT/US2011/035253 mailed on Aug. 18, 2011.
International Preliminary Report on Patentability issued in PCT/US2011/035253, dated Nov. 27, 2012.
Patent Examination Report issued in Australian Application No. 2011256709, dated Mar. 22, 2013.
Patent Examination Report issued in Australian Application No. 2010314930, dated Jul. 26, 2013.
Notice of Acceptance issued in Australian Application No. 2010314930, dated Oct. 14, 2013.
Notice of Acceptance issued in Australian Application No. 2011256709, dated Oct. 10, 2013.
Office Action issued in U.S. Appl. No. 13/101,009, dated Mar. 6, 2014.
Office Action issued in Japanese Application No. 2012-538056, dated May 19, 2014.
Final Office Action issued in U.S. Appl. No. 13/101,009, dated Jul. 3, 2014.
Office Action issued in Japanese Application No. 2013-511205, dated Aug. 4, 2014.
Office Action issued in Chinese Application No. 201180035655.7, dated Aug. 25, 2014.
Office Action issued in U.S. Appl. No. 13/101,009, dated Oct. 17, 2014.
Office Action issued in Korean Application No. 10-2012-7033363, dated Dec. 23, 2014.
Patent Examination Report issued in Australian Application No. 2014200132, dated Dec. 1, 2014.
Supplemental European Search Report and Search Opinion issued in EP Application No. 10829203.8, mailed May 9, 2014.
Supplemental European Search Report and Search Opinion issued in EP Application No. 11783944, dated Jun. 23, 2014.
Biomerics LLC, Statement of Claim, *Biomerics LLC* v *Diros Technology Inc & M Medical Pty Ltd,* NSD438/2019, Federal Court of Australia, Mar. 22, 2019, 10 pages.
Diros Technology Inc, Statement of Cross Claim, *Biomerics LLC* v *Diros Technology Inc & M Medical Pty Ltd,* NSD438/2019, Federal Court of Australia, May 13, 2019, 5 pages.
Diros Technology Inc., RF Trident Cannulae, Last Accessed Aug. 20, 2019, available at https://dirostech.com/product-details/rf-tridenttrident-hybrid-cannulae/, 7 pages.
Diros Technology Inc., RF Trident Hybrid Cannulae, Last Accessed Aug. 20, 2019, available at https://dirostech.com/product-details/rf-trident-hybrid-cannulae/, 10 pages.
Food and Drug Administration, 510(k) Summary for Diros OWL Sterile Single Use Trident R.F. Insulated Cannulae Models DTR and DTRH, Jul. 30, 2015, 11 pages.
Ahmed et al., Principles of and Advances in Percutaneous Ablation, Radiology, Feb. 2011, pp. 351-369, vol. 258, No. 2.
Chen et al., Optimizing Electrode Placement Using Finite-Element Models in Radiofrequency Ablation Treatment Planning, IEEE Transactions on Biomedical Engineering, Feb. 2009, pp. 237-245, vol. 56, No. 2.
Haemmerich et al., Hepatic Bipolar Radio-Frequency Ablation Between Separated Multiprong Electrodes, IEEE Transactions on Biomedical Engineering, Oct. 2001, pp. 1145-1152, vol. 48, No. 10.
Haemmerich et al., Large-Volume Radiofrequency Ablation of ex Vivo Bovine Liver with Multiple Cooled Cluster Electrodes, Radiology, Feb. 2005, pp. 563-568, vol. 234, No. 2.
Laeseke et al., Multiple-Electrode RF Ablation Creates Confluent Areas of Necrosis: Results in in vivo Porcine Liver, Radiology, Oct. 2006, pp. 116-124.
Quaranta et al., FEM Analysis of RF Breast Ablation: Multiprobe versus Cool-tip Electrode, Anticancer Research, 2007, pp. 775-784.
Scharf et al., Ablation of Persistent Atrial Fibrillation Using Multielectrode Catheters and Duty-Cycled Radiofrequency Energy, Journal of the American College of Cardiology, Oct. 6, 2009, pp. 1450-1456, vol. 54, No. 15.
Shirato et al., Small Hepatocellular Carcinoma: Therapeutic Effectiveness of Percutaneous Radio Frequency Ablation Therapy With a LeVeen Needle Electrode, American Institute of Ultrasound in Medicine, 2002, pp. 67-76.
IP Australia, Patent Examination Report No. 2, Australian Patent Application No. 2014200132, Apr. 8, 2015, 3 pages.
IP Australia, Examination Report No. 1 for standard patent application, Australian Patent Application No. 2015261694, Sep. 27, 2017, 3 pages.
Brazilian National Institute of Industrial Property, Search Report, Brazilian Patent Application No. BR112012010199-4, Jul. 23, 2019, 6 pages.
Canadian Intellectual Property Office, Notification of Requisition by the Examiner, Canadian Patent Application No. 2,778,997, Jun. 9, 2017, 7 pages.
Canadian Intellectual Property Office, Notification of Requisition by the Examiner, Canadian Patent Application No. 2,778,997, May 23, 2019, 5 pages.
Intellectual Property India, Examination Report, Indian Patent Application No. 3638/DELNP/2012, Mar. 13, 2019, 5 pages.
Japan Patent Office, Notice of Reasons for Rejection, Japanese Patent Application No. 2012-538056, Feb. 2, 2015, 7 pages.
Japan Patent Office, Notice of Reasons for Rejection, Japanese Patent Application No. 2015-215570, Oct. 24, 2016, 15 pages.
IP Australia, Patent Examination Report No. 1, Australian Patent Application No. 2014200126, May 27, 2016, 6 pages.

(56) References Cited

OTHER PUBLICATIONS

Canadian Intellectual Proprety Office, Notification of Requisition by the Examiner, Canadian Patent Application No. 2,799,505, Mar. 17, 2017, 5 pages.
Canadian Intellectual Proprety Office, Notification of Requisition by the Examiner, Canadian Patent Application No. 2,799,505, Apr. 15, 2019, 10 pages.
CNIPA, National Intellectual Property Administration, PRC, Office Action, Chinese Patent Application No. 201510151627.1, Feb. 22, 2017, 8 pages.
CNIPA, National Intellectual Property Administration, PRC, Office Action, Chinese Patent Application No. 201510148998.4, Mar. 2, 2017, 10 pages.
European Patent Office, Communication Pursuant to Article 94(3) EPC, European Patent Application No. 11 783 944.9-1124, Feb. 28, 2018, 4 pages.
Israel Patent Office, Office Action, Israeli Patent Application No. 222965, May 14, 2015, 3 pages.
Intellectual Property India, Examination Report, Indian Patent Application No. 9943/DELNP/2012, Jul. 30, 2019, 6 pages.
Japan Patent Office, Notice of Reasons for Rejection, Japanese Patent Application No. 2013-511205, Feb. 9, 2015, 5 pages.
Japan Patent Office, Decision of Rejection, Japanese Patent Application No. 2013-511205, Aug. 10, 2015, 4 pages.
Japan Patent Office, Appeal No. 2015-21839, Notice of Reasons for Rejection, Japanese Patent Application No. 2013-511205, Oct. 3, 2016, 8 pages.
Japan Patent Office, Notice of Reasons for Rejection, Japanese Patent Application No. 2015-240011, Jan. 4, 2017, 12 pages.
Korean Intellectual Property Office, Notice to Submit Response, Korean Patent Application No. 10-2012-7033363, May 4, 2015, 14 pages.
Korean Intellectual Property Office, Notice to Submit Response, Korean Patent Application No. 10-2015-7004378, Sep. 25, 2017, 13 pages.
Mexican Institute of Industrial Property, Requirement 1, Mexican Patent Application No. MX/a/2012/013280, Feb. 17, 2015, 4 pages.
Mexican Institute of Industrial Property, Requirement 2, Mexican Patent Application No. MX/a/2012/013280, May 27, 2015, 8 pages.
United States Patent and Trademark Office, Office Action, U.S. Appl. No. 13/101,009, Apr. 6, 2015, 26 pages.
United States Patent and Trademark Office, Office Action, U.S. Appl. No. 15/092,945, Jun. 4, 2018, 6 pages.
United States Patent and Trademark Office, Office Action, U.S. Appl. No. 15/092,945, Mar. 14, 2019, 15 pages.
United States Patent and Trademark Office, Applicant-Initiated Interview Summary, U.S. Appl. No. 15/092,945, Aug. 27, 2019, 4 pages.
European Patent Office, European Search Report and EPO Form 1703 01.91 TRI for European Patent Application No. EP 18215729.7, Sep. 6, 2019, 5 pages.
European Patent Office, Communication Under Rule 71(3) EPC for European Patent Application No. EP 11783944.9, Dec. 18, 2019, 125 pages.
Instituto Nacional Da Propriedade Industrial, Search Report for Brazilian Patent Application No. BR112012029263-3, Dec. 6, 2019, 8 pages.
United States Patent and Trademark Office, Applicant-Initiated Interview Summary for U.S. Appl. No. 15/092,945, Feb. 18, 2020, 4 pages.
Canadian Intellectual Property Office, Office Action for Canadian Patent Application No. 2,799,505, dated Apr. 8, 2020, 4 pages.
European Patent Office, Decision to Grant a European Patent Pursuant to Article 97(1) EPC for European Patent Application No. 11783944.9, dated May 28, 2020, 2 pages.
David Lawson Morris, Affidavit Submitted in Federal Court of Australia Case No. NSD 438 of 2019, dated Apr. 17, 2020, 29 pages.
Susanne Monica Hantos, Affidavit Submitted in Federal Court of Australia Case No. NSD 438 of 2019, dated Apr. 21, 2020, 765 pages.
Peter Darmos, Affidavit Submitted in Federal Court of Australia Case No. NSD 438 of 2019, dated Apr. 21, 2020, 716 pages.
William Samual Hunter, Affidavit Submitted in Federal Court of Australia Case No. NSD 438 of 2019, dated Apr. 6, 2020, 158 pages.
Daniel Christopher Higgs, Affidavit Submitted in Federal Court of Australia Case No. NSD 438 of 2019, dated Apr. 6, 2020, 26 pages.
IP Australia, Examination Report No. 1 for Standard Patent Application for Australian Patent Application No. 2019200358, dated Apr. 20, 2020, 3 pages.
Canadian Intellectual Property Office, Office Action for Canadian Patent Application No. 2,778,997, dated May 15, 2020, 3 pages.
United States Patent and Trademark Office, Notice of Allowance for U.S. Appl. No. 15/092,945, dated Mar. 16, 2020, 16 pages.
Leslie W. Organ, Affidavit Submitted in Federal Court of Australia Case No. NSD 438 of 2019, dated Jul. 5, 2020, 19 pages.
William Samuel Hunter, Affidavit Submitted in Federal Court of Australia Case No. NSD 438 of 2019, dated Jul. 20, 2020, 32 pages.
Marc Andrew Russo, Affidavit Submitted in Federal Court of Australia Case No. NSD 438 of 2019, dated Jul. 20, 2020, 70 pages.
Peter Darmos, Amended Statement of Cross Claim Submitted in Federal Court of Australia Case No. NSD 438 of 2019, dated Jun. 5, 2020, 7 pages.
Peter Darmos, Further Amended Statement of cross claim, as proposed for submission in Federal Court of Australia Case No. NSD 438 of 2019, dated Oct. 2020, 7 pages.
David Lawson Morris, Affidavit Submitted in Federal Court of Australia Case No. NSD 438 of 2019, dated Oct. 21, 2020, 37 pages.
United States Patent and Trademark Office, Office Action in U.S. Appl. No. 16/933,811, dated Aug. 19, 2020, 34 pages.
Sarah Louise Matheson, Affidavit Submitted in Federal Court of Australia Case No. NSD 438 of 2019, dated May 28, 2021, 40 pages.
Sarah Louise Matheson, Amended Defence to Further Amended Statement of cross-claim Submitted in Federal Court of Australia Case No. NSD 438 of 2019, dated Apr. 7, 2021, 4 pages.
Sarah Matheson, Interlocutory application Submitted in Federal Court of Australia Case No. NSD 438 of 2019, dated May 28, 2021, 5 pages.
Marc Andrew Russo, Affidavit Submitted in Federal Court of Australia Case No. NSD 438 of 2019, dated Apr. 15, 2021, 6 pages.
William Samuel Hunter, Affidavit Submitted in Federal Court of Australia Case No. NSD 438 of 2019, dated Apr. 15, 2021, 7 pages.
Justice Nicholas, Order in Federal Court of Australia Case No. NSD 438 of 2019, dated Jun. 1, 2021, 5 pages.
Peter Darmos, First Respondent's Statement of Particulars in Opposition to Amendment Submitted in Federal Court of Australia Case No. NSD 438 of 2019, dated Jun. 11, 2021, 4 pages.
Peter Darmos, Reply to Amended Defence to Further Amended Statement of Cross-Claim Submitted in Federal Court of Australia Case No. NSD 438 of 2019, dated Jun. 18, 2021, 3 pages.
Steven Daniel, Affidavit Submitted in Federal Court of Australia Case No. NSD 438 of 2019, dated Jul. 14, 2021, 16 pages.
Ilya Gavrilov, Affidavit Submitted in Federal Court of Australia Case No. NSD 438 of 2019, dated Jul. 14, 2021, 94 pages.
C Dimitriadis, Diros's Note and Submissions for Case Management Hearing Submitted in Federal Court of Australia Case No. NSD 438 of 2019, dated Aug. 12, 2021, 3 pages.
C L Cochrane, Applicant/Cross-Respondent's Note for Aug. 13, 2021 Hearing Submitted in Federal Court of Australia Case No. NSD 438 of 2019, dated Aug. 12, 2021, 3 pages.
Auscript, Transcript of Proceedings before Nocholas J in Federal Court of Australia Case No. NSD 438 of 2019, dated Aug. 13, 2021, 26 pages.
Justice Nicholas, Order in Federal Court of Australia Case No. NSD 438 of 2019, dated Aug. 16, 2021, 5 pages.
William Samuel Hunter, Affidavit Submitted in Federal Court of Australia Case No. NSD 438 of 2019, dated Sep. 10, 2021, 120 pages.
Marc Andrew Russo, Affidavit Submitted in Federal Court of Australia Case No. NSD 438 of 2019, dated Sep. 10, 2021, 120 pages.
Bradley D Vilims, Affidavit Submitted in Federal Court of Australia Case No. NSD 438 of 2019, dated Sep. 19, 2021, 63 pages.

(56) References Cited

OTHER PUBLICATIONS

Justice Nicholas, Orders in Federal Court of Australia Case No. NSD 438 of 2019, dated Oct. 28, 2021, 6 pages.
IP Australia, Examination Report No. 1 for Australian Patent Application No. 2019200358, dated Apr. 20, 2020, 3 pages.
IP Australia, Examination Report No. 1 for Australian Patent Application No. 2021202406, dated Jun. 8, 2022, 7 pages.
IP Australia, Notice of Acceptance for Australian Patent Application No. 2021202406, dated Jun. 1, 2023, 54 pages.
National Institute of Industrial Property, Technical Examination Report for Brazilian Patent Application No. BR112012010199-4, dated Jun. 16, 2021, 8 pages.
National Institute of Industrial Property, Technical Examination Report for Brazilian Patent Application No. BR112012010199-4, dated Oct. 21, 2021, 4 pages.
National Institute of Industrial Property, Technical Examination Report for Brazilian Patent Application No. BR112012029263-3, dated Aug. 11, 2021, 7 pages.
National Institute of Industrial Property, Technical Examination Report for Brazilian Patent Application No. BR112012029263-3, dated Dec. 7, 2021, 4 pages.
Canadian Intellectual Property Office, Commissioner's Notice—Application Found Allowable in Canadian Patent Application No. 2,778,997, dated Nov. 29, 2021, 1 page.
Canadian Intellectual Property Office, Requisition in Canadian Patent Application No. 2,799,505, dated Jan. 29, 2021, 4 pages.
Canadian Intellectual Property Office, Commissioner's Notice—Application Found Allowable in Canadian Patent Application No. 2,799,505, dated Jan. 13, 2022, 1 page.
European Patent Office, Extended European Search Report in European Patent Application No. 18215729.7, dated Sep. 9, 2019, 7 pages.
European Patent Office, Intention to Grant in European Patent Application No. 18215729.7, dated May 16, 2023, 205 pages.
European Patent Office, Extended European Search Report in European Patent Application No. 20181799.6, dated Oct. 20, 2020, 8 pages.
Intellectual Property India, Examination Report in Indian Patent Application No. 202018025757, dated Jun. 30, 2021, 5 pages.
United States Patent and Trademark Office, Applicant-Initiated Interview Summary in U.S. Appl. No. 16/933,811 dated Nov. 20, 2020, 3 pages.
United States Patent and Trademark Office, Notice of Allowance and Examiner-Initiated Interview Summary in U.S. Appl. No. 16/933,811 dated Feb. 16, 2021, 10 pages.
*Stratus Medical, LLC* v. *Avanos Medical, Inc et al.,* D. Del. Case 1:25-cv-00546-CFC, Document 1, Complaint for Patent Infringement (May 2, 2025).
IPR2024-01210, Paper 1, Petition for IPR (Jul. 26, 2024).
IPR2024-01210, Paper 9, Inst. Decision (Feb. 6, 2025).
IPR2024-01210, Paper 16, Patent Owner Response to Petition for IPR (May 23, 2025).
IPR2024-01210, Paper 33, Petitioner's Reply to Patent Owner Response (Sep. 5, 2025).
IPR2024-01210, Paper 43, Patent Owner's Surreply (Sep. 26, 2025).
IPR2024-01210, Ex. 1032, Tucker Decl. (Jul. 26, 2024).
IPR2024-01211, Paper 1, Petition for IPR (Jul. 26, 2024).
IPR2024-01211, Paper 9, Inst. Decision (Feb. 6, 2025).
IPR2024-01211, Paper 16, Patent Owner Response to Petition for IPR (May 23, 2025).
IPR2024-01211, Paper 33, Petitioner's Reply to Patent Owner Response (Sep. 5, 2025).
IPR2024-01211, Paper 43, Patent Owner's Surreply (Sep. 26, 2025).
IPR2024-01211, Ex. 1033, Tucker Decl. (Jul. 26, 2024).
IPR2024-01212, Paper 1, Petition for IPR (Jul. 26, 2024).
IPR2024-01212, Paper 8, Inst. Decision (Feb. 6, 2025).
IPR2024-01212, Paper 14, Patent Owner Response to Petition for IPR (May 23, 2025).
IPR2024-01212, Paper 31, Petitioner's Reply to Patent Owner Response (Sep. 5, 2025).
IPR2024-01212, Paper 41, Patent Owner's Surreply (Sep. 26, 2025).
IPR2024-01212, Ex. 1034, Tucker Decl. (Jul. 26, 2024).
IPR2024-01209, Paper 47, Patent Owner's Motion to Exclude Evidence (Oct. 17, 2025).
IPR2024-01209, Paper 48, Patent Owner's Brief in Support of Its Filing of Exhibits 2044 and 2045 (Oct. 17, 2025).
IPR2024-01209, Paper 49, Petitioner's Motion to Exclude Evidence (Oct. 17, 2025).
IPR2024-01209, Paper 50, Patent Owner's Opposition to Petitioner's Motion to Exclude Evidence (Oct. 24, 2025).
IPR2024-01209, Paper 51, Petitioner's Opposition to Patent Owner's Motion to Exclude Evidence (Oct. 24, 2025).
IPR2024-01209, Paper 52, Petitioner's Responsive Brief to Patent Owner's Brief Regarding Exhibits 2044 and 2045 (Oct. 24, 2025).
IPR2024-01209, Paper 53, Patent Owner's Reply to Petitioner's Opposition to Patent Owner's Motion to Exclude Evidence (Oct. 31, 2025).
IPR2024-01209, Paper 54, Petitioner's Reply in Support of Its Motion to Exclude (Oct. 31, 2025).
IPR2024-01209, Paper 58, Petitioner's Demonstrative Exhibit (Nov. 6, 2025).
IPR2024-01209, Exhibit 2046, Stratus's Demonstrative Exhibits (Nov. 6, 2025).
IPR2024-01209, Paper 62, Record of Oral Hearing Held: Nov. 6, 2025 (Dec. 8, 2025).
IPR2024-01209, Exhibit 1064, Vesta 510(k) Approval (Feb. 7, 2020).
IPR2024-01210, Paper 49, Patent Owner's Motion to Exclude Evidence (Oct. 17, 2025).
IPR2024-01210, Paper 50, Patent Owner's Brief in Support of Its Filing of Exhibits 2044 and 2045 (Oct. 17, 2025).
IPR2024-01210, Paper 51, Petitioner's Motion to Exclude Evidence (Oct. 17, 2025).
IPR2024-01210, Paper 52, Patent Owner's Opposition to Petitioner's Motion to Exclude Evidence (Oct. 24, 2025).
IPR2024-01210, Paper 53, Petitioner's Opposition to Patent Owner's Motion to Exclude Evidence (Oct. 24, 2025).
IPR2024-01210, Paper 54, Petitioner's Responsive Brief to Patent Owner's Brief Regarding Exhibits 2044 and 2045 (Oct. 24, 2025).
IPR2024-01210, Paper 55, Patent Owner's Reply to Petitioner's Opposition to Patent Owner's Motion to Exclude Evidence (Oct. 31, 2025).
IPR2024-01210, Paper 56, Petitioner's Reply in Support of Its Motion to Exclude (Oct. 31, 2025).
IPR2024-01211, Paper 49, Patent Owner's Motion to Exclude Evidence (Oct. 17, 2025).
IPR2024-01211, Paper 50, Patent Owner's Brief in Support of Its Filing of Exhibits 2044 and 2045 (Oct. 17, 2025).
IPR2024-01211, Paper 51, Petitioner's Motion to Exclude Evidence (Oct. 17, 2025).
IPR2024-01211, Paper 52, Patent Owner's Opposition to Petitioner's Motion to Exclude Evidence (Oct. 24, 2025).
IPR2024-01211, Paper 53, Petitioner's Opposition to Patent Owner's Motion to Exclude Evidence (Oct. 24, 2025).
IPR2024-01211, Paper 54, Petitioner's Responsive Brief to Patent Owner's Brief Regarding Exhibits 2044 and 2045 (Oct. 24, 2025).
IPR2024-01211, Paper 55, Patent Owner's Reply to Petitioner's Opposition to Patent Owner's Motion to Exclude Evidence (Oct. 31, 2025).
IPR2024-01211, Paper 56, Petitioner's Reply in Support of Its Motion to Exclude (Oct. 31, 2025).
IPR2024-01212, Paper 47, Patent Owner's Motion to Exclude Evidence (Oct. 17, 2025).
IPR2024-01212, Paper 48, Patent Owner's Brief in Support of Its Filing of Exhibits 2044 and 2045 (Oct. 17, 2025).
IPR2024-01212, Paper 49, Petitioner's Motion to Exclude Evidence (Oct. 17, 2025).
IPR2024-01212, Paper 50, Patent Owner's Opposition to Petitioner's Motion to Exclude Evidence (Oct. 24, 2025).

(56) References Cited

OTHER PUBLICATIONS

IPR2024-01212, Paper 51, Petitioner's Opposition to Patent Owner's Motion to Exclude Evidence (Oct. 24, 2025).
IPR2024-01212, Paper 52, Petitioner's Responsive Brief to Patent Owner's Brief Regarding Exhibits 2044 and 2045 (Oct. 24, 2025).
IPR2024-01212, Paper 53, Patent Owner's Reply to Petitioner's Opposition to Patent Owner's Motion to Exclude Evidence (Oct. 31, 2025).
IPR2024-01212, Paper 54, Petitioner's Reply in Support of Its Motion to Exclude (Oct. 31, 2025).
IPR2024-01209, Ex. 1019, Cohen et al., "Randomized Placebo-controlled Study Evaluating Lateral Branch Radiofrequency Denervation for Sacroiliac Joint Pain" (Aug. 2, 2008).
IPR2024-01209, Ex. 1031, Tucker Decl. (Jul. 26, 2024).
IPR2024-01209, Ex. 1042, Tucker Reply Decl. (Sep. 5, 2025).
IPR2024-01209, Ex. 1045, Crosby Dep. Tr. (Aug. 5, 2025).
IPR2024-01209, Ex. 1046, Russo Dep. Tr. (Aug. 22, 2025).
IPR2024-01209, Ex. 1048, Jorgensen Dep. Tr. (Aug. 26, 2025).
IPR2024-01209, Ex. 1049, Nimbus 510(k) Summary (Sep. 21, 2012).
IPR2024-01209, Ex. 1051, Robert E. Wright et al., "Radiofrequency Ablation in Interventional Pain Management Using RF Multitined Expandable Electrode: First Edition" (Sep. 5, 2025).
IPR2024-01209, Ex. 1052, Konno Decl. (Sep. 2, 2025).
IPR2024-01209, Ex. 1053, Johnson Decl. (Sep. 4, 2025).
IPR2024-01209, Ex. 1054, U.S. Appl. No. 61/280,557 Prosecution History (Nov. 5, 2009).
IPR2024-01209, Ex. 1055, Baylis Sinergy System User Guide (Sep. 2008).
IPR2024-01209, Ex. 1056, C. Norman Shealy, "Facet Denervation in the Management of Back and Sciatic Pain" (1976).
IPR2024-01209, Ex. 1058, Cosman TEW Brochure (2005).
IPR2024-01209, Ex. 1062, James M. Gere, "Mechanics of Materials: Fifth Edition" (2001).
IPR2024-01209, Ex. 1063, Serope Kalpakjian et al., "Manufacturing Processes for Engineering Materials: Fourth Edition" (2003).
IPR2024-01209, Ex. 2001, Russo Decl. (May 21, 2025).
IPR2024-01209, Ex. 2003, Robert E. Wright et al., "Radiofrequency Ablation in Interventional Pain Management Using RF Multitined Expandable Electrode: First Edition" (Sep. 5, 2025).
IPR2024-01209, Ex. 2004, Marc Russo et al., "A History of the Development of Radiofrequency Neurotomy" (Dec. 24, 2021).
IPR2024-01209, Ex. 2005, Marc Russo et al., "Development and Description of a New Multifidus-Sparing Radiofrequency Neurotomy Technique for Facet Joint Pain" (Mar. 22, 2021).
IPR2024-01209, Ex. 2006, Crosby Declaration (May 22, 2025).
IPR2024-01209, Ex. 2008, Nimbus Claim Charts (May 23, 2025).
IPR2024-01209, Ex. 2009, Acessa 510(k) Summary (Nov. 5, 2012).
IPR2024-01209, Ex. 2010, Acessa ProVu User Guide (May 23, 2025).
IPR2024-01209, Ex. 2011, Complaint for Patent Infringement, D. Del. Case 1:25-cv-00546-CFC (May 2, 2025).
IPR2024-01209, Ex. 2014, Fed. Ct. of Aust. Order (Oct. 28, 2021).
IPR2024-01209, Ex. 2016, Jorgensen Decl. (May 22, 2025).
IPR2024-01209, Ex. 2019, Trident 510(k) Summary (Jul. 30, 2015).
IPR2024-01209, Ex. 2020, Tucker Dep. Tr. (May 7, 2025).
IPE2024-01209, Ex. 2025, Stratus Medical Ranked No. 483 Fastest-Growing Company in North America on the 2024 Deloitte Technology Fast 500TM (Nov. 21, 2024).
IPE2024-01209, Ex. 2026, Stratus Medical was recognized in Malibu, CA this week by the Pepperdine Most Fundable Companies List (May 16, 2025).
IPR2024-01209, Ex. 2041, Johnson Dep. Tr. (Sep. 18, 2025).
IPR2024-01209, Ex. 2043, Konno Dep. Tr. (Sep. 19, 2025).
IPR2024-01209, Ex. 2044, Serope Kalpakjian et al., "Manufacturing Processes for Engineering Materials: Fourth Edition" (2003).
IPR2024-01209, Ex. 2045, Serope Kalpakjian et al., "Manufacturing Processes for Engineering Materials: Fifth Edition" (2009).
IPR2024-01209, Paper 1, Petition for IPR (Jul. 26, 2024).
IPR2024-01209, Paper 8, Inst. Decision (Feb. 6, 2025).
IPR2024-01209, Paper 14, Patent Owner Response to Petition for IPR (May 23, 2025).
IPR2024-01209, Paper 31, Petitioner's Reply to Patent Owner Response (Sep. 5, 2025).
IPR2024-01209, Paper 41, Patent Owner's Surreply (Sep. 26, 2025).
IPR2024-01212, Paper 68, Judgement: Final Written Decision Determining All Challenged Claims Unpatentable Dismissing the Parties' Motions to Exclude (Papers 47, 49) (Mar. 5, 2026).
IPR2024-01210, Paper 71, Judgement: Determining All Challenged Claims Unpatentable Dismissing the Parties' Motions to Exclude (Mar. 6, 2026).
IPR2024-01211, Paper 70, Judgement: Determining All Challenged Claims Unpatentable Dismissing the Parties' Motions to Exclude (Mar. 6, 2026).
IPR2024-01209, Paper 70, Judgment: Determining All Challenged Claims Unpatentable Dismissing the Parties' Motions to Exclude (Mar. 10, 2026).
Amendment and Response to Office Action, U.S. Appl. No. 17/190,224 (Apr. 14, 2016).
Amendment and Response to Office Action, U.S. Appl. No. 19/272,521 (Mar. 31, 2016).
Office Action, U.S. Appl. No. 19/272,521 (Apr. 23, 2026).
U.S. Appl. No. 19/664,743 (to reissue U.S. Pat. No. 10,736,688) (Apr. 30, 2026).

* cited by examiner

SYSTEMS FOR RADIOFREQUENCY NEUROTOMY

RELATED APPLICATIONS

This application is a continuation of U.S. patent application Ser. No. 12/940,974, filed on Nov. 5, 2010, which is hereby incorporated by reference in its entirety and which claims the benefit of U.S. Provisional Patent App. No. 61/280,557, filed on Nov. 5, 2009, and U.S. Provisional Patent App. No. 61/347,351, filed on May 21, 2010, both of which are hereby incorporated by reference in their entirety.

FIELD OF THE INVENTION

The present invention relates to thermal ablation systems and methods and, more specifically, to improved systems and methods for performing Radio Frequency (RF) neurotomy. The invention is particularly apt for spinal RF neurotomy procedures.

BACKGROUND OF THE INVENTION

Thermal ablation involves the creation of temperature changes sufficient to produce necrosis in a specific volume of tissue within a patient. The target volume may be, for example, a nerve or tumor. A significant challenge in ablation therapy is to provide adequate treatment to the targeted tissue while sparing the surrounding structures from injury.

RF ablation uses electrical energy transmitted into a target volume through an electrode to generate heat in the area of the electrode tip. The radio waves emanate from a non-insulated distal portion of the electrode tip. The introduced radiofrequency energy causes molecular strain, or ionic agitation, in the area surrounding the electrode as the current flows from the electrode tip to ground. The resulting strain causes the temperature in the area surrounding the electrode tip to rise. Temperature calibration or measurement devices, for example thermocouples, in the electrode may provide feedback and allow precise control of the temperatures produced at the electrode tip.

RF neurotomy uses RF energy to cauterize a target nerve to disrupt the ability of the nerve to transmit pain signals to the brain. Known RF neurotomy methods typically use a single RF probe generating a generally oval or oblate spheroid lesion. The RF probe is positioned in an attempt to include the target nerve within the oval or oblate spheroid lesion. In various procedures, access to a target nerve may be limited (e.g., limited to a restricted angular range), thereby raising significant challenges to medical personnel to create sufficient lesions to provide optimal clinical outcomes. Additionally, anatomical variations of the nerve location relative to anatomical landmarks provide additional challenges.

SUMMARY OF THE INVENTION

The present invention is directed toward improved methods, systems, and related apparatuses for performing thermal ablation in general, and in particular, improved methods, systems, and related apparatuses for performing RF neurotomy, specifically in the region of the spine of a patient.

In one aspect, a needle is provided for use (e.g., insertion into a patient) during an RF ablation procedure that comprises a hub, an elongate member fixed to the hub, a tip fixed to the elongate member at a distal end thereof, and a plurality of filaments disposed within at least a portion of the elongate member. The needle may further include an actuator interconnected to the plurality of filaments, wherein the actuator may move relative to the hub so as to move the plurality of filaments relative to the tip of the needle.

In one approach, the tip and first and second ones of the plurality of filaments are operable as a single monopolar RF electrode. By way of example, in one implementation the needle may include a lumen disposed within the elongate member, wherein the lumen and tip are configured to receive an RF probe, wherein the tip and the first and second filaments may be electrically connected to the RF probe for delivery of an RF energy signal. In another implementation, an RF probe may be integrated into the needle structure for communication of an RF signal to the tip and plurality of filaments.

In another approach, the tip and the plurality of filaments may be operable in a bipolar manner. For example, the tip and/or one or more of the plurality of filaments may be electrically interconnected to an RF energy source to combinatively operate as an active RF electrode. In turn, one or a plurality of additional ones of the plurality of filaments may be electrically interconnected to combinatively function as a return RF electrode.

In a further aspect, the actuator may be operable to move the plurality of filaments relative to the tip between a retracted position and a deployed position, wherein in the deployed position the plurality of filaments extend outwardly from the tip. In this regard, each filament may comprise a distal end, wherein in a deployed position the distal ends of the filaments each define a point, and wherein the average of all the points is offset from a central longitudinal axis of the elongate member.

In one embodiment, the average of distal end points of first and second filaments may be at midpoint between such distal ends. In certain embodiments, the distal end of each of the plurality of filaments defines a vertex of a polygon, wherein an average of corresponding points is a centroid of the polygon.

In certain embodiments, a first filament and a second filament may have corresponding distal ends which, together with a distal end of the tip, define a polygon therebetween. In this regard, in various implementations the plurality of filaments may be disposed asymmetrically about a central longitudinal axis of the elongate member in their deployed position.

In another aspect, a method for performing RF neurotomy in a patient is provided (e.g., spinal RF neurotomy), and includes the steps of moving a tip of a needle to a first position proximate to a target nerve along the spine of a patient, and after achieving the first position, advancing a plurality of filaments relative to the tip to a deployed position. After such positioning, the method may include the step of applying RF energy to the tip and/or at least one of the plurality of filaments, wherein said RF energy application generates heat to ablate at least a portion of the target nerve.

In one approach, the RF energy may be applied to the needle tip and each of the plurality of filaments to yield monopolar operation. In another approach, the RF energy may be applied to the tip and/or one or more of the plurality of filaments to define an active electrode, while one or more additional one of the plurality of filaments are electrically isolated to function as a return electrode for bipolar operation.

In relation to the present invention it is recognized that, as RF energy penetrates biological tissue, protein and water molecules oscillate in response to the RF current and the tissue adjacent to the active needle tip heats secondary to ionic friction. As the tissue heats, and coagulates, the biophysical properties of the tissue change. These tissue changes limit penetration of the RF energy beyond a leading edge defined by the shape and size of the active needle tip. The size of a radiofrequency lesion using conventional needle technology is limited regardless of the duration of lesion or maximum temperature delivered.

The described invention overcomes this obstacle and expands the effective area of RF energy delivery by increasing the overall active tip surface area from which the RF energy emanates. The use of multiple filaments provides additional conduits for RF energy creating a multipolar RF field effect. The size and specific conformation of the RF lesion may be dictated by the location and orientation of the filaments, and may be beneficially modified to suit a specific anatomical application by changing the size, placement, and number of filaments.

Additional aspects and advantages of the present invention will become apparent to one skilled in the art upon consideration of the further description that follows. It should be understood that the detailed description and specific examples are intended for purposes of illustration only and are not intended to limit the scope of the invention. Furthermore, any of the above arrangements, features and/or embodiments may be combined with any of the above aspects where appropriate.

BRIEF DESCRIPTION OF THE DRAWINGS

For a more complete understanding of the present invention and further advantages thereof, reference is now made to the following Detailed Description of the Invention taken in conjunction with the accompanying drawings, wherein.

DETAILED DESCRIPTION OF THE INVENTION

In the following description, the invention is set forth in the context of apparatus and methods for performing RF ablation. More particularly, the systems and methods may be used to perform RF neurotomy to ablate portions of target nerves. Even more particularly, the systems and methods may be used to perform spinal RF neurotomy to ablate portions of target nerves along the spine of a patient to relieve pain. For example, embodiments of methods and apparatuses described herein relate to lumbar RF neurotomy to denervate a facet joint between the L4 and L5 lumbar vertebrae. Denervation is achieved by application of RF energy to a portion of a medial branch nerve to ablate or cauterize a portion of the nerve, thus interrupting the ability of the nerve to transmit signals to the central nervous system. In another example, embodiments described herein relate to sacroiliac joint RF neurotomy.

Figure 1:
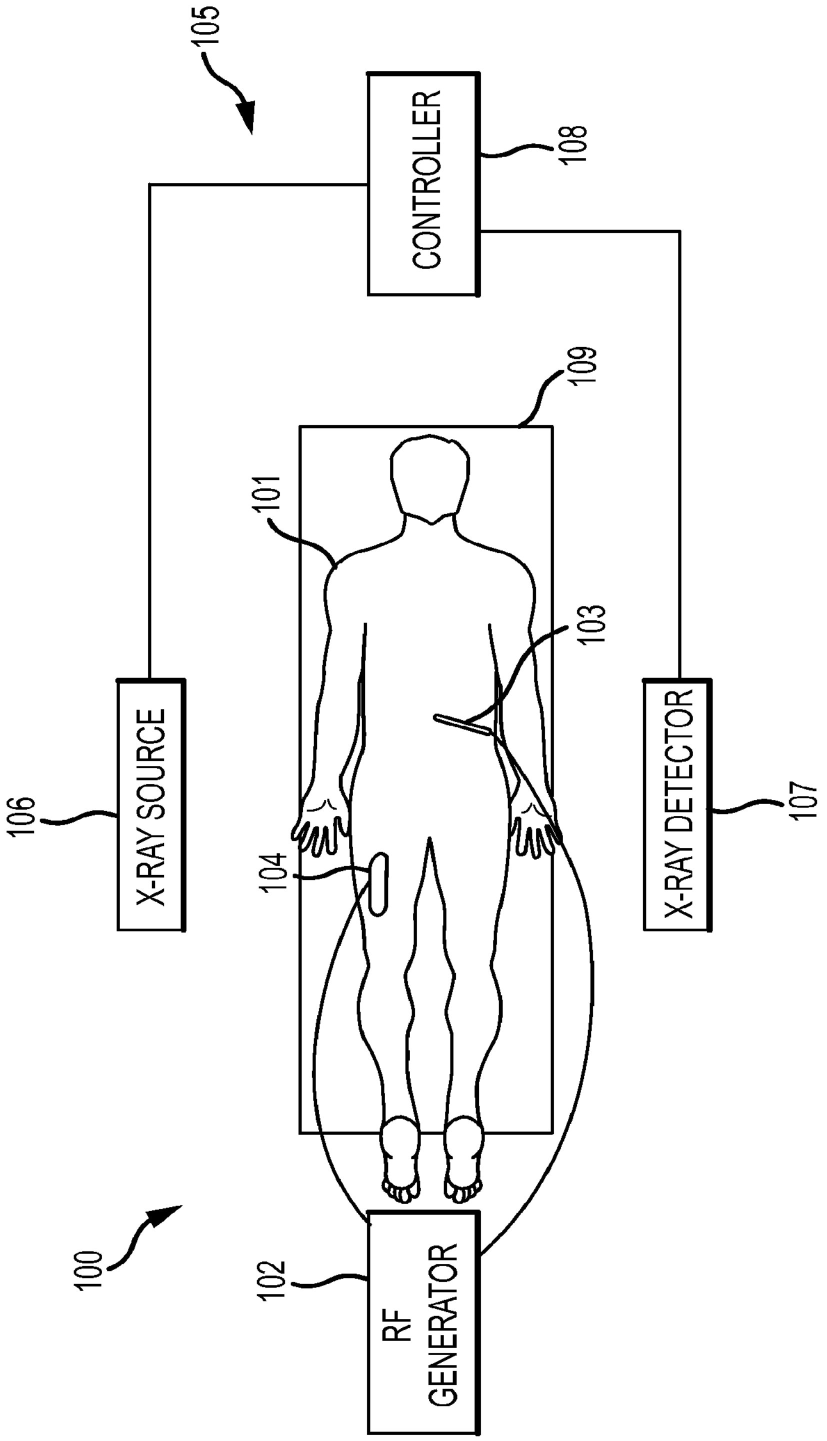
FIG. 1 is a schematic diagram of an RF neurotomy system being used to perform RF neurotomy on a patient.

FIG. 1 is an illustration of an RF neurotomy system 100 for performing RF neurotomy on a patient 101. The patient 101 may be positioned face down on a table 109 or surface to allow access along the spine of the patient 101. The table 109 may be made of radiolucent materials substantially transparent to x-rays, such as carbon fiber.

The system 100 may include an RF generator 102 capable of generating an RF energy signal sufficient to ablate target tissue (e.g. cause lesions in targeted volumes; cauterize targeted portions of target nerves). The RF generator 102 may, for example, be capable of delivering RF energy of about 460,000-500,000 Hz. A needle 103 capable of conducting (e.g., transmitting or directing) RF energy may be interconnected to the RF generator 102 and may be used to deliver an RF energy signal to a specific site within the patient 101. Where the needle 103 is a monopolar device, a return electrode pad 104 may be attached to the patient 101 to complete a circuit from the RF generator 102, through the needle 103, through a portion of the patient 101, and back to the RF generator 102 through the return electrode pad 104. In other bipolar arrangements the needle 103 may comprise at least one supply electrode and at least one return electrode to define the circuit.

The RF generator 102 may be operable to control the RF energy emanating from the needle 103 in a closed-loop fashion. For example, the needle 103 and/or an RF probe disposed within the needle 103 may contain a temperature measurement device, such as a thermocouple, to measure the temperature at the target tissue. Data may also be available from the RF generator 102, such as power level and/or impedance, which may also be used for closed-loop control of the needle 103.

Figure 4:
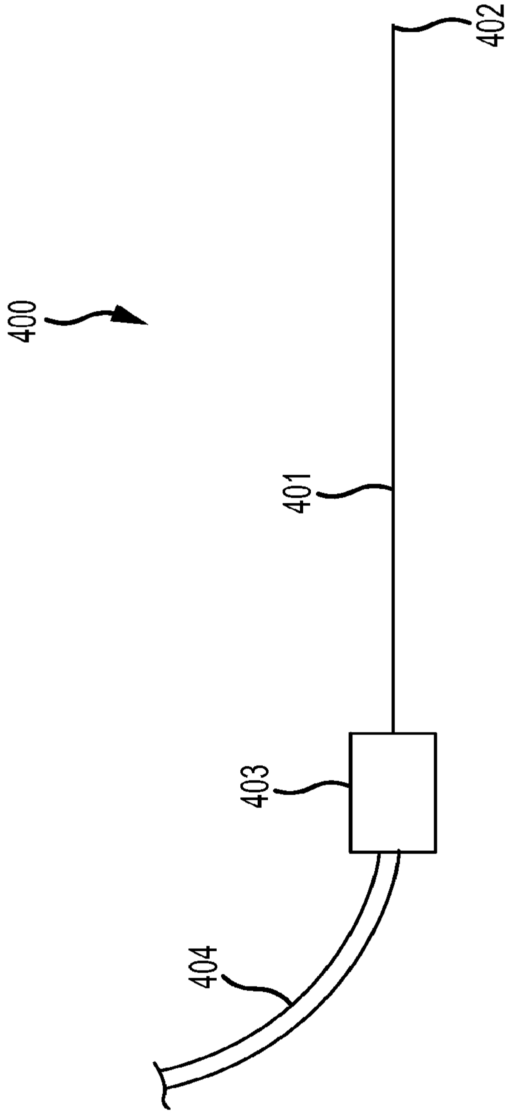
FIG. 4 is a schematic diagram of an RF probe assembly.

Turning to FIG. 4, an exemplary RF probe assembly 400 compatible with the needle 103 is illustrated. The RF probe assembly 400 includes an RF probe 401 that may be inserted into a patient (e.g., through needle 103) and may direct RF energy to the target tissue. The RF probe 401 may include a thermocouple operable to measure temperature at a distal end 402 of the RF probe 401. The RF probe assembly 400 may include a connector 403 and a cable 404 for use in connecting the RF probe 401 to the RF generator 102.

Returning to FIG. 1, the system 100 may include an imaging system 105 capable of producing internal images of the patient 101 and the needle 103 to facilitate navigation of the needle 103 during a procedure. The system 100 may further include a display for displaying the generated images to a physician performing the RF ablation procedure. In one example, the imaging system 105 may be a fluoroscope capable of generating real-time two dimensional images of the needle 103 and internal structures of the patient 101. As such, the imaging system may include an X-ray source 106, an X-ray detector 107 and a controller 108. The X-ray source 106 and X-ray detector 107 may be mounted on a movable structure (e.g., a C-arm), to facilitate capturing a variety of images of the patient 101 (e.g., at various angles or projection views). Alternatively, the imaging system 105 may be any other appropriate imaging system, such as, for example, a computed tomography (CT) scanner.

Figure 2A:
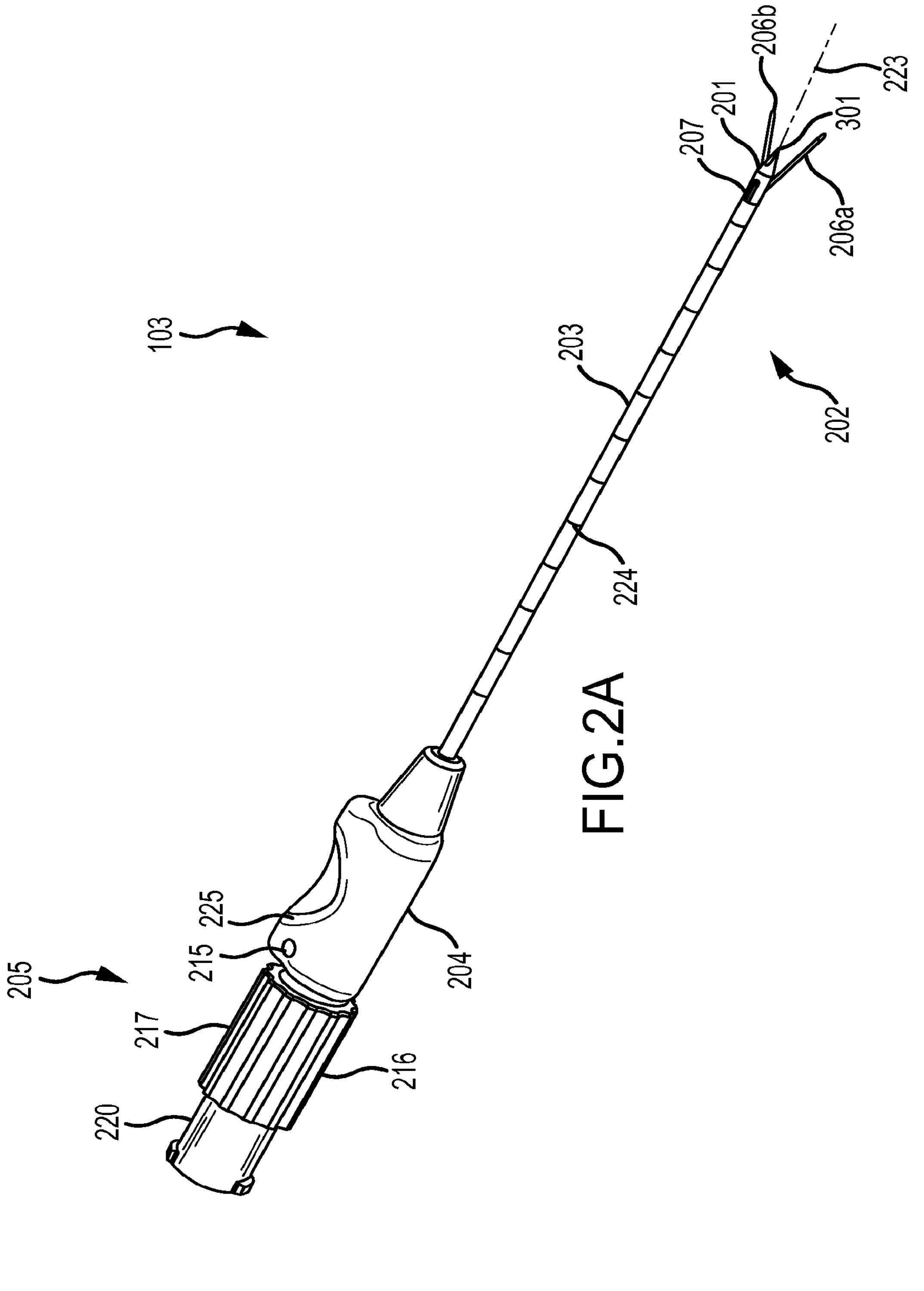
FIG. 2A is a perspective view of a needle that may be used in an RF neurotomy procedure.
Figure 2B:
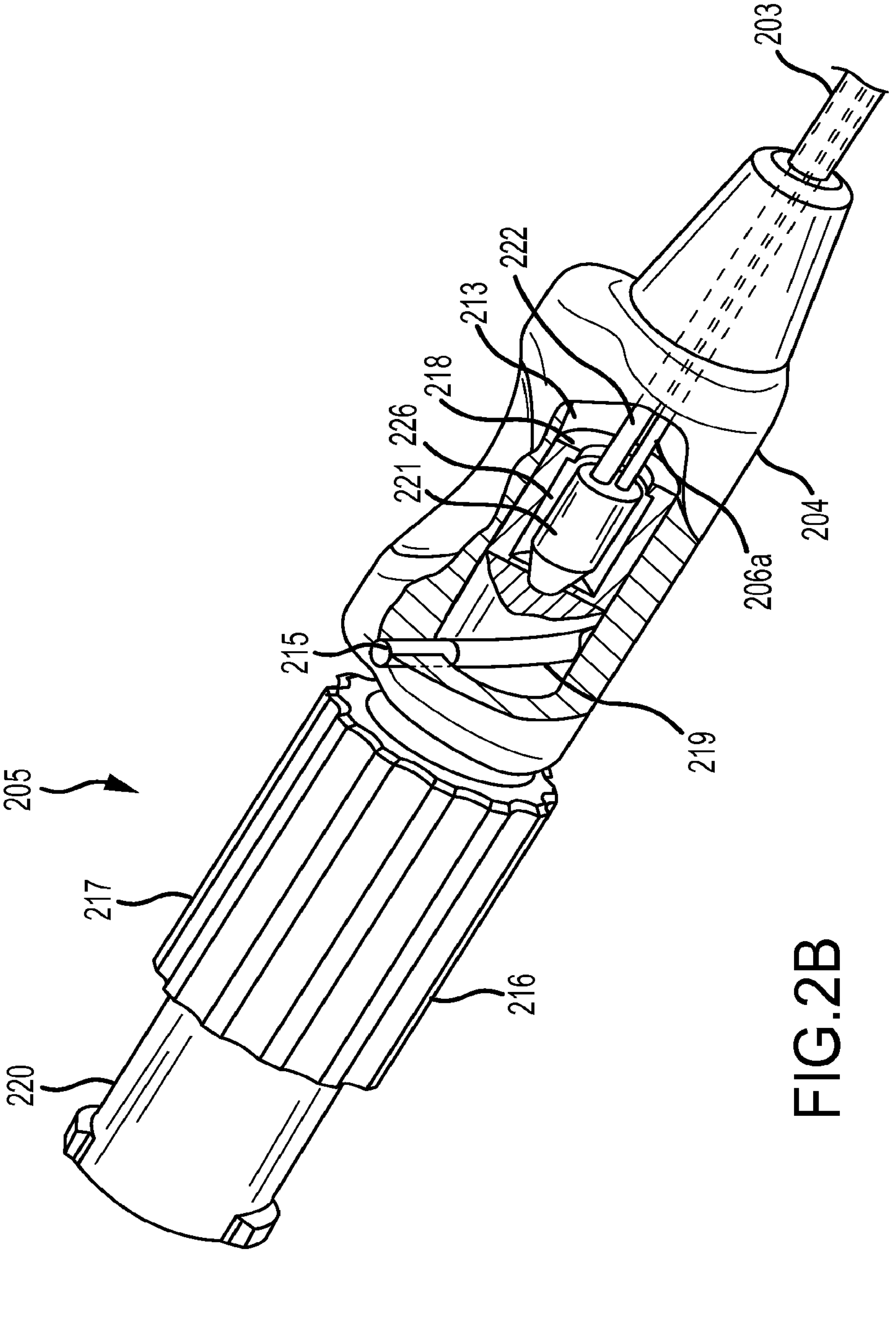
FIG. 2B is a cut away perspective view of a portion of the needle of FIG. 2A.

FIG. 2A is a detailed view of the needle 103 of the system 100 for performing RF neurotomy. The needle 103 may include a tip 201 that tapers to a point 301 capable of piercing the skin of a patient. The needle 103 may further include an elongate member 203 connected to the tip 201 at a distal end 202 of the needle 103 and connected to a hub 204 at a proximal end 205 of the needle 103. The needle 103 includes a central longitudinal axis 223 that is disposed along the center of the elongate member 203.

The needle 103 may include a self-contained mechanical mechanism, in the form of deployable filaments 206*a*, 206*b*, operable to expand the volume of effective RF energy delivery as compared to known single-electrode RF probes. The filaments 206*a*, 206*b* may be at least partially disposed within the elongate member 203 and may be operable to emerge through a side wall of the needle 103 proximate to the distal end 202 of the needle 103. Alternatively, the needle 103 may include a single filament or three or more filaments. The filaments 206*a*, 206*b* allow offsetting and/or contouring of the lesion geometry produced using the needle 103 to match a desired target volume. The filaments 206*a*, 206*b* may be deployable and/or retractable by moving an actuator 216 relative to the hub 204.

As will be further described, the needle 103 may further include a tube 207 that includes a lumen therethrough. The lumen may be used to transport fluids to and/or from the target volume. The lumen may also accept the RF probe 401 for delivery of RF energy to the target volume. In an alternate embodiment, the RF probe 401 may be integrated into the needle 103. In such an embodiment, the tube 207 need not be present for RF energy delivery, although it may be included to facilitate fluid delivery. The filaments 206*a*, 206*b* may include lumens therethrough for the transportation of fluid to and/or from the target volume. The filaments 206*a*, 206*b* may function as thermocouples.

As RF energy penetrates biological tissue, protein and water molecules oscillate in response to the RF current and the tissue adjacent to the RF electrode is heated. As the tissue heats and coagulates, the biophysical properties of the tissue change. These tissue changes limit penetration of the RF energy beyond a leading edge defined by the shape and size of an active needle tip. Accordingly, the size of a radiofrequency lesion using conventional single needle technology is thus practically limited after achievement of a certain temperature delivered for a certain time.

The needle 103 with deployable filaments 206*a*, 206*b* overcomes this obstacle and expands the effective area of RF energy delivery by providing multiple locations (e.g., tip 201 and filaments 206*a*, 206*b*) from which the RF energy emanates. The use of multiple filaments 206*a*, 206*b* provides additional conduits for RF energy creating a multiple electrode RF field effect. The size, shape and location of a lesion created with the needle 103 may be established by the quantity, location and orientation of the filaments, and may be beneficially modified to suit a specific anatomical application by changing various aspects of the filaments as discussed below.

Where it is desired to create a lesion offset from the central longitudinal axis 223, the lesion may be preferentially offset in a desired direction from the central longitudinal axis 223 by rotationally orienting the needle 103. Moreover, the needle 103 may be used to create a lesion offset from the central longitudinal axis 223 in a first direction. Then, the filaments 206*a*, 206*b* may be retracted, the needle 103 rotated, and the filaments 206*a*, 206*b* redeployed to create a lesion offset from the central longitudinal axis 223 in a second direction.

Figure 3A:
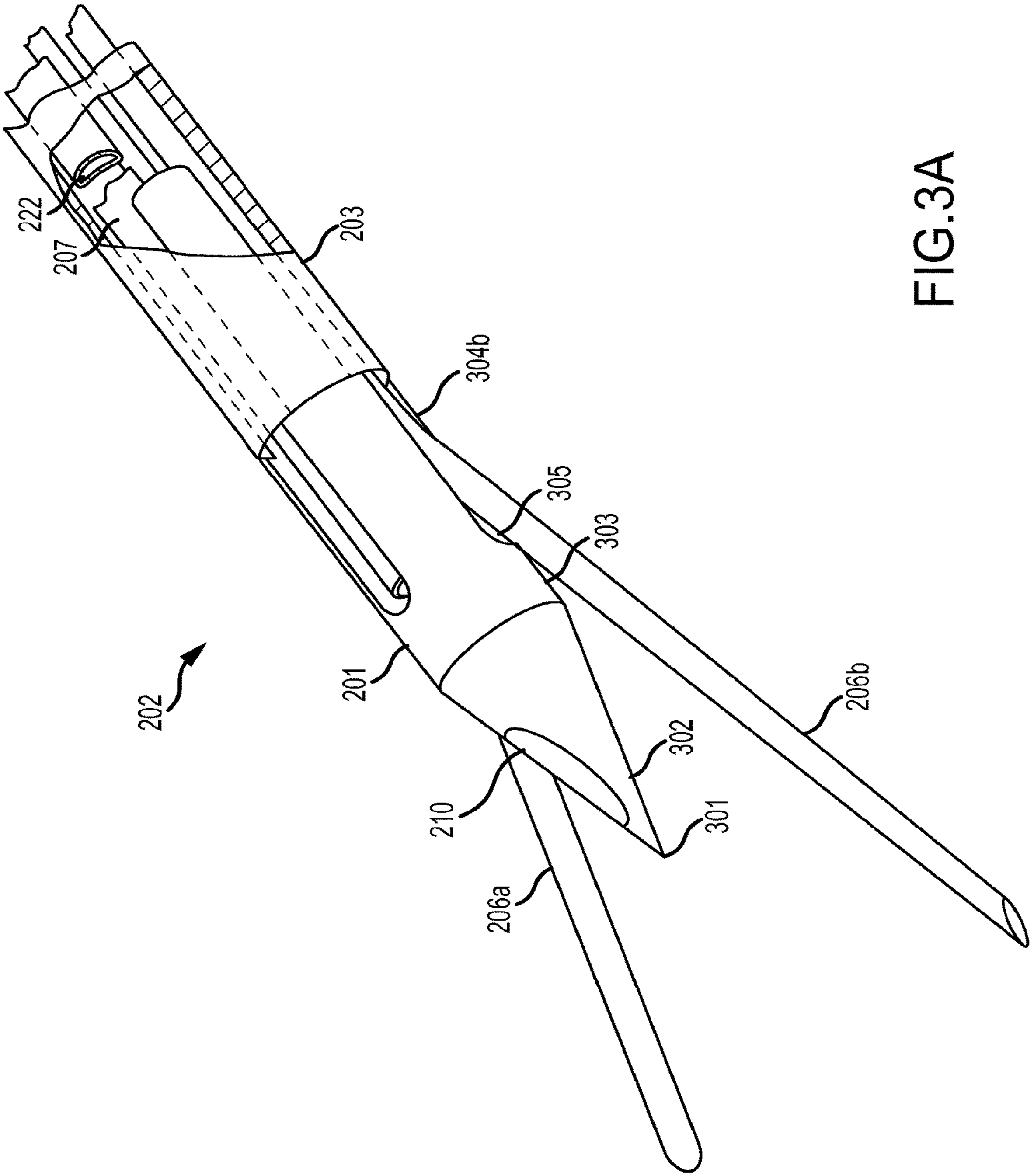
FIG. 3A is a detailed view of a tip of the needle of FIG. 2A with filaments disposed in a fully deployed position.
Figure 3B:
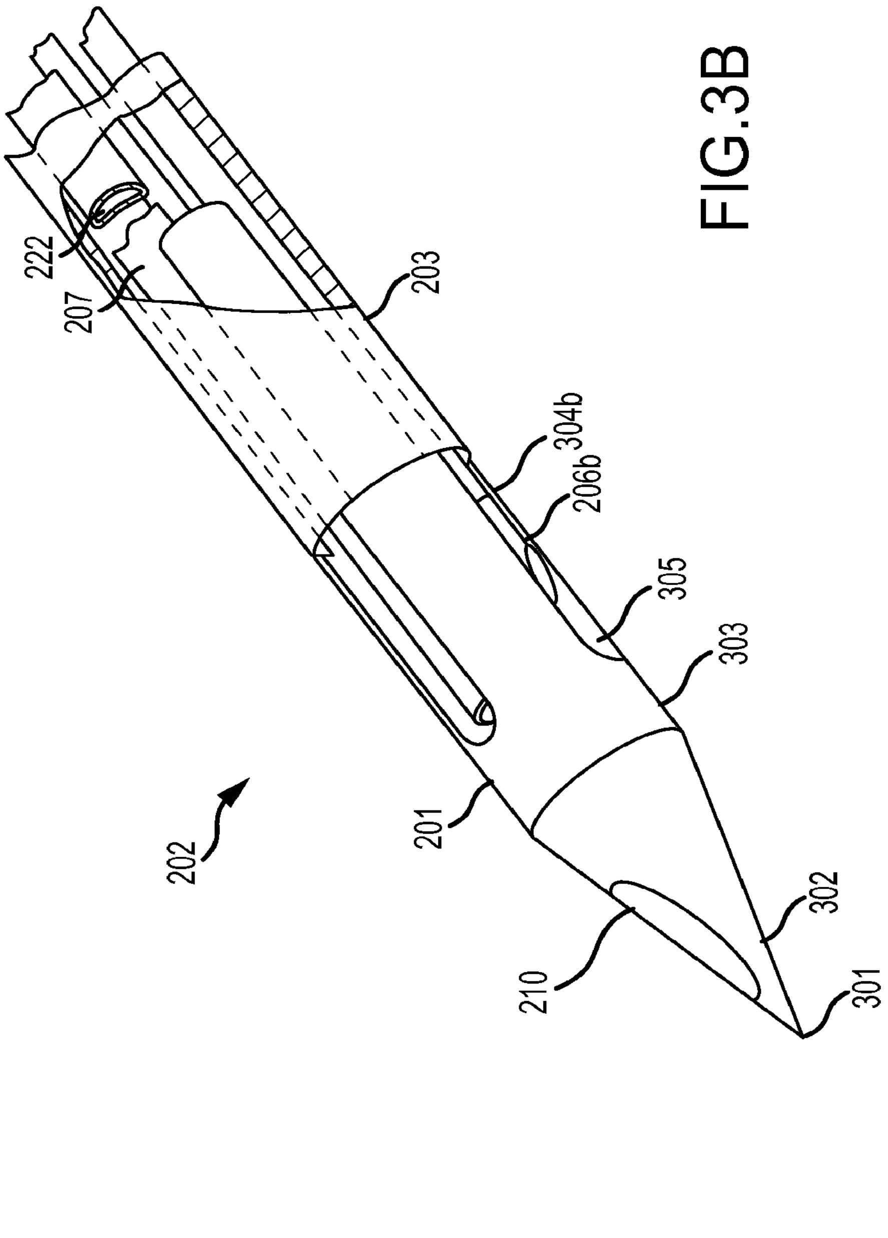
FIG. 3B is a detailed view of a tip of the needle of FIG. 2A with filaments disposed in a retracted position.

FIGS. 3A and 3B are detailed views of the distal end 202 of the needle 103 that includes the tip 201. The tip 201 may include the sharpened point 301 for piercing the skin of a patient and facilitating advancement through tissue. The tip 201 may further include a tapered portion 302 that transitions the tip 201 from the point 301 to a body portion 303. The body portion 303 is the portion of the tip 201 that is disposed proximal to the tapered portion 302. The body portion 303 may be cylindrical as illustrated, or it may be of any other appropriate shape. The body portion 303 may have a cross-section that coincides with the cross section of the elongate member 203.

The tip 201 may act as an RF energy delivery element. As such, the tip 201 may be made from a conductive material such as, for example, stainless steel. The tip 201 may be coated. The tip 201 material and optional coating may be selected to improve radiopacity, improve and/or alter RF energy conduction, improve lubricity and/or reduce tissue adhesion.

The tip 201 may include filament port or slot 304*a* (not visible in the views of FIGS. 3A and 3B) and filament port or slot 304*b*. The geometry of the filament slots 304*a*, 304*b* may be selected to allow filaments 206*a*, 206*b* to be adequately retracted (e.g., such that they are disposed within a cross-sectional envelope of the body portion 303 of the tip 201) while the needle 103 is inserted into the body, so that the filaments 206*a*, 206*b* do not cause any unintended damage to the patient. Such positioning of the filament slots 304*a*, 304*b* avoids having filament exit features on the tapered portion 302 and thus avoids potential coring that could be caused by such positioning.

Figure 10:
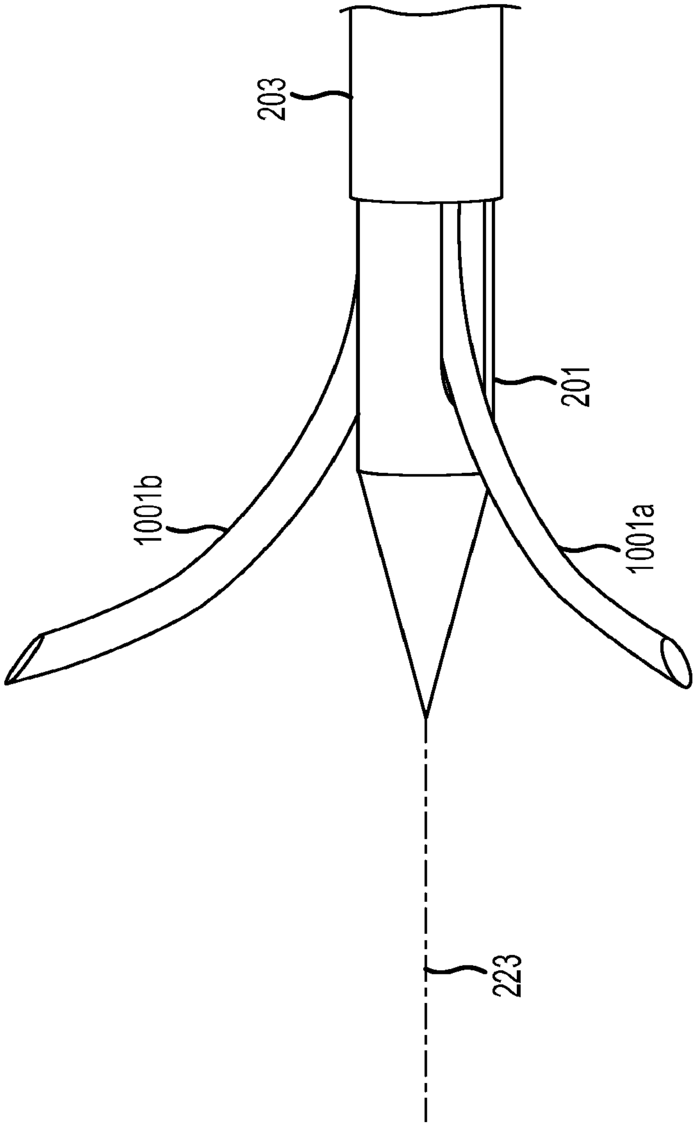
FIG. 10 is a side view of another alternate embodiment of the needle of FIG. 2A.

The internal geometry of the filament slots 304*a*, 304*b* may be designed such that the filaments 206*a*, 206*b* may be easily retracted and advanced. For example, the internal geometry of the filament slots 304*a*, 304*b* may include a transition region 305 that meets the outer surface of the body portion 303 at an angle of about 30 degrees. The transition region 305 may, for example, be curved or planar. Thus, when the filaments 206*a*, 206*b* are in the form of a member without a pre-set bias (e.g., substantially straight), advancement of the filaments 206*a*, 206*b* relative to the filament slots 304*a*, 304*b*, will cause the filaments 206*a*, 206*b* to be deflected outwardly as the filaments 206*a*, 206*b* move distally along the transition region 305. Depending on the positioning of the transition region 305 relative to where the filaments 206*a*, 206*b* are confined (e.g., in the needle 103 of FIG. 3A the filaments 206*a*, 206*b* are confined to only longitudinal movement where they enter into the elongate member 203) and on the mechanical properties of the filaments 206*a*, 206*b*, various deployment angles of the filaments 206*a*, 206*b* relative to the central longitudinal axis 223 may be achieved. Generally, the portions of the filaments 206*a*, 206*b* that extend outwardly away from the filament slots 304*a*, 304*b* may be unrestrained and thus may take any appropriate form. For example, where there is no pre-set bias, the portions of the filaments that extend outwardly away from the filament slots (and therefore from the tip) may be substantially straight, such as shown in FIGS. 2A, 3A, 3C, 6, 11A-11C and 14. Where a pre-set bias is present, the portions of the filaments that extend outwardly away from the filament slots may take any appropriate shape, such as, for example, curved as shown in FIG. 10.

The radial orientation of the filament slots 304*a*, 304*b* may be selected such that a center point between the filament slots 304*a*, 304*b* does not coincide with the central longitudinal axis 223. For example, as shown in FIGS. 2A, 3A and 3B, the filament slots 304*a*, 304*b* may be positioned such that they are about 120 degrees apart about the circumference of the tip 201. Other filament slot configurations may be configured to achieve the filament placements discussed below. These configurations may be achieved by varying the quantity of filament slots, the placement of filament slots about the circumference of the tip 201, and/or the placement of filament slots along the center longitudinal axis 223 to achieve the filament placements discussed below.

As noted above, and illustrated in FIGS. 3A and 3B, the needle 103 may comprise a tube 207 that includes a lumen 222 therethrough. The lumen 222 may be employed to accept the RF probe 40 for delivery of RF energy and/or for the transport of fluids. In this regard, the tip 201 may further include a fluid port 210 that may be in fluid communication via a channel through the tip 201 with the lumen 222. The fluid port 210 may be centrally located or it may be located offset from the center longitudinal axis 223 as shown in FIGS. 2A and 3A. The fluid port 210 may be used to transfer fluid between the region of the tip 201 and the proximal end 205 of the needle 103. For example, during an RF neurotomy procedure, an anesthetic and/or an image enhancing dye may be introduced into the region of tissue around the tip 201 through the fluid port 210. In an alternate embodiment, the fluid port 210 may be located along the body portion 303 of the tip 201.

As may be appreciated, the channel through the tip 201 may be sized to accommodate a tip of the RF probe 401 that may be inserted into the needle 103. The channel may be sized such that RF energy from the inserted RF probe 401 is satisfactorily passed from the RF probe 401 to the tip 201 and filaments 206*a*, 206*b*.

The elongate member 203 may be in the form of a hollow tube (e.g., sheath, cannula) interconnecting the tip 201 with the hub 204. The elongate member 203 may be configured with adequate strength to allow the needle 103 to pierce the patient's skin and advance to a target area through various tissue types, including, for example, fat and muscle tissue. The elongate member 203 may also be capable of resisting kinking as it is advanced. In an alternate embodiment, the elongate member 203 may be a rod with a plurality of lumens along its length to accommodate filaments 206*a*, 206*b*, the RF probe 401, and/or a fluid passage.

The elongate member 203 houses portions of the filaments 206*a*, 206*b* and the tube 207, and allows for relative movement of the filaments 206*a*, 206*b*. The elongate member 203 may be of any appropriate size and internal configuration to allow insertion into the patient 101 and to house componentry therein. In an exemplary embodiment, the elongate member 203 may, for example, be a 16 gauge round tube or smaller. For example, the elongate member 203 may be 18 or 20 gauge. For example, the elongate member may have a maximum cross dimension of at most about 1.7 mm. In another example, the elongate member may have a maximum cross dimension of at most about 1 mm. The elongate member 203 may have a length selected for performing a specific spinal RF neurotomy procedure on a particular patient. The elongate member 203 may be constructed from an insulative material to reduce the amount of RF energy emitted along the length of the elongate member 203 when the RF probe 401 is disposed therein. For example, the elongate member 203 may be constructed from polymeric, ceramic or other insulative material. The elongate member 203 may include a coating that may improve radiopacity to aid in visualization of the position of the needle 103 using fluoroscopy. The elongate member 203 may include a coating to improve its insulative properties. The elongate member 203 may include a lubricious coating to improve its ability to be inserted and positioned within the patient and to reduce tissue adhesion. The elongate member 203 may include markers 224 along its length to assist in determining the depth to which the needle 103 has entered into the anatomy. Such markers 224 may be radiopaque so that they may be viewed under fluoroscopy. A collar (not shown) may be disposed about the elongate member 203 to assist in placement of the tip 201 of the needle 103. For example, the tip 201 may be positioned in a first position, the collar may then be placed against the patient's 101 skin, and then the needle 103 may be withdrawn a certain distance. Such a distance will be indicated by the distance between the collar and the patient's 101 skin.

The elongate member 203 may be fixedly interconnected to the tip 201 and hub 204 in any appropriate manner. For example, the tip 201 may be press fit into the elongate member 203 and the elongate member 203 may be press fit into the hub 204. Other possible methods of attachment include adhesive bonding and welding. In an alternate embodiment, the elongate member 203 and the tip 201 may be a single unitary structure. The elongate member 203 may be steerable and incorporate controlling mechanisms allowing the elongate member 203 to be deflected or steered after insertion into the anatomy.

The tube 207 containing the lumen 222 may be constructed from any appropriate material. For example, the tube 207 may be constructed from a conductive material, such as stainless steel, such that when the RF probe 401 is inserted within the tube 207, the RF energy emitted by the RF probe 401 may be conducted through the tube 207 and into and through the tip 201 and filaments 206A, 206*b*. The tube 207 may be interconnected to the tip 201 such that the lumen 222 is in sealed, fluid communication with the channel through the tip 201. This may be accomplished by a press fit, weld, or any other appropriate method.

As noted, the lumen 222 may be in fluid communication with the tip 201 at the distal end 202. A proximal end of the lumen 222 may be disposed at the proximal end 205 of the needle 103. In this regard, the lumen 222 may run from the distal end 202 to the proximal end 205 with the only access being at the distal and proximal ends. Furthermore, the lumen 222 may be the only lumen of the needle 103 disposed along the elongate member 103.

Accordingly, the RF probe 401 inserted into the lumen 222 may be positioned such that an end of the RF probe 401 is proximate the tip 201. For example, the RF probe 401 may be positioned such that the distal end 402 of the RF probe 401 is in the lumen 222 near the tip 201 or in the channel through the tip 201. Thus, RF energy transmitted through the RF probe 401 may be conducted by the tip 201 and filaments 206*a*, 206*b*. The size of the lumen 222 may be selected to accommodate a particular size of RF probe 401. For example, for a 22 gauge RF probe 401, at least a 21 gauge or larger lumen 222 may be employed. For example, the lumen 222 may have a maximum cross-dimension of less than about 0.85 mm.

The proximal end of the tube 207 may be operable to receive the RF probe 401. Moreover, the proximal end of the tube 207 and the actuator 216 may be configured to accept a connector, such as a Luer fitting, such that a fluid source may be connected to the tube 207.

As illustrated in FIGS. 2A and 3A, the needle 103 includes two filaments 206*a*, 206*b* disposed within and along elongate member 203. Distal ends of the filaments 206*a*, 206*b* are disposed proximate to the tip 201 and proximal ends of the filaments 206*a*, 206*b* are fixed to a filament hub 221 discussed below. The filaments 206*a*, 206*b* are movable along the central longitudinal axis 223 between a fully deployed position as illustrated in FIGS. 2A and 3A and a retracted position illustrated in FIG. 3B. Moving the filaments 206*a*, 206*b* distally from the retracted position moves the filaments 206*a*, 206*b* toward the fully deployed position, while moving the filaments 206*a*, 206*b* proximally from the deployed position moves the filaments 206*a*, 206*b* toward the retracted position. The filaments 206*a*, 206*b* may be deployed in intermediate positions between the fully deployed positions and the retracted positions.

In the fully deployed position as shown in FIG. 3A, the distal ends of the filaments 206*a*, 206*b* are disposed away from the tip 201. In the refracted position as shown in FIG. 3B, the distal ends of the filaments 206*a*, 206*b* are disposed entirely within an outer perimeter (e.g., circumference where the non-tapered portion 303 of the tip 201 is round) of the tip 201. In the deployed position, the filaments 206*a*, 206*b* act as broadcast antennae for the RF probe 401 (e.g., RF energy passes from the RF probe 401 to tip 201 and filaments 206*a*, 206*b*, and into a target volume within the patient 101). In this regard, together, the RF probe 401 inserted into the lumen 222, the tip 201, and the filaments 206*a*, 206*b*, may form a monopolar electrode for application of RF energy to the target volume. The filaments 206*a*, 206*b* allow the RF energy from the RF probe 401 to be dispersed over a larger volume than would be possible with the tip 201 alone.

The filaments 206*a*, 206*b* may be constructed from a material operable to conduct RF energy, e.g., a metal such as stainless steel, Nitinol or shape memory alloy. The filaments 206*a*, 206*b* may be coated to enhance their ability to conduct RF energy. The filaments 206*a*, 206*b* may include a lubricious coating to aid in insertion and/or reduce tissue adhesion. The distal ends of the filaments 206*a*, 206*b* may be shaped (e.g., pointed) to improve their ability to move through tissue.

Figure 5:
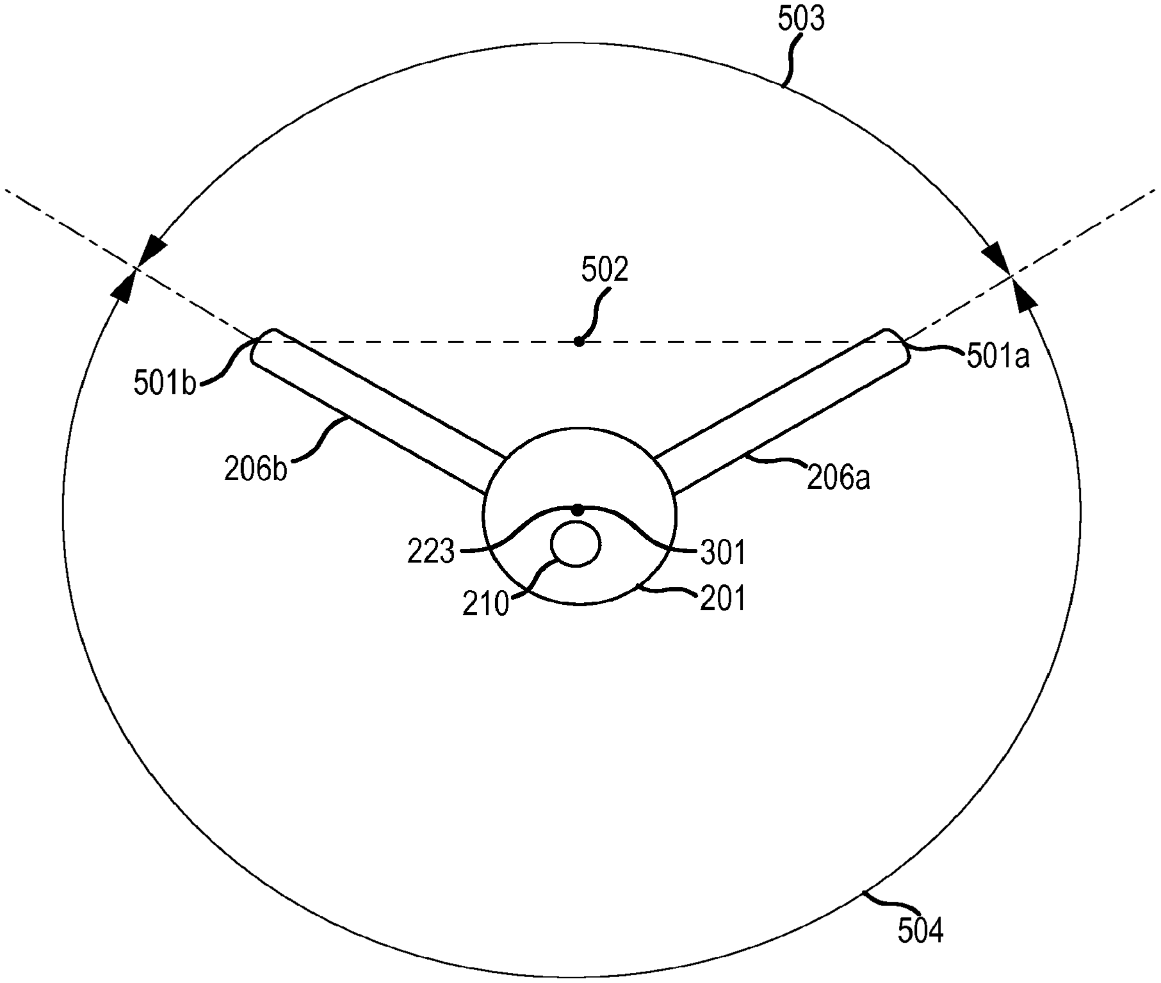
FIG. 5 is an end view of the needle of FIG. 2A.

The positioning of the filaments 206*a*, 206*b* of the embodiment illustrated in FIGS. 2A and 3A will now be described in relation to FIG. 5. FIG. 5 is an end view of the tip 201 and deployed filaments 206*a*, 206*b* of the embodiment illustrated in FIGS. 2A and 3A. The filaments 206*a*, 206*b* are positioned at a filament angle 503 of about 120 degrees apart from each other about the central longitudinal axis 223. This coincides with the positions of the filament slots 304*a*, 304*b* discussed above since the filaments 206*a*, 206*b* emerge from the filament slots 304*a*, 304*b*. Accordingly, a filament-free angle 504 of about 240 degrees is defined as the largest angle about the circumference of the tip 201 that is free of filaments 206*a*, 206*b*. In an embodiment consisting of two filaments, the filament angle 503 may be less than 180 degrees and the filament-free angle 504 may be correspondingly greater than 180 degrees (e.g., greater than 200 degrees or greater than 240 degrees).

In FIG. 5, the central longitudinal axis 223 is perpendicular to the plane of the illustration. A midpoint 502 is defined between distal ends 501*a*, 501*b* of the filaments 206*a*, 206*b*, respectively. The midpoint 502 is offset from the central longitudinal axis 223. For example, in an embodiment, the midpoint 502 may be offset from the central longitudinal axis 223 by about 2 mm. Accordingly, when RF energy is transmitted from the tip 201 and filaments 206*a*, 206*b*, it will be transmitted asymmetrically with respect to the central longitudinal axis 223 as energy will be emitted from the tip 201 and the filaments 206*a*, 206*b*. As oriented in FIG. 5, the energy will be biased in an upward direction in the direction from the point 301 toward the midpoint 502. Thus, when RF energy is transmitted during an RF neurotomy procedure, a lesion will be created that is correspondingly offset from the central longitudinal axis 223 in the direction from the point 301 toward the midpoint 502.

Figure 6:
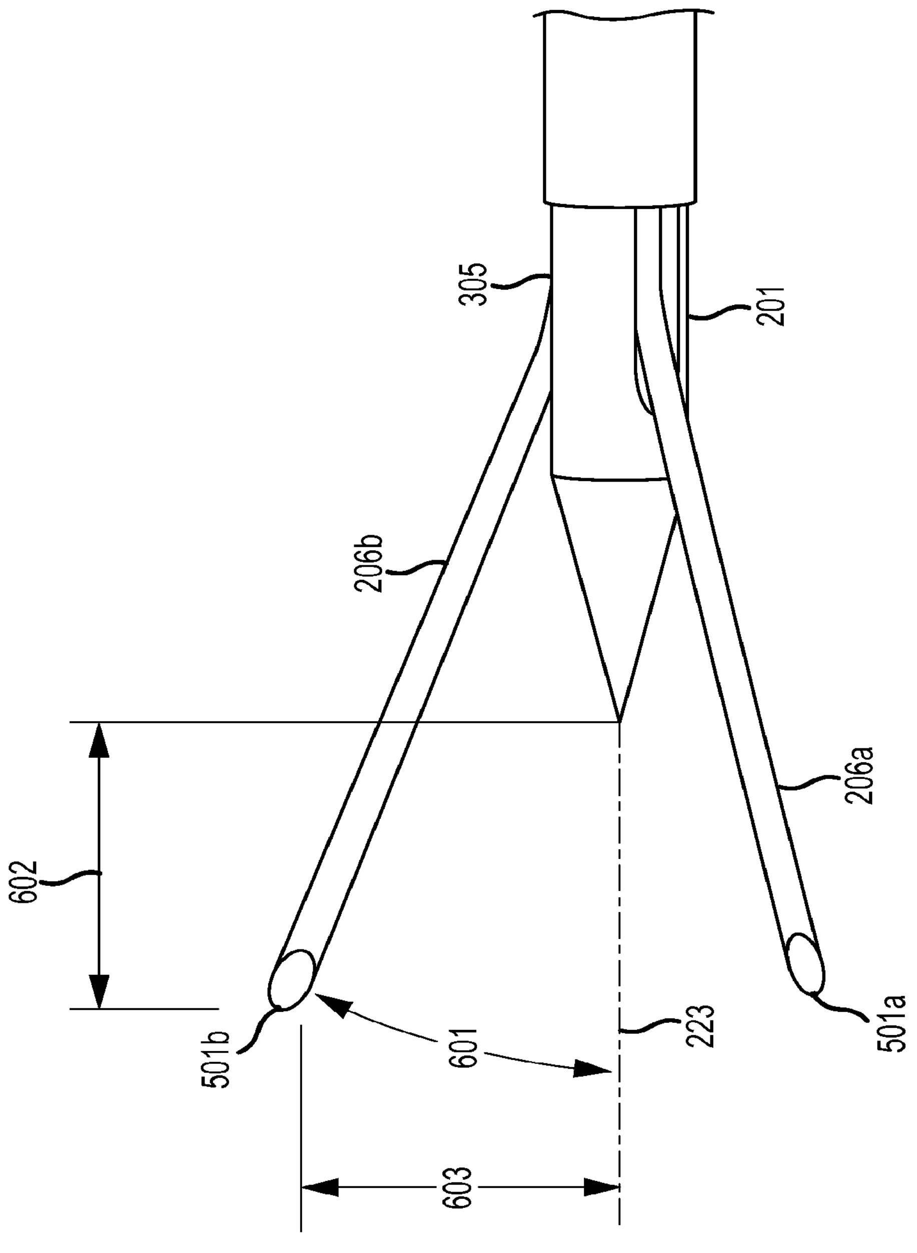
FIG. 6 is a side view of the tip of the needle of FIG. 2A.

FIG. 6 is a side view of the tip 201 and filaments 206*a*, 206*b* oriented such that deployed filament 206*b* is disposed entirely within the plane of the figure. The filaments 206*a*, 206*b* extend from the tip 201 at a common distance, or location, along the central longitudinal axis 223. The filament 206*b* is deflected radially outwardly from the central longitudinal axis 223. The filament 206*b* emerges from the tip 201 at an angle 601 of about degrees as dictated by the positioning of the transition region 305 relative to where the filament 206*b* is confined and on the mechanical properties of the filament 206*b* (as previously discussed). Also, it is noted that the distal tips 501*a*, 501*b* are positioned distally beyond the point 301 by a distance 602 and are disposed at a distance 603 from the central longitudinal axis 223. In the embodiment illustrated in FIG. 6, the distance 602 may be about 3.5 mm and the distance 603 may be about 3 mm. Such an arrangement may distally offset a lesion created by the needle 103 as compared to a lesion created with a tip without filaments or a lesion created with the needle 103 with the filaments 206*a*, 206*b* in the retracted position.

Accordingly, the filament 206*a*, 206*b* arrangement illustrated in FIGS. 2A, 3A, 3B, 5 and 6 may be operable to produce lesions that are radially offset from the central longitudinal axis 223 and distally offset from the point 301 as compared to a lesion created by the tip 201 without the filaments or a lesion created with the needle 103 with the filaments 206*a*, 206*b* in the retracted position.

Variations of filament positions and configurations from those illustrated in FIGS. 2A, 3A, 3B, 5 and 6 will now be addressed. Variations in the relative shapes, positions and sizes of lesions created with the needle 103 may be achieved by repositioning the filaments. For example, as noted above, the lesion produced by the needle 103 will be in different positions depending on whether the filaments are in the deployed or refracted positions. Accordingly, intermediately shaped, positioned and/or sized lesions may be achieved by positioning the filaments in intermediate positions between the fully deployed or refracted positions. Thus, for any given configuration of deployable filaments discussed herein, the positions and/or sizes of lesions created by those configurations may be varied by varying the positioning of the filaments to intermediate positions between the fully deployed and retracted positions. As noted above, the needle 103 with deployed filaments is operable to produce larger lesion volumes than the needle 103 with retracted filaments. For example, the needle 103 with fully deployed filaments may be operable to produce lesion volumes of about 500 $mm^3$.

Further variation in the shape, position and/or size of lesions created by needles with deployable filaments may be achieved by different configurations of filaments. Variations may include variations in materials, the number of filaments, the radial positioning of the filaments, the axial positioning of the filaments, the length of the filaments, the angle at which the filaments exit the tip, and the shape of the filaments. By varying these parameters the needle may be configured to produce lesions of various sizes and shapes that are positioned at various locations relative to the tip. Such variations may be specifically tailored to be used in specific procedures, such as RF neurotomy procedures of particular nerves adjacent to particular vertebrae.

Variations of the materials used for the tip and/or the filaments may be selected to achieve particular lesion sizes, positions and/or shapes. For example, the tip may be made form a material that does not conduct RF energy. In such an embodiment, RF energy from the RF probe 401 may be conducted by substantially only the deployed filaments. Such an arrangement may provide for a lesion with a larger offset from the central longitudinal axis 223 than would be produced where the tip conducts RF energy and acts as an electrode along with the filaments.

Another material-related variation that may affect lesion shape, size and/or position is the addition and placement of insulation over the tip and/or filaments. For example, by placing a layer of insulation over the proximal half of the portions of the filaments that extend from the tip when in the deployed position, the shape of the lesion may be altered since RF energy may primarily emanate from the distal, non-insulated portion of the filaments. Similarly, insulation may be added to the tip to alter the RF energy delivered from the tip.

Moreover, the materials used in making the filaments and tip may be selected based on RF conductivity. For example, by using a material for the tip that is less conductive of RF energy, the proportion of RF energy emanating from the tip as compared to that emanating from the filaments may be altered resulting in a corresponding change in lesion size, position and/or shape.

The RF needles and RF probes discussed herein may be constructed from materials that are Magnetic Resonance Imaging (MRI) compatible. As such, MRI equipment may be used to verify the positioning of such RF needles and/or monitor the progress of an ablation procedure (e.g., RF neurotomy) using such RF needles.

Figure 7:
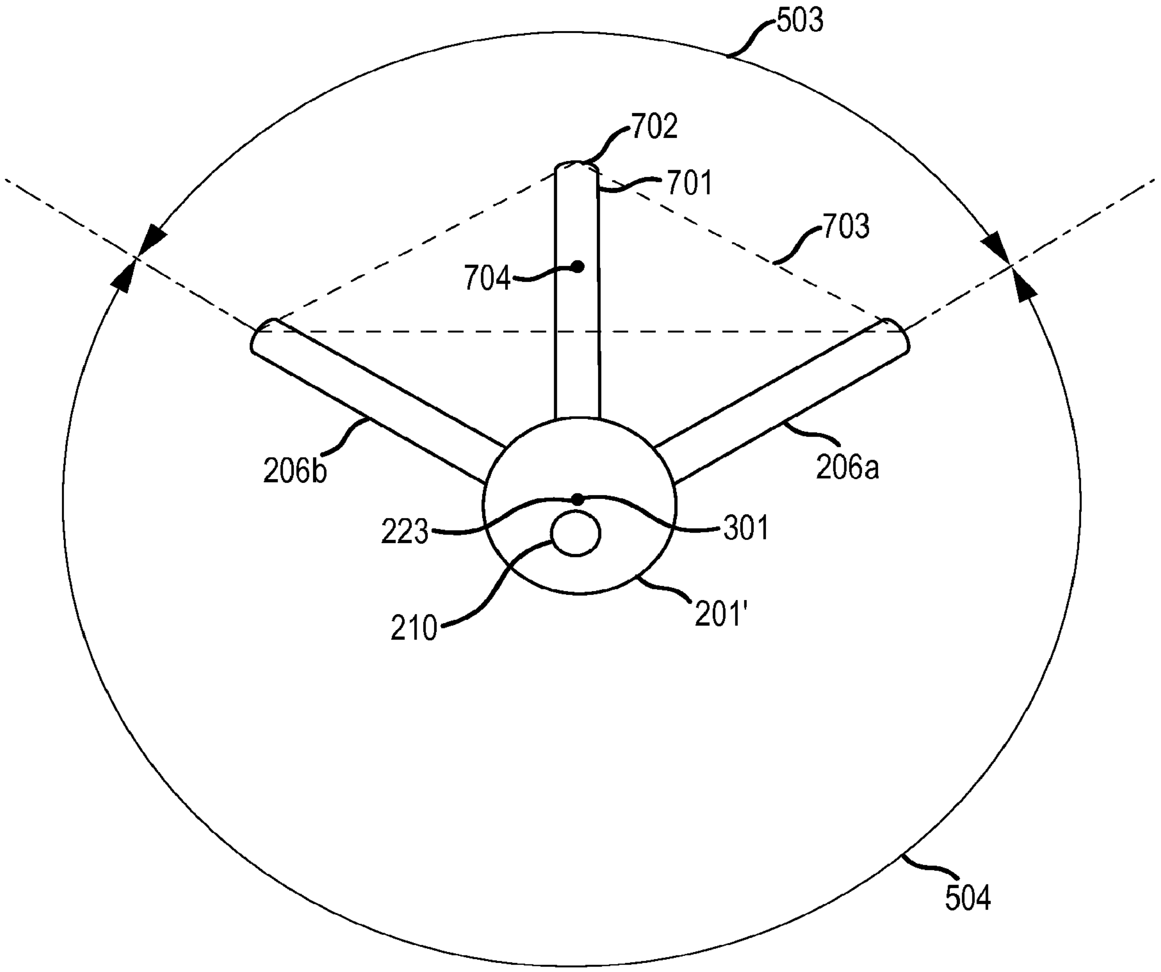
FIG. 7 is an end view of another alternate embodiment of the needle of FIG. 2A.

Variations of the number of filaments used for needle may be selected to achieve particular lesion sizes, positions and/or shapes. For example, as illustrated in FIG. 7, a third filament 701 may extend from tip 201' in a position between filaments 206*a*, 206*b*. The tips 501*a*, 501*b* of the filaments 206*a*, 206*b* and a tip 702 of filament 701 may form a polygon 703 that has a centroid 704. The centroid 704 is offset from the central longitudinal axis 223. Such an arrangement may produce a lesion that is offset from the central longitudinal axis 223 to a different degree than, and shaped differently than, a lesion created by the needle of FIG. 5. In general, where a centroid of a polygon formed by the tips of filaments (or, in the case where there are two filaments, the midpoint between them) is offset from the central longitudinal axis 223, a lesion created by such a configuration will be correspondingly offset from the central longitudinal axis 223. The filaments 206*a*, 206*b*, 702 are positioned within the same filament angle 503 of about 120 degrees as in the embodiment of FIG. 5. Furthermore, the embodiment of FIG. 7 has a filament-free angle 504 of about 240 degrees, also the same as in the embodiment of FIG. 5. In general, where the filaments are positioned within an arc that is less than 180 degrees, resultant lesions will be offset from the central longitudinal axis 223 in the direction of the filaments. In general, in an embodiment consisting of three or more filaments where the filaments are positioned within an arc that is less than 180 degrees, the filament-free angle may be correspondingly greater than 180 degrees (e.g., greater than 200 degrees or greater than 240 degrees).

Figure 8:
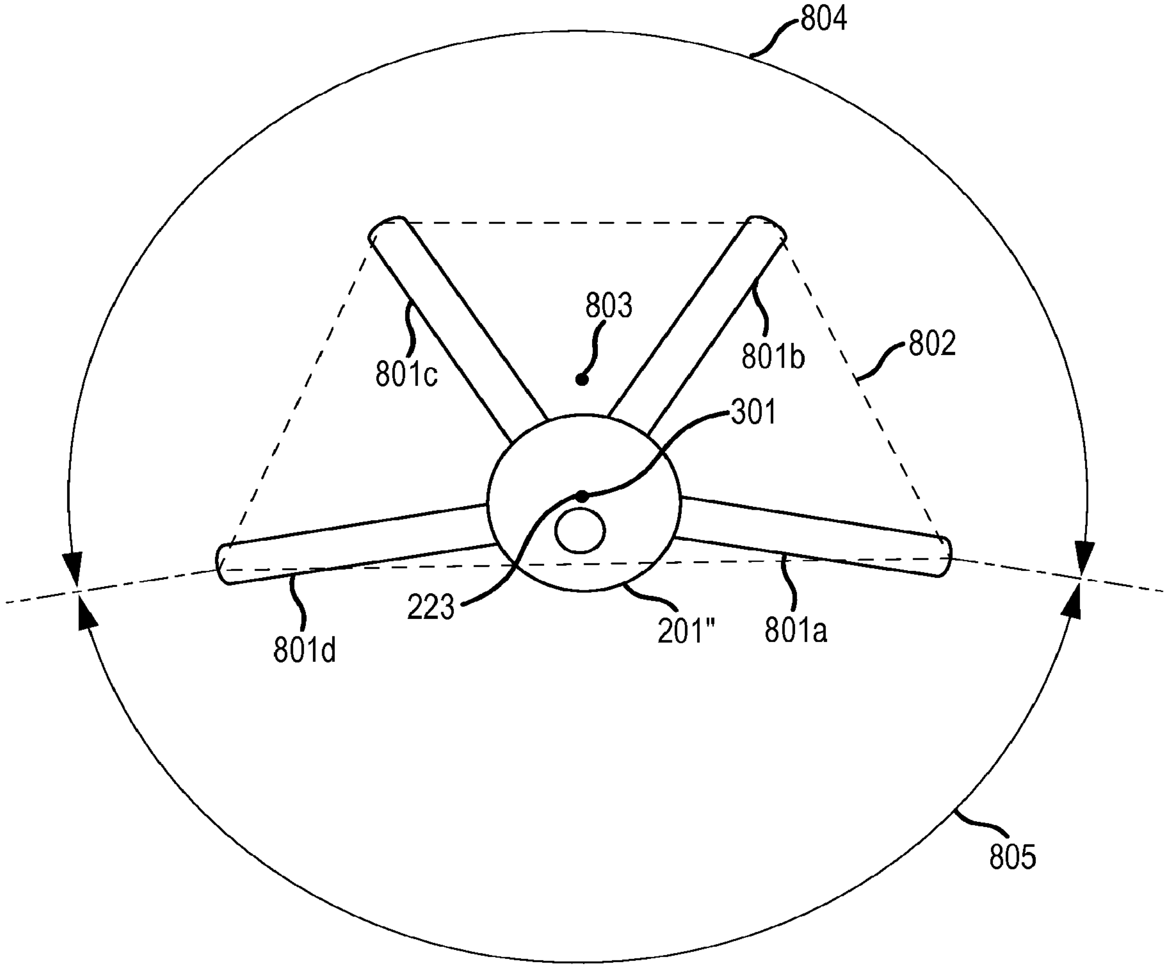
FIG. 8 is an end view of another alternate embodiment of the needle of FIG. 2A.

Variations in the radial positioning of filaments of a needle may be selected to achieve particular lesion sizes, positions and/or shapes. For example, as illustrated in FIG. 8, four filaments 801*a*-801*d* are positioned about a tip 201". The tips of the filaments 801*a*-801*d* may form a polygon 802 that has a centroid 803. Such an arrangement may produce a lesion whose center is offset from the central longitudinal axis 223 in the direction of the centroid 803. The filaments 801*a*-801*d* are positioned within a filament angle 804 of about 200 degrees. Furthermore, the embodiment of FIG. 8 has a filament-free angle 805 (i.e., the largest angle about the circumference of the tip 201" that is free of filaments) of about 160 degrees. It will be appreciated that, as illustrated in FIG. 8, a configuration capable of producing a lesion offset from the central longitudinal axis 223 may have a filament-free angle that is less than 180 degrees.

In the above-described embodiment of FIGS. 2A, 3A, 3B, 5, and 6 with two filaments, a midpoint 502 between the filaments was discussed. In embodiments with more than two filaments, a centroid of a polygon formed by the distal ends of the filaments was discussed. Both the midpoints and the centroids may be considered to be "average" points of the filaments for their particular configurations. In such embodiments, the midpoint between filaments in two-filament embodiments and the centroid of the polygon in embodiments with more than two filaments may be offset from the central longitudinal axis of the elongate member. For example, the midpoint or centroid may be offset from the central longitudinal axis by 1 mm or more. In embodiments, the polygon may lie in a plane perpendicular to the central longitudinal axis.

As illustrated in, for example, FIGS. 2A, 3A, 3C, 5, 7, 8 and 9 the distal ends of the filaments when fully deployed may be disposed in a common plane. In an embodiment, the common plane may be disposed perpendicular to the central longitudinal axis. Such a common plane for the distal ends of deployed filaments may be disposed distally from the distal end of the tip.

As illustrated in, for example, FIGS. 2A, 3A, 3C, 5 and 7 the filaments of the needle may be deployed on a common side of a central plane of the needle (where the central longitudinal axis is disposed entirely within the central plane). In such embodiments, the distal ends of the fully deployed filaments may all be disposed on a common side of the central plane. Such a configuration may enable the needle to be used to create a lesion that is offset from the tip of the needle to the same side of the central plane as the deployed filament ends.

As illustrated, inter alia, in FIG. 2A, the filaments when fully deployed may point in an at least partially distal direction. In this regard, a vector extending axially from the distal end of a filament and coinciding with a central axis of the filament at the end of the filament has at least some distal component. Accordingly, the fully deployed filaments embodiments shown in FIGS. 2A, 3A and 10 all point in an at least partially distal direction.

Figure 9:
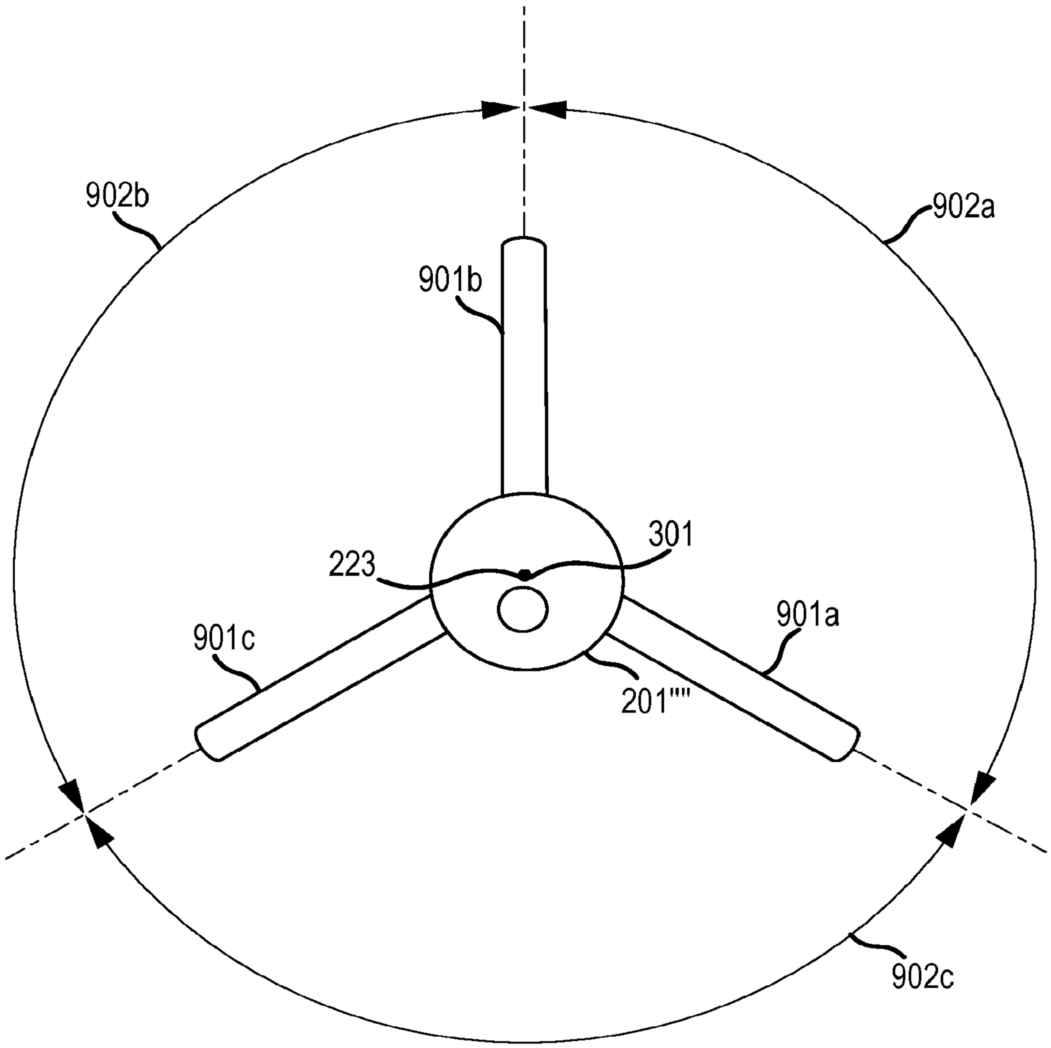
FIG. 9 is an end view of another alternate embodiment of the needle of FIG. 2A.

In another variation of the radial positioning of filaments of a needle, the filaments may be uniformly distributed about the circumference of the tip. Such an embodiment is illustrated in FIG. 9. The needle of FIG. 9 includes 3 equally distributed filaments 901*a*, 901*b*, 901*c*. Consequently, the angles 902*a*, 902*b*, 902*c* between the filaments 901*a*, 901*b*, 901*c* may each equal 120 degrees. Such a needle may be operable to produce a lesion that is generally centered along the central longitudinal axis 223. However, the position of the produced lesion axially along the central longitudinal axis 223 may be determined by the configuration of the filaments. For example, relatively longer filaments may be operable to produce lesions that are positioned distal to lesions produced by configurations with relatively shorter filaments.

Variations in the axial positioning of where deployed filaments emerge from the tip of a needle may be selected to achieve particular lesion sizes, positions and/or shapes. For example, returning to FIG. 7, if the third filament 701 of the embodiment of FIG. 7 were axially positioned such that it is distal to filaments 206*a*, 206*b*, the resultant lesion may be produced may be longer along the central longitudinal axis 223 than that of an embodiment where the filaments 206*a*, 206*b*, 701 are positioned at the same point along the central longitudinal axis 223. In another variation, as deployed, two or more filaments may be disposed at the same radial position and at different axial positions. Such embodiments may include multiple rows of filaments.

The lengths of filaments beyond the tip (when the filaments are in the deployed position) in a needle may be varied to achieve particular lesion sizes, positions and/or shapes. For example, increasing the length of the deployed portions of the filaments 206*a* and 206*b* of the embodiment illustrated in FIGS. 5 and 6 may result in a needle capable of producing lesions that are more distally positioned than those created by the embodiment as shown in FIGS. 5 and 6. The effects of lengthening or shortening the deployed length of the filaments are similar to those discussed above with respect to partially deploying filaments.

Embodiments of a needle may include deployed filaments of different lengths. Where all of the filaments of a particular needle are moved by a common actuator, such variations may be achieved by varying the overall length of the filaments. In such an embodiment, the end points of the shorter filaments may be retracted further into the tip or elongate member than longer filaments. The effects of lengthening or shortening the deployed length of the filaments are similar to those discussed above with respect to variations in the axial positioning of where deployed filaments emerge from the tip of the needle.

The angle (such as angle 601 of FIG. 6) at which a filament exits a tip may be varied to achieve particular lesion sizes, positions and/or shapes. For example, an embodiment similar to the embodiment of FIGS. 5 and 6, but where the deployed filaments are at a 60 degree angle instead of the 30 degree angle shown in FIG. 6, may be operable to produce a lesion that has a larger maximum cross-sectional dimension in a plane perpendicular to the central longitudinal axis 223 than the embodiment of FIGS. 5 and 6. This may be due to the filaments emanating RF energy at a distance further away from the central longitudinal axis than the embodiment of FIGS. 5 and 6. A particular embodiment of the needle may include deployed filaments at different angles relative to the central longitudinal axis.

The shapes of the portions of the filaments that extend away from the tip may be varied to achieve particular lesion sizes, positions and/or shapes. For example, FIG. 10 illustrates the tip 201 and filaments 1001*a*, 1001*b*, where the portions of the filaments 1001*a*, 1001*b* that extend beyond the tip 201 are curved. Such curvatures may be achieved by, for example, filaments that comprise a shape memory alloy (e.g., Nitinol) or spring material. When the filaments 1001*a*, 1001*b* are retracted, the shape of the tip 201 and/or elongate member 203 may keep the filaments 1001*a*, 1001*b* in a constrained straightened position. As the filaments 1001*a*, 1001*b* are advanced toward the fully deployed position, they become unconstrained and return to their curved shape as shown in FIG. 10. The deployed shape of the filaments 1001*a*, 1001*b* may be predetermined, or the filaments 1001*a*, 1001*b* may be made from a material that may be shaped by a user prior to insertion.

The curved filaments 1001*a*, 1001*b* of FIG. 10 are positioned within planes that include the central longitudinal axis 223. In other embodiments, the filaments 1001*a*, 1001*b* may be curved in other directions, such as in a corkscrew arrangement. This may be beneficial to assist the filaments in remaining anchored to the tissue during delivery of RF energy. The curved filaments 1001*a*, 1001*b* of FIG. 10 may be operable to produce a flatter (in a plane perpendicular to the central longitudinal axis 223) lesion than the straight filaments 206*a*, 206*b* of FIG. 6.

Figure 3C:
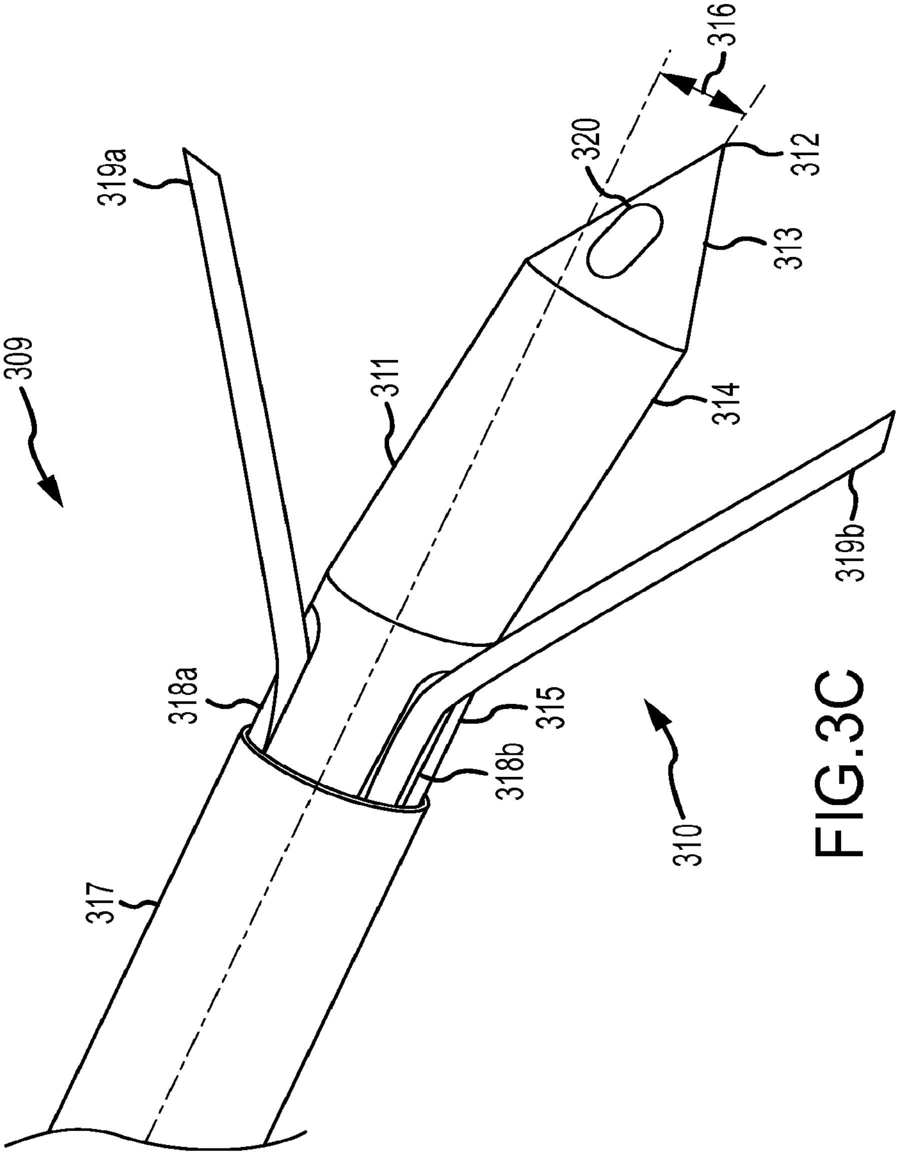
FIG. 3C is a detailed view of an alternate tip of the needle of FIG. 2A with filaments disposed in a deployed position.

FIG. 3C is a detailed view of the distal end 310 of a needle 309 that is an alternate embodiment of the needle 103. The distal end 310 includes a tip 311 that may include a sharpened point 312 for piercing the skin of a patient and facilitating advancement through tissue. The tip 311 may further include a tapered portion 313 that transitions the tip 311 from the point 312 to a first body portion 314. The first body portion 314 may be connected to a second body portion 315 at an angle 316. In an exemplary embodiment, the angle 316 may be about 15°. The second body portion 315 may be aligned with an elongate member 317. The elongate member 317 may be similarly configured as the elongate member 203 of FIGS. 3A and 3B. The angle 316 between the first body portion 314 and the second body portion 315 may aid the physician in navigating the needle 309 to a desired position. For example, by rotating the needle 309 such that the first body portion 314 is pointing in a desired direction, subsequent advancement of the needle 309 may result in the needle 309 following a non-straight path biased toward the desired direction.

The first and second body portions 314, 315 may be cylindrical as illustrated, or they may be of any other appropriate shape. The first and second body portions 314, 315 may have cross-sections that coincide with the cross section of the elongate member 317.

The tip 311, or a non-insulated portion thereof, may act as an RF energy delivery element. As such, the tip 311 may be made from a conductive material such as, for example, stainless steel. The tip 311 may be coated. The tip 311 material and optional coating may be selected to improve radiopacity, improve and/or alter RF energy conduction, improve lubricity and/or reduce tissue adhesion.

The tip 311 may include filament slot 318*a* and filament slot 318*b*. The geometry of the filament slots 318*a*, 318*b* may be selected to allow filaments 319*a*, 319*b* to be adequately retracted (e.g., such that they are disposed within a cross-sectional envelope of the second body portion 315) while the needle 309 is inserted into the body, so that the filaments 319*a*, 319*b* do not cause any unintended damage to the patient. Such positioning of the filament slots 318*a*, 318*b* avoids having filament exit features on the tapered portion 313 and on the first body portion 314 and thus avoids potential coring that could be caused by such positioning.

The internal geometry of the filament slots 318*a*, 318*b* may be designed such that the filaments 319*a*, 319*b* may be retracted and advanced. For example, the internal geometry of the filament slots 318*a*, 318*b* may be configured such that advancement of the filaments 319*a*, 319*b* relative to the filament slots 318*a*, 318*b*, will cause the filaments 319*a*, 319*b* to be deflected outwardly as the filaments 319*a*, 319*b* move distally relative to the second body portion 315. Depending on the configuration of the filament slots 318*a*, 318*b* and on the mechanical properties of the filaments 319*a*, 319*b*, various deployment angles of the filaments 319*a*, 319*b* relative to a central longitudinal axis of the second body portion 315 may be achieved.

The configuration and orientation of the filament slots 318*a*, 318*b* may be selected such that deployed filaments 319*a*, 319*b* may achieve the positioning illustrated in FIG. 3C. In FIG. 3C, the filaments 319*a*, 319*b* are generally positioned in a plane that is perpendicular to a plane that includes the angle 316 between the first and second body portions 314, 315. As illustrated, the filaments 319*a*, 319*b* may be positioned such that they extend at an angle relative to the plane that includes the angle 316. Other filament slot 318*a*, 318*b* configurations may be configured to achieve other desired filament 319*a*, 319*b* placements. These configurations may be achieved by varying the quantity of filament slots and filaments, the placement of filament slots about the circumference of the tip 311, the angle at which the filaments extend away from the first and second body portions 314, 315, and/or the placement of filament slots along the first and second body portions 314, 315.

Similar to the embodiment of FIGS. 3A and 3B, the needle 309 may comprise a tube that includes a lumen therethrough. The lumen may be employed to accept an RF probe for delivery of RF energy and/or for the transport of fluids. In this regard, the tip 311 may further include a fluid port 320 that may be in fluid communication via a channel through the tip 311 with the lumen. The fluid port 320 may be used to transfer fluid between the region of the tip 311 and a proximal end of the needle 309.

In the deployed position as shown in FIG. 3C, the distal ends of the filaments 319*a*, 319*b* are disposed away from the tip 311. In a retracted position (not shown, but similar to as shown in FIG. 3B), the distal ends of the filaments 319*a*, 319*b* are disposed entirely within an outer perimeter (e.g., circumference where the second body portion 315 of the tip 311 is round) of the tip 311. In the deployed position, the filaments 319*a*, 319*b* act as broadcast antennae for an RF probe inserted into the needle 309. In this regard, together, the RF probe inserted into the lumen, the tip 311, and the filaments 319*a*, 319*b*, may form a monopolar electrode for application of RF energy to the target volume. The filaments 319*a*, 319*b* may allow the RF energy from the RF probe to be dispersed over a larger volume than would be possible with the tip 311 alone.

The filaments 319*a*, 319*b* may be constructed in a manner similar to as described with respect to the filaments 206*a*, 206*b*.

In general, any or all of the above variables may be incorporated into a particular embodiment of a needle to yield a needle capable of producing a lesion with a particular size, position and shape relative to the tip of the needle. Such custom sizes, positions and shapes may be designed for specific procedures. For example, a particular lesion size, position and shape may be selected to enable a physician to navigate the needle to a particular landmark (e.g., proximate or touching a bone visible using fluoroscopy) and then orient the needle such that deployed filaments will be operable to produce a lesion at a particular location relative to the landmark. By navigating to a particular internal landmark, as opposed to attempting to visualize a relative position of a needle offset from a landmark, a more accurate and/or consistent positioning of the needle may be achieved. In this regard, the skill level required to accurately position the needle for a particular procedure may be reduced.

The lesion shapes achievable through selection of the above variables may include, for example, generally spherical, oblong, conical, and pyramidal shapes. The orientation relative to, and the amount of offset from, the tip of such shapes may be selectable. In an embodiment, the tips of the deployed filaments may be positioned distally relative to the point of the tip to provide for a facile positioning of the lesion relative to the tip. Such capability may allow for the needle to be inserted directly toward a target volume. In other embodiments, the tips of the deployed filaments may be positioned at the same axial position along the central longitudinal axis as the point of the tip or the tips of the deployed filaments may be positioned proximally relative to the point of the tip. In other embodiments, some filament endpoints may be located distal to the point of the tip while others are disposed proximal to the point of the tip.

In the embodiment of FIGS. 2A, 2B, 3A, 3B, 5 and 6, the filaments 206*a*, 206*b* have been illustrated as running the entire length of the elongate member 203 from the filament hub 221 to the tip 201. In an embodiment, a single member may run along at least part of the elongate member 203 and the filaments may be interconnected to the single member at some point proximal to the tip 201. Furthermore, the filaments 206*a*, 206*b* have been illustrated as being straight within the elongate member 203. In alternate embodiments, the filaments within the elongate member 203 may be braided, wrapped or twisted together. Such embodiments may have increased column strength, providing resistance to buckling and/or bending within the elongate member 203.

The filaments discussed herein may be encased within lumens sized to help prevent buckling or bending of the filaments within the elongate member 203. Such lumens may be part of the elongate member or they may be separate members (e.g., tubes within the elongate member). Such lumens may be formed by an inner member (not shown) within the elongate member where the inner member includes channels along its periphery in which the filaments may lie with the elongate member forming a portion of the lumens. Lumens used for filaments may also serve as lumens for the transfer of liquid to and/or from the region surrounding the tip. In another variation, the filaments may be hollow and may be used for transfer of liquid to and/or from the region surrounding the tip.

The illustrated embodiments show all of the filaments of a given embodiment as commonly deployed or refracted. In a variation, one or more filaments may be separately deployed and/or refracted such that the physician could selectively engage a desired number of elements. In another variation, a plurality of filaments may exit from the tip at a common location and form a fan-like arrangement as they are deployed.

Deployment of filaments discussed above has been described as the filaments moving relative to a stationary tip. Alternatively, embodiments may be deployed by pulling the tip back relative to the filaments. Such embodiments may be beneficial where the needle is initially advanced such that it is in contact with bone to ensure proper positioning. Then the tip may be withdrawn, leaving the filaments (e.g., curved shape memory filaments) in a precise, known position.

Returning to FIGS. 2A and 2B, as noted, the hub 204 may be fixedly attached to the elongate member 203. The hub 204 may be the primary portion of the needle 103 gripped by the physician during insertion and manipulation of the needle 103. The hub 204 may have an asymmetric feature, such as indicator 225, that is oriented in a known fashion relative to the asymmetry of the tip 201. In this regard, the indicator 225 may be used to communicate to the physician the orientation of the tip 201 within the patient 101. Internally, the hub 204 may include a cavity 213 sized to house a protrusion 218 of the actuator 216. The hub 204 may include a hole through which a projection 215 may project into the interior of the cavity 213 to control the motion of the actuator 216 relative to the hub 204 and to secure the actuator 216 to the hub 204. The hub 204 may be made from any appropriate material, e.g., a thermoset plastic.

The actuator 216 may be used to control the motion to deploy and/or retract the filaments 206*a*, 206*b*. The actuator 216 is operable to move along the central longitudinal axis 223 relative to the hub 204, elongate member 203 and tip 201. The actuator 216 includes the protrusion 218 extending into the cavity 213 of the hub 204. The outer surface of the protrusion 218 includes a helical track 219 sized to accommodate the projection 215. In this regard, as the actuator is rotated relative to the hub 204 (e.g., by a physician to deploy the filaments 206*a*, 206*b*), the helical track 219 and projection 215 combine to cause the actuator 216 to move axially along the central longitudinal axis 223. The actuator 216 has an interface portion 217 that may be gripped by a user when twisting the actuator 216. The interface portion 217 may be knurled or otherwise textured to enhance the physician's ability to twist the actuator 216. The protrusion 218 may include an inner cavity 226 sized to accept the filament hub 221 and to allow the filament hub 221 to rotate freely relative to the actuator 216. In this regard, the linear motion of the actuator 216 may be transmitted to the filament hub 221 while the rotational motion of the actuator 216 may not be transmitted to the filament hub 221.

The actuator 216 may include a Luer fitting 220 or any other appropriate fitting type on a proximal end thereof. The Luer fitting 220 may be in fluid communication with the lumen 222 and provide a connection such that fluid may be delivered into the lumen 222 and to the fluid port 210 of the tip 201. The Luer fitting 220 may also be configured to allow for the insertion of the RF probe 401 into the lumen 222. The actuator 216 may be made from any appropriate material.

The filaments 206*a*, 206*b* may be fixedly interconnected to the filament hub 221. In this regard, the axial movement of the filament hub 221 due to the actuator 216 may be communicated to the filaments 206*a*, 206*b* to deploy and retract the filaments 206*a*, 206*b* when the actuator 216 is rotated. The filament hub 221 may be made from any appropriate material.

Thusly, the physician may be able to deploy or retract the filaments 206*a*, 206*b* by twisting the actuator 216. For example, as illustrated, a counterclockwise (as seen from the viewpoint of FIG. 5) rotation of the actuator 216 relative to the hub 204 will result in the deployment (extension) of the filaments 206*a*, 206*b*. Relatedly, a clockwise rotation of the actuator 216 relative to the hub 204 will result in the retraction of the filaments 206*a*, 206*b*. Additionally, by partially rotating the actuator 216 relative to the hub 204, the filaments 206*a*, 206*b* may be partially deployed or refracted. The actuator 216 and/or the hub 204 may include markings to indicate the position of the filaments 206*a*, 206*b* (e.g., the depth of deployment). The actuator 206 and/or hub 204 may include detents to provide a tactile feedback of the position of the filaments 206*a*, 206*b*.

Other types of mechanisms may be used to control the deployment and retraction of the filaments 206*a*, 206*b*. For example, a spring loaded mechanism may be used. Such a configuration may use a spring that acts upon the filaments 206*a*, 206*b* to bias the filaments 206*a*, 206*b* toward a predetermined position (e.g., either deployed or retracted). Such a mechanism may be analogous to a spring loaded mechanism used in retractable ballpoint pens. In another example, a roll clamp mechanism may be incorporated. A roller wheel could be incorporated into the hub 204 such that as the wheel is rotated with the user's thumb, the filaments 206*a*, 206*b* would advance or retract. In another example, the hub 204 and actuator 216 may interact via complimentary threaded features. As the actuator 216 is threaded into the hub 204, the filaments 206*a*, 206*b* would advance. As the actuator 216 is threaded out of the hub 204, the filaments 206*a*, 206*b* would retract. In another example, a Touhy-Borst type mechanism could be incorporated to control the deployment and retraction of the filaments 206*a*, 206*b*. Any other appropriate mechanism for controlling linear motion of the filaments 206*a*, 206*b* may be incorporated into the needle 103.

Figure 2C:
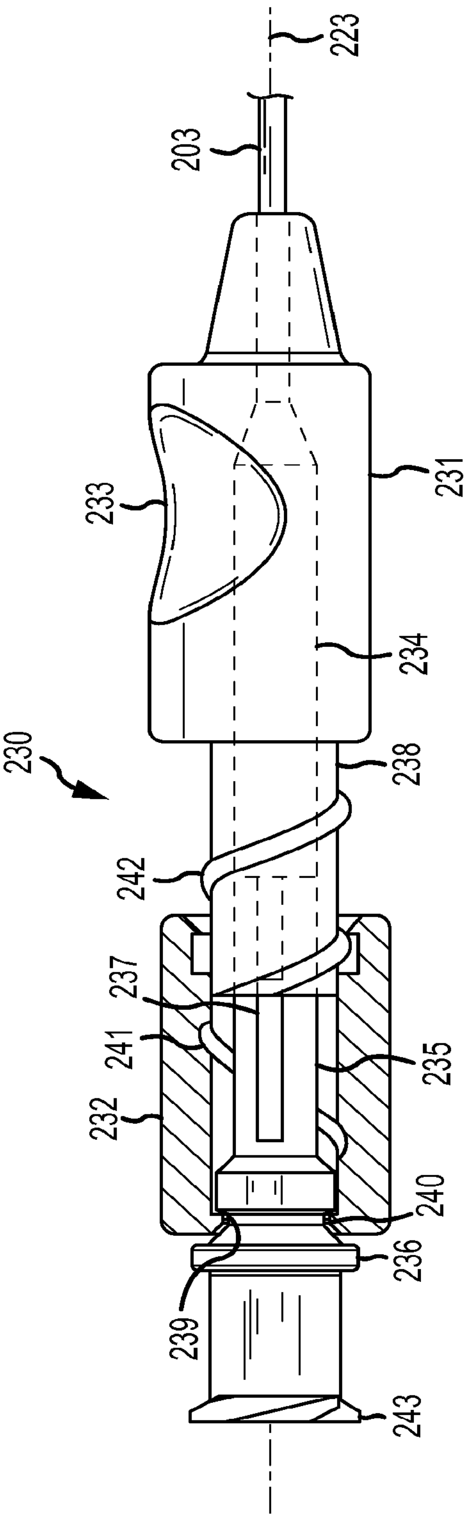
FIG. 2C is a cut away view of a portion of an alternate embodiment of a needle that may be used in an RF neurotomy procedure.

FIG. 2C is a cut away view of a portion of an alternate embodiment of a hub 231 and actuator 232 that may be part of RF needle 103 used in an RF neurotomy procedure. The hub 231 may be fixedly attached to the elongate member 203. The hub 231 may be the primary portion of the needle 103 gripped by the physician during insertion and manipulation of the needle 103. The hub 231 may have an asymmetric feature, such as indicator 233, that is oriented in a known fashion relative to the asymmetry of the tip 201. In this regard, the indicator 233 may be used to communicate to the physician the orientation of the tip 201 within the patient 101. Internally, the hub 231 may include a cavity 234 sized to house a protrusion 235 of a slide member 236. The protrusion 235 may include a keyway or key slot 237 that may run along a longitudinal direction of the protrusion 235. The internal surface of the hub 231 through which the protrusion 235 moves may include a mating key (not shown) configured to fit and slide within the key slot 237. Together, the key slot 237 and mating key of the hub 231 may limit the slide member 236 to a linear motion along the central longitudinal axis 223.

Filaments 206*a*, 206*b* may be fixedly connected to the protrusion 235 of the slide member 236 for movement therewith. In this regard, distal movement (e.g., movement to the right as shown in FIG. 2C) of the protrusion 235 relative to the hub 231 may cause extension of the filaments 206*a*, 206*b* relative to the hub 231, elongate member 203 and tip 201 (not shown in FIG. 2C). For example, distal movement of the protrusion 235 may be used to move the filaments 206*a*, 206*b* from a retracted position to a deployed position. Similarly, proximal movement (e.g., movement to the left as shown in FIG. 2C) of the protrusion 235 relative to the hub 231 may result in retraction of the filaments 206*a*, 206*b* relative to the hub 231, elongate member 203 and tip 201 (not shown in FIG. 2C).

The hub 231 may be made from any appropriate material, e.g., a thermoset plastic. The hub 231 may be at least partially transparent such that the position of the protrusion 235 and/or other components within the hub 231 may be observable by a user. The hub 231 may further include demarcations (e.g., molded or printed marks) such that the amount of extension of the filaments 206*a*, 206*b* may be determined from the position of the protrusion 235 and/or other components relative to the demarcations.

An actuator 232 may be used to control the motion to deploy and/or retract the filaments 206*a*, 206*b* fixedly connected to the protrusion 235. The actuator 232 may be generally tubular such that it may fit around a hub projection 238 projecting from the proximal end of the hub 231. At least a portion of the cavity 234 may be disposed within the hub projection 238. The actuator 232 may also include an annular feature 239 configured to fit within an annular slot 240 in the slide member 236. The annular feature 239 may be sized relative to the annular slot 240 such that the actuator 232 may rotate relative to the slide member 236 about the central longitudinal axis 223 (or an axis parallel thereto) while the position of the actuator 232 relative to the slide member 236 along the central longitudinal axis 223 remains fixed. In this regard, the actuator 232 and the slide member 236 may be configured to move in tandem relation along the central longitudinal axis 223. The annular feature 239 and annular slot 240 may be configured such that, during assembly, the actuator 232 may be pressed onto the slide member 236 and the annular feature 239 may snap into the annular slot 240.

The inner surface of the actuator 232 may include a helical track 241 sized to accommodate a corresponding mating helical thread 242 on the hub projection 238. In this regard, as the actuator 232 is rotated relative to the slide member 236 and hub 231 (e.g., by a physician to deploy the filaments 206*a*, 206*b*), the helical track 241 and helical thread 242 combine to cause the actuator 232 and the slide member 236 to move axially along the central longitudinal axis 223. In this regard, a linear motion of the slide member 236 relative to the hub 231 may be created while the rotational motion of the actuator 232 may not be transmitted to the slide member 236 and the hub 231. An outer surface of the actuator 232 may be textured or include features to assist the user in gripping and twisting the actuator 232. In an alternative configuration, the helical track 241 may be disposed on the hub projection 238 and the helical thread 242 may be disposed on the inner surface of the actuator 232.

The slide member 236 may include a Luer fitting 243 or any other appropriate fitting type on a proximal end thereof. The Luer fitting 243 may be in fluid communication with a lumen passing through the slide member 236 and may provide a connection such that fluid may be delivered through the Luer fitting 243 and into the lumen of the slide member 236. In turn, the lumen of the slide member 236 may be in fluid communication with the cavity 234 of the hub 231, which may in turn be in fluid communication with a lumen disposed within the elongate member 223. The lumen disposed within the elongate member 223 may be in fluid communication with the tip 201. In this regard, fluid may flow into the Luer fitting 243, into and through the lumen within the slide member 236, into and through the cavity 234 of the hub 231, into and through the elongate member 223, and out from the tip 201. The Luer fitting 243, the lumen within the slide member 236, the cavity 234 of the hub 231, and the lumen of the elongate member 223 may all also be configured to allow for the insertion of the RF probe 401 therethrough. Moreover, the protrusion 235 and cavity 234 of the hub projection 238 may be sized and/or configured to form a fluid seal therebetween. Accordingly, fluid delivered under pressure through the Luer fitting 220 may flow through the cavity 238 and into the elongate member 203 substantially without leaking past the interface between the protrusion 235 and the cavity 234 of the hub projection 238.

As noted, the filaments 206*a*, 206*b* may be fixedly interconnected to the slide member 236. In this regard, the axial movement of the slide member 236 due to the actuator 232 may be communicated to the filaments 206*a*, 206*b* to deploy and retract the filaments 206*a*, 206*b* when the actuator 232 is rotated. The slide member 236 may be made from any appropriate material. The actuator 232 may be made from any appropriate material.

Thusly, the physician may be able to deploy or retract the filaments 206*a*, 206*b* by twisting the actuator 232. Additionally, by partially rotating the actuator 232 relative to the hub 231, the filaments 206*a*, 206*b* may be partially deployed or refracted. The actuator 232 and/or hub 231 may include detents to provide a tactile feedback of the position of the filaments 206*a*, 206*b*. The detents may be configured such that tactile feedback associated with engagement of a detent coincides with a predetermined amount of deployment or retraction of the filaments 206*a*, 206*b*. In this regard, such tactile feedback may be used in determining filament position.

In alternate embodiments, the needle 103 may be a bipolar device instead of the monopolar device described above. In such embodiments, the filaments may be isolated from each other and the tip to enable bipolar operation. Where more than two filaments are included, elements may be included to allow for selection of the polarity of the filaments to aid in lesion shape, size and position control. In another variation, the needle 103 may be used in either a monopolar or a bipolar mode as selected by the physician.

The above-described embodiments of needles may used in spinal RF neurotomy procedures, which will now be described. In general, for an RF neurotomy procedure, the patient may lie face down on a table so that the spine of the patient is accessible to the physician. At any appropriate time before, during, and/or after the procedure, the physician may use imaging equipment, such a fluoroscope, to visualize the patient's anatomy and/or to visualize the positioning of equipment (e.g., the needle relative to a target volume).

The patient may be administered sedatives and/or intravenous fluids as appropriate. The skin of the patient surrounding where the procedure will take place may be prepared and maintained using an appropriate sterile technique. Where the needle is a monopolar device, a return electrode pad may be attached to the patient. A local anesthetic may be injected subcutaneously where the needle will be inserted. Anesthetic may also be administered along the approximate path the needle will take.

With the filaments in the retracted position, the needle may be introduced into the patient and moved to a target position relative to a target portion of a target nerve or to a target position relative to a target volume in which the target nerve is likely situated (all of which are generally referred to herein as the target nerve or portion of the target nerve). The target nerve may be an afferent nociceptive nerve such as, for example, a medial branch nerve proximate a lumbar facet joint. Introduction into the patient may include percutaneously using the tip of the needle to pierce the skin of the patient. The moving of the needle may include navigating toward the target position using fluoroscopic guidance.

Furthermore, the moving of the needle may include advancing the needle to an intermediate position and then repositioning the needle to the target position. For example, the needle may be advanced until it contacts a bone or other structure to achieve the intermediate position. This may be followed by retracting the needle a predetermined distance to achieve the target position. Such a procedure may be facilitated by the markers 224 or collar previously discussed.

During the moving of the needle or after the target position has been achieved, the needle may be used to inject an anesthetic and/or a dye. The dye may increase contrast in fluoroscopic images to assist in visualizing the patient's anatomy, which may aid the physician in guiding and/or verifying the position of the needle.

The needle may be rotated about the central longitudinal axis of the elongate member of the needle to achieve a desired orientation relative to the target nerve. For example, the needle may be rotated such that a lesion created with the needle with the filaments deployed will be offset from the central longitudinal axis toward the target nerve. Such rotation of the needle may be performed prior to insertion of the needle into the patient and/or after insertion into the patient. For example, the physician may rotate the needle prior to insertion such that the needle is generally in the desired rotational orientation. Then, after achieving the target position, the physician may fine tune the rotational orientation of the needle by rotating the needle to a more precise orientation.

Once the target position and desired rotational orientation have been achieved, the next step may be to advance one or more filaments of the needle relative to the tip of the needle. The particular needle used for a procedure may have been selected to enable the creation of a particular sized and shaped lesion at a particular position relative to the needle. As such, the particular needle used may be of any appropriate configuration (e.g., any appropriate number of filaments, any appropriate filament positioning) discussed above.

Where the needle is configured as shown in FIG. 5, the advancement of filaments may include advancing the filaments such that when the filaments are in their respective deployed positions, a midpoint between a distal end of the first filament and a distal end of the second filament is offset from the central longitudinal axis of the needle and the filament endpoints are disposed distal to the tip of the needle. Such deployment may enable the needle to be used to create a lesion that is offset from the tip of the needle toward the midpoint between the deployed filament ends. The lesion created may also be positioned at least partially distal to the tip of the needle.

Figure 11A:
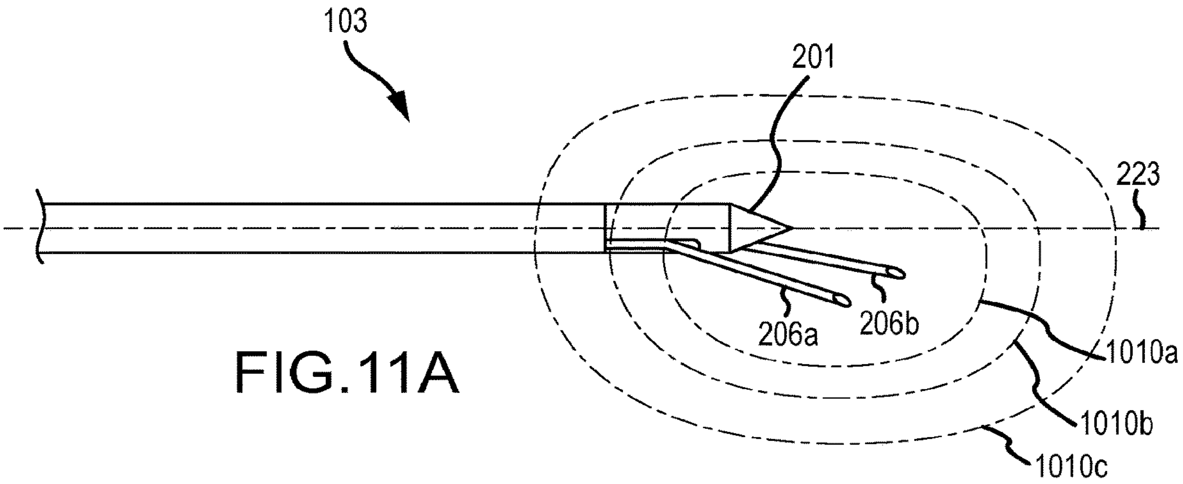
FIG. 11A is an illustration of an exemplary set of isotherms that may be created with the needle of FIG. 2A.

FIG. 11A is an illustration of an exemplary set of isotherms 1010_a_-1010_c_ that may be created with the needle 103 of FIG. 2A. As illustrated by the set of isotherms 1010_a_-1010_c_, RF energy emanating from the tip 201 and filaments 206_a_, 206_b_, may produce a region of elevated temperatures disposed about the tip 201 and filaments 206_a_, 206_b_. The isotherms 1010_a_-1010_c_ may be offset from the central longitudinal axis 223 such that a centroid of the isotherms as viewed in FIG. 11A is offset from the central longitudinal axis 223 in the direction of the filaments 206_a_, 206_b_. The centroid of the isotherms 1010_a_-1010_c_ as viewed in FIG. 11A may also be disposed distally relative to the tip 201 such that it is disposed between the tip 201 and the distal ends of the deployed filaments 206_a_, 206_b_. The isotherms 1010_a_-1010_c_ may also be shaped such that, as viewed in FIG. 11A, the isotherms 1010_a_-1010_c_ have a maximum cross dimension along the central longitudinal axis 223 that is greater than a maximum cross dimension in the plane of FIG. 11A perpendicular to the central longitudinal axis 223. Similarly, as shown in FIG. 11B discussed below, the isotherms 1010_a_-1010_c_ may have a maximum cross dimension along the central longitudinal axis 223 that is greater than a maximum cross dimension perpendicular to the plane of FIG. 11A and perpendicular to the central longitudinal axis 223.

The offset of the centroid of the isotherms 1010_a_-1010_c_ from the central longitudinal axis 223 results in greater lesion width in a plane perpendicular to the central longitudinal axis 223, as compared to a similarly sized straight needle with no filaments. The offset of the centroid of the isotherms 1010_a_-1010_c_ also allows for projection of the centroid of a corresponding lesion volume in a direction away from the central longitudinal axis 223. By way of example, such offsets may advantageously enable the execution of the exemplary procedures described herein. In addition, such offsets may advantageously enable the creation of lesion volumes distal (relative to the needle 103) to potentially interfering structures (e.g., an ossified process). Moreover, such offsets may advantageously enable the needle 103 to be inserted into a patient at a more desirable angle (e.g., closer to perpendicular to the surface of the patient such as within 30° of perpendicular to the surface of the patient) than would be required using a needle without offset lesion capabilities.

Figure 11B:
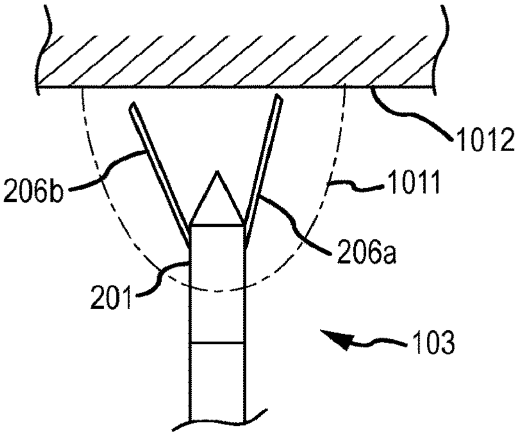
FIG. 11B is an illustration of an exemplary lesion that may be created with the needle of FIG. 2A.

FIG. 11B is an illustration of an exemplary lesion 1011 that may be created with the needle 103 of FIG. 2A. In FIG. 11B, the needle 103 has been placed perpendicular to a surface 1012. The surface 1012 may, for example, be the surface of a bone, such as a lumbar vertebra. As illustrated, the filaments 206_a_, 206_b_ are deployed such they are proximate to the surface 1012. As such, the lesion 1011 has a width along the surface 1012 that is wider than would be created by the needle 103 if the filaments 206_a_, 206_b_ were not deployed. Such capabilities may, for example, be advantageous where a target structure (e.g., a nerve) is known to be positioned along the surface 1012, but its exact position is unknown. In such a case, the needle 103 may be positioned generally perpendicular to the surface 1012 to achieve the illustrated lesion width along the surface 1012, whereas the needle 103 without the filaments 206_a_, 206_b_ deployed, would require either multiple repositioning steps or for the needle 103 to be placed generally parallel to the surface 1012 to achieve the same lesion width along the surface 1012.

Figure 11C:
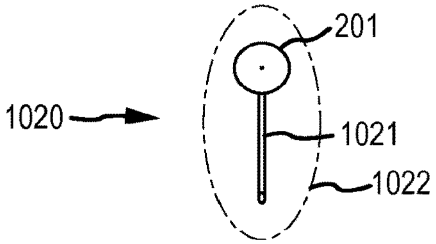
FIG. 11C is an illustration of an exemplary lesion that may be created with a single-filament needle.

FIG. 11C is an illustration of an exemplary lesion 1022 that may be created with a single-filament needle 1020. The single-filament needle 1020 is similar to the needle 103 with a difference that the single-filament needle 1020 includes only a single filament 1021. The filament 1021 may be configured similarly to the filaments 206_a_, 206_b_. The single-filament needle 1020 with the filament 1021 deployed may be operable to produce a lesion 1022 that is a flattened version (e.g., thinner in a direction perpendicular to the central longitudinal axis 223—the left to right direction as illustrated in FIG. 11C) of a lesion that may be produced by the needle 103 with its filaments 206_a_, 206_b_ deployed. The capability to produce such a lesion shape may be beneficial when it is desirable to have a relatively large lesion in a particular direction (e.g., to compensate for the variability of location of a target nerve) and a relatively small lesion width in another direction (e.g., to avoid a structure such as viscera or a patient's skin).

Where the needle is configured such that all of the filaments of the needle are deployed on a common side of a central plane of the needle (where the central longitudinal axis is disposed entirely within the central plane), the advancement of filaments may include advancing the filaments such that when the filaments are in their respective deployed positions, the distal ends of all of the filaments are disposed on a common side of the central plane. Such deployment may enable the needle to be used to create a lesion that is offset from the tip of the needle to the same side of the central plane as the deployed filament ends. The lesion created may also be positioned at least partially distal to the tip of the needle.

Where the needle is configured as shown in FIG. 8, the advancement of filaments may include advancing the filaments such that when the filaments are in their respective deployed positions, each filament distal end defines a vertex of a polygon whose centroid is offset from a central longitudinal axis of the needle. Such deployment may enable the needle to be used to create a lesion that is offset from the tip of the needle toward the centroid. The lesion created may also be positioned at least partially distal to the tip of the needle.

The advancement of the filaments may be achieved using any of the mechanisms discussed above. For example, in the embodiment of FIG. 2A, rotating the actuator 216 relative to the hub 104 may cause the filaments to advance to the deployed position. The advancement of the filaments may be performed such that each of the plurality of filaments passes through a surface of the needle that is parallel to the central longitudinal axis of the needle. In an embodiment, the filaments of the needle may be advanced to a position that is an intermediate position between the retracted position and the fully deployed position. The degree of deployment may be based on the desired lesion size and/or the accuracy of the placement of needle. For example, the same needle may be used in two different procedures where the variability of the location of a target nerve is greater in the first procedure than it is in the second procedure. In such situation, the greater deployment of the filaments may be used in the first procedure, whereas in the second procedure, a smaller degree of deployment may be used since a smaller lesion may suffice to ensure that the target nerve has been lesioned. In another example, after placement of the needle during a procedure, the position of the needle may be determined to be slightly offset from a target position. In such a case, the filaments may be deployed to a greater degree than would have been required if the needle were placed exactly on target. In such a case, the greater degree of deployment may be used to compensate for the needle positioning inaccuracy. In such a case, needle repositioning and possible associated trauma may be avoided.

After advancing the filaments to the deployed position, their positions may be confirmed using the imaging system (e.g., using a fluoroscope). Furthermore, proper positioning may be verified by using the needle to stimulate the target nerve. An electrical signal (e.g., up to about 2 volts applied at about 2 Hz) may be applied to the needle and the physician may observe any related patient movement (e.g., muscle fasciculation in the territory supplied by the nerve). In another example, an electrical signal (e.g., up to about 1 volt applied at about 50 Hz) may be applied to the needle and the patient may indicate if they feel any associated sensations and their locations to assist in verifying correct needle positioning. Such stimulation (either physician-observed or patient reported) may be used to stimulate a targeted nerve to determine if the deployed position is adequate to achieve denervation of the targeted nerve. In this regard, it is desirable for the stimulation to affect the targeted nerve.

Such stimulation may be used to attempt to stimulate a nerve that is not targeted for denervation (e.g., a nerve where no denervation is desired) to determine the position of the needle relative to such a non-targeted nerve. In this regard, if the stimulation signal does not stimulate the non-targeted nerve, it may be assumed that the position of the needle relative to the non-targeted nerve is such that the application of RF energy to the needle will not result in significant damage to the non-targeted nerve. And if the stimulation does stimulate the non-targeted nerve, the needle may be repositioned to avoid damaging the non-targeted nerve. In this regard, it is desirable for the stimulation not to affect the non-targeted nerve.

After correct needle positioning has been verified (e.g., by imaging and/or patient response), an anesthetic may be injected through the needle.

After the filaments have been advanced to the desired position, the next step may be to apply RF energy to the needle using the interconnected RF generator. In embodiments that use a separate RF probe to deliver RF energy, the RF probe may be inserted into a lumen of the needle prior to application of the RF energy. Additionally, when using such a configuration, the application of RF energy may include applying RF energy to the RF probe and conducting the RF energy away from the probe by the tip and/or filaments.

The resultant RF energy emanating from the tip and filaments may generate heat that ablates the target nerve. Such ablation may be achieved by creating a lesion that includes the target nerve. It is desired that the target nerve be completely ablated to prevent incomplete neurotomy which may result in dysesthesia and patient discomfort. In an exemplary embodiment, a lesion with a maximum cross dimension of 8-10 mm may be created. Larger or smaller lesions may be created by varying filament characteristics (e.g., filament advancement distance) and/or RF energy levels. The created lesion may be offset from the central longitudinal axis of the needle. The center of the lesion may be positioned distal to the tip of the needle. Of note, since the RF energy is emanating from the tip and filaments, a particularly sized lesion may be created with a lower peak temperature (the maximum temperature experienced in the patient) than would be possible if a needle without filaments were to be used to create the same-sized lesion. For example, a particular lesion may be achieved with the needle with deployed filaments where the peak temperature is about 55-60° C., whereas creation of the same lesion using a needle without filaments could require a peak temperature of about 80° C. Such lower temperatures required by the needle with deployed filaments may result in greater patient safety.

Before, during, and after the application of RF energy, a temperature sensor (e.g., thermocouple) at or near the tip of the needle may be used to monitor the temperature at or near the tip. Such readings may be used as control signals (e.g., a feedback loop) to control the application of RF energy to the needle. If it is desired to ablate additional target nerves or to ablate an additional volume to ensure ablation of the original target nerve, the spinal RF neurotomy procedure may continue.

Where the particular needle is configured to create lesions offset from the central longitudinal axis of the needle, and the additional target nerve or target volume is within a volume that may be lesioned using the needle in its current position but in a different rotational orientation, the procedure may continue as follows. First, after the initial RF energy application, the filaments may be retracted into the needle. Once retracted, the needle may be rotated, and the filaments redeployed. Next, the reoriented needle may be used to at least partially ablate the additional target nerve or target volume. Such retargeting of ablation volumes without repositioning (e.g., without withdrawing the needle from the patient and reinserting), may result in reduced patient trauma as compared to known spinal RF neurotomy procedures which may require removal and reinsertion of a needle to achieve lesioning of the second target volume. Moreover, such retargeting of ablation volumes without repositioning may result in the ability to create uniquely shaped lesions from a single insertion position. Such shaped lesions may include, for example, lesions that are in the shape of two or more intersecting spheres. The steps of retracting the filaments, rotating the needle, redeploying the filaments, and applying RF energy may be repeated a plurality of times.

Where the additional target nerve or target volume is not within a volume that may be lesioned using the needle in its current position, the needle may be repositioned. Such repositioning may include partially or fully removing the needle from the patient and then repositioning the needle and repeating the above-described steps.

At any point where no additional lesioning is desired, the filaments of the needle may be retracted, and the needle may be removed from the patient. After removal of the needle, a sterile bandage may be placed over the needle insertion site or sites. The patient may then be held for observation and recovery from the effects of any sedative that may have been administered.

Examples of specific spinal RF neurotomy procedures will now be described. Generally, steps unique to each procedure will be discussed while steps common to any spinal RF neurotomy procedure (e.g., site preparation, needle removal) will not be further discussed. Each of the procedures is described as being performed with the needle 103 of FIGS. 2A-6. It will be appreciated that the variations in needle configuration discussed above may be used in these procedures. For example, to increase the offset of the created lesion relative to the central longitudinal axis, curved (e.g., FIG. 10) and/or partially insulated filaments may be used that may create a lesion with a greater offset from the central longitudinal axis than the embodiment of FIG. 2A-6.

1. Lumbar RF Neurotomy of a Medial Branch Nerve Proximate a Lumbar Facet Joint.

This process may include using a needle that enables the creation of lesions which are offset from the central longitudinal axis of the needle. The procedure will be described as being performed on the L5 vertebra 1101 using FIG. 12 and the needle 103 of FIG. 2A. It should be understood that other embodiments of needles described herein may be used in the procedure.

Figure 12:
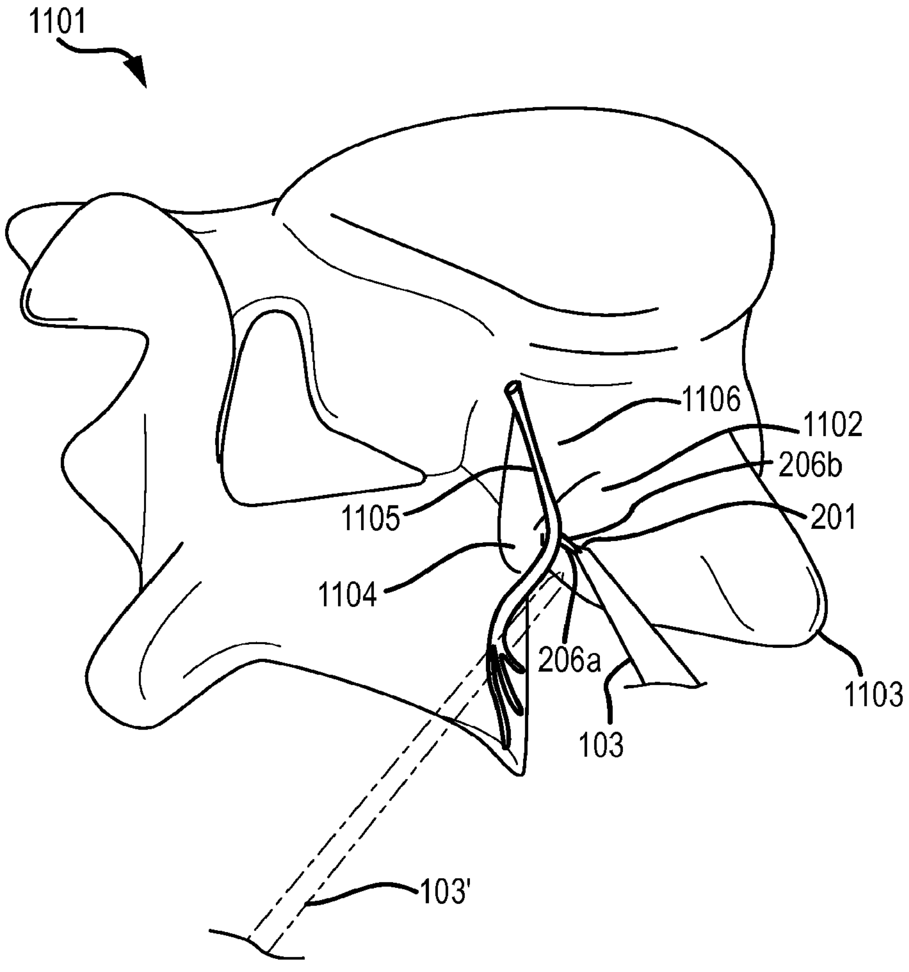
FIG. 12 is a perspective view of the needle of FIG. 2A positioned relative to a lumbar vertebra for performing RF neurotomy.

The lumbar RF neurotomy process may include positioning the tip 201 of the needle 103 (e.g., using fluoroscopic navigation) such that it is in contact with, or proximate to the groove 1102 between the transverse 1103 and superior articular 1104 processes of the targeted lumbar vertebra 1101. Such positioning is shown in FIG. 12. By contacting the lumbar vertebra 1101, a positive determination of the position of the needle 103 may be made. By way of example, such positioning may be performed such that the needle 103 is within 30° of being perpendicular to the lumber vertebra 1101 at the point of contact with the lumbar vertebra 1101, or at the point of the lumbar vertebra 1101 closest to the tip 201 of the needle 103. Optionally, from such a position, the needle 103 may be retracted a predetermined amount (e.g., between about 3 mm and 5 mm) as measured by markers 224 on the needle 103, as determined using the collar about the elongated member 203 discussed above, and/or by fluoroscopic navigation.

The process may include rotating the needle 103 such that the midpoint 502 is oriented toward the superior articular process 1104 and a medial branch nerve 1105 that is positioned along a lateral face 1106 of the superior articular process 1104. Next, the filaments 206*a*, 206*b* may be advanced to the deployed position (as shown in FIG. 12). The position of the needle 103 and deployed filaments 206*a*, 206*b* may be verified using fluoroscopy and/or patient stimulation. The RF probe 401 may then be inserted into the lumen 222 such that RF energy emanating from the probe 103 will be conducted by the tip 201 and filaments 206*a*, 206*b* to the target medial branch nerve 1105 and away from the intermediate branch of the posterior primary ramus.

Next, RF energy may be applied to the RF probe 401. The RF energy emanating from the needle 103 may be preferentially biased toward the target medial branch nerve 1105. The lesion created by such a procedure may, for example, have a maximum cross dimension of 8-10 mm, and may ablate a corresponding portion of the medial branch nerve 1105, thus denervating the facet joint.

In a variation, the needle may be operable to create a generally symmetric lesion relative to its central longitudinal axis. In such a variation the sequence of steps may include insert needle, deploy filaments, and apply RF energy.

In another variation, the needle may be inserted so it is positioned along the length of a portion of the nerve (as illustrated by needle 103'). Such positioning is similar to known methods of RF neurotomy performed with needles without filaments. After positioning the needle, the filaments may be deployed and a lesion may be created. As noted above, a needle with deployable filaments that is capable of producing a lesion equivalent to that of a needle without deployable filaments may be smaller in diameter than the needle without deployable filaments. Accordingly, although the positioning of needle 103' may be similar to known processes, the process utilizing the needle with deployable filaments may cause less trauma and be safer than procedures using a needle without deployable filaments due to the smaller size of the needle with deployable filaments. Moreover, as discussed above, the peak temperatures required to produce the desired lesion volume may be less when using the needle with deployable filaments as compared to the needle without deployable filaments, further contributing to patient safety. Furthermore, the filaments of needle 103' may be partially or fully deployed to achieve a desired lesion location, shape and/or size.

It is noted that the illustrated deployment of needle 103 with the filaments 206*a*, 206*b* deployed may be used to create a lesion that approximates a lesion that would be created with the a prior art (non filament) needle placed in the position of needle 103' (e.g., parallel to the target nerve 1105). Moreover, the placement of needle 103 generally perpendicular to the surface of the L5 vertebra 1101 may be less difficult to achieve than the parallel placement of the needle 103'.

2. Sacroiliac Joint (SIJ) RF Neurotomy of the Posterior Rami.

Figure 13:
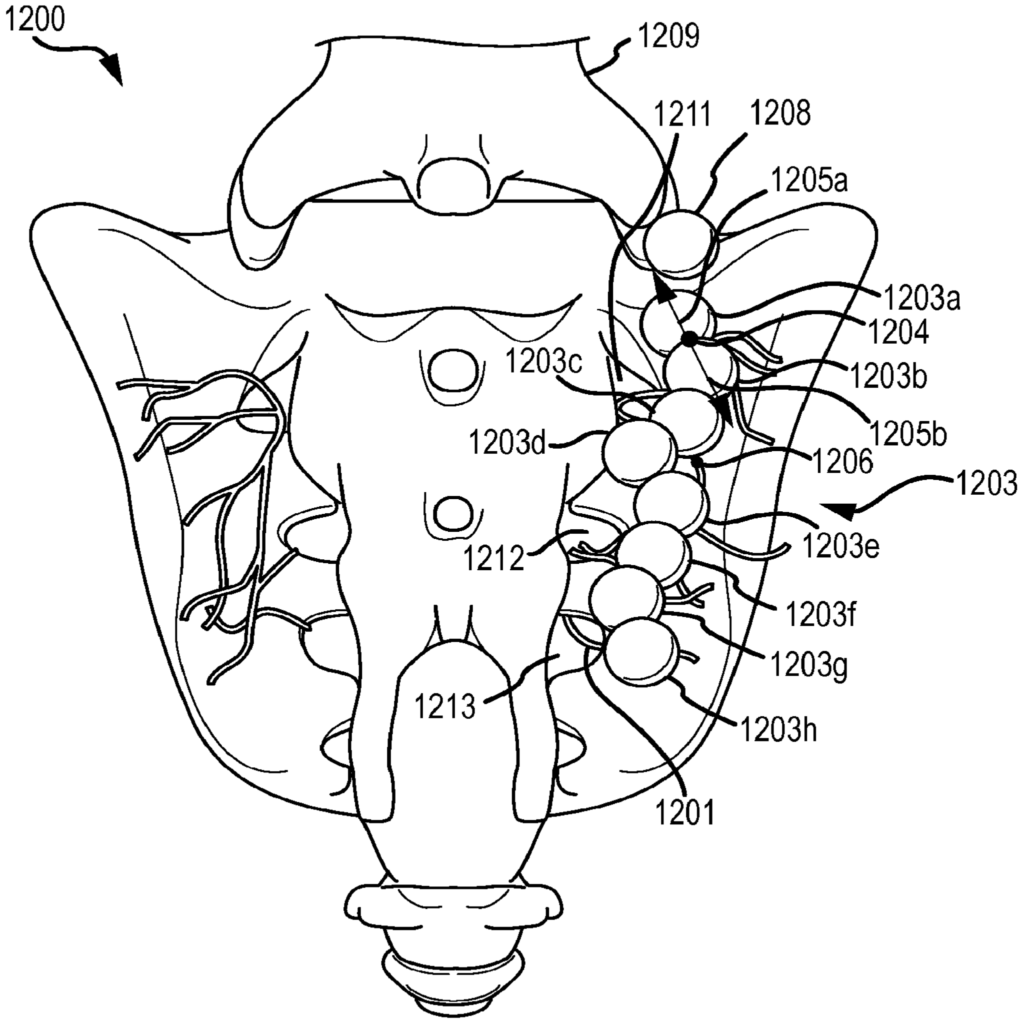
FIG. 13 is an illustration of a sacrum including target lesion volumes for performing Sacroiliac Joint (SIJ) RF neurotomy.
Figure 14:
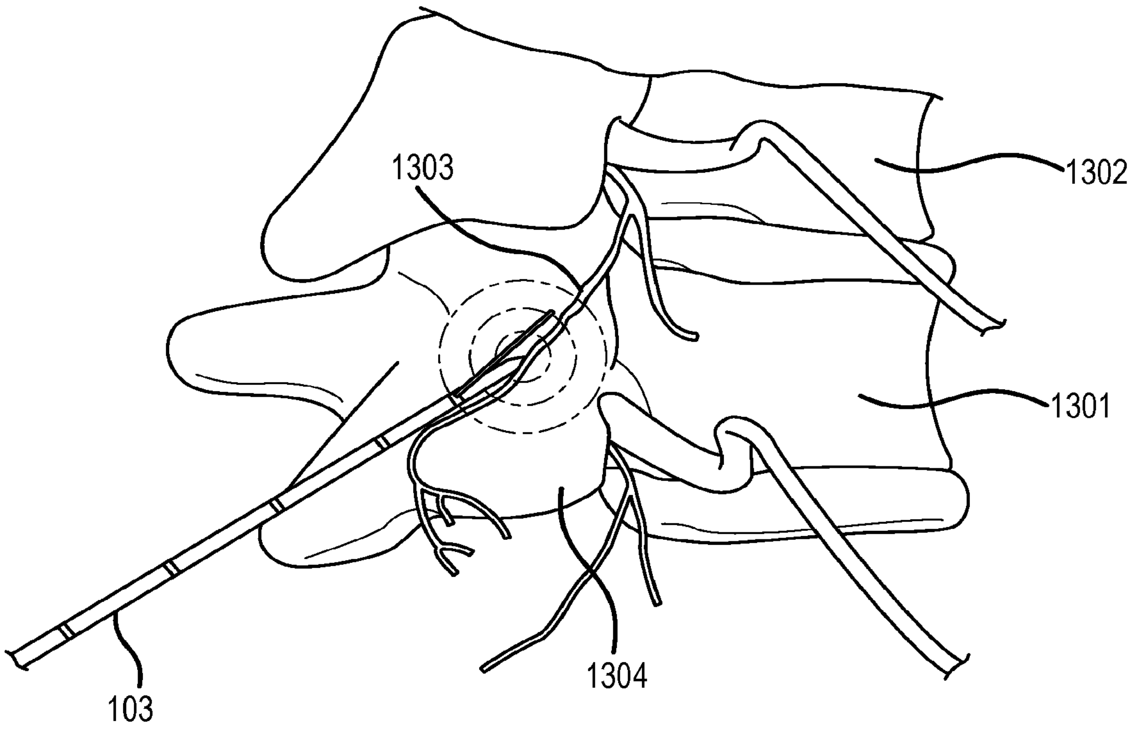
FIG. 14 is a perspective view of the needle of FIG. 2A positioned relative to a thoracic vertebra for performing RF neurotomy.

This process may include using a needle that enables the creation of lesions which are offset from the central longitudinal axis of the needle. The procedure will be described as being performed on the posterior rami 1201 of the SIJ referencing FIG. 13 and using the needle 103 of FIGS. 2A-6. It should be understood that other embodiments of needles described herein may be used in the procedure.

As part of the SIJ RF neurotomy process, it may be desirable to create a series of lesions in a series of lesion target volumes 1203*a*-1203*h* lateral to the sacral foramina 1211, 1212, 1213 of a side of the sacrum 1200 to ablate posterior rami 1201 that are responsible for relaying nociceptive signals from the SIJ. Since the exact positions of the rami 1201 may not be known, lesioning such a series of target volumes 1203*a*-1203*h* may accommodate the variations in rami 1201 positions. The series of target volumes 1203 may be in the form of one or more interconnected individual target volumes, such as target volumes 1203*a* and 1203*b*. In addition, the process may include an additional lesion 1208 between the L5 vertebra 1209 and the sacrum 1200.

The SIJ RF neurotomy process may include positioning the tip 201 of the needle 103 (e.g., using fluoroscopic navigation) such that it is in contact with, or proximate to, and in lateral relation to the S1 posterior sacral foraminal aperture (PSFA) 1211 at a first point 1204 that is at the intersection of the two target volumes 1203*a* and 1203*b*. Such positioning may be performed such that the needle 103 is oriented within 30° of being perpendicular to the sacrum 1200 at the point of contact (or at the point of the sacrum 1200 closest to the tip 201 of the needle 103). By contacting the sacrum 1200, a positive determination of the position of the needle 103 may be made. Optionally, from such a position, the needle 103 may be retracted a predetermined amount (e.g., between 3 mm and 5 mm) as measured by markers 224 on the needle 103, as determined using the collar about the elongated member 203 discussed above, and/or by fluoroscopic navigation. For example, a contralateral posterior oblique view may be obtained to ascertain that the tip 201 has not entered the spinal canal. For example, a fluoroscopic view may be obtained looking down the length of the needle 103 to verify that the needle 103 is properly offset from the S1 PSFA 1211 and/or a fluoroscopic view may be obtained looking perpendicular to the central longitudinal axis 223 of the needle 103 to verify that the needle is not below the surface of the scrum (e.g., disposed within the S1 PSFA 1211). Additionally, an electrical signal may be applied to the needle 103 to stimulate nerves proximate to the tip 201 to verify correct needle 103 placement.

The process may include rotating the needle 103 such that the midpoint 502 is oriented toward the first target volume 1203*a* in the direction of arrow 1205*a*. Next, the filaments 206*a*, 206*b* may be advanced to the deployed position. The position of the needle 103 and deployed filaments 206*a*, 206*b* may be verified using fluoroscopy and/or stimulation. The RF probe 401 may then be inserted into the lumen 222 such that RF energy emanating from the needle 103 will be conducted by the tip 201 and filaments 206*a*, 206*b* to the first target volume 1203*a*. Next, RF energy may be applied to the RF probe 401. The RF energy emanating from the needle 103 may be preferentially biased toward the first target volume 1203*a*. The lesion created by such an application of RF energy may, for example, have a maximum cross dimension of 8-10 mm, and may ablate a corresponding portion of the rami 1201.

Next, the filaments 206*a*, 206*b* may be retracted and the needle 103 may be rotated approximately 180 degrees such that the midpoint 502 is oriented toward the second target volume 1203*b* in the direction of arrow 1205*b*. Optionally, some lateral repositioning of the needle may performed (e.g. without any needle pull back or with a small amount of needle pull back and reinsertion). Next, the filaments 206*a*, 206*b* may be advanced to the deployed position. The position of the needle 103 and deployed filaments 206*a*, 206*b* may be verified using fluoroscopy and/or stimulation. Next, RF energy may be applied to the RF probe 401 to create a lesion corresponding to the second target volume 1203*b*.

In this regard, with a single insertion of the needle 103, two interconnected lesions (which may also be considered to be a single oblong lesion) may be created. Thus, as compared to known methods where an RF probe must be repositioned prior to each application of RF energy, the number of probe repositioning steps may be greatly reduced, thus reducing patient trauma and procedure duration. In this regard, a continuous region of lesioning may be achieved disposed about the S1 PSFA 1211 such that the lesion occupies a volume surrounding the S1 PSFA 1211 from about the 2:30 clock position to about the 5:30 clock position (as viewed in FIG. 13). Such lesioning may help to achieve denervation of the posterior rami proximate to the S1 PSFA 1211.

The above procedure may be repeated as appropriate to create lesions corresponding to the entire series of target volumes 1203*a*-1203*h*, thus denervating the SIJ. In this regard, a similar continuous region of lesioning may be achieved disposed about the S2 PSFA 1212 and a region of lesioning from about the 12:00 clock position to about the 3:00 clock position (as viewed in FIG. 13) relative to the S3 PSFA may be achieved disposed about the S3 PSFA 1213. Furthermore, a lesion 1208 may be created at the base of the superior articular process of the L5 1209 dorsal ramus in the grove between the superior articular process and the body of the sacrum. The needle 103 may be inserted generally perpendicular to the plane of FIG. 13 to produce lesion 1208.

In a variation of the above procedure, three or more lesions may be created with a needle in a single position. For example, a needle positioned at a point 1106 proximate to three target volumes 1203*c*, 1203*d*, and 1203*e*, may be operable to create lesions at each of the three target volumes 1203*c*, 1203*d*, and 1203*e*, thus further reducing the number of needle repositionings.

In another variation, each individual lesion corresponding to the series of target volumes 1203 may be created using a needle with deployable filaments where the needle is repositioned prior to each application of RF energy. In such a variation the sequence of steps may be insert needle, deploy filaments, apply RF energy, retract filaments, reposition needle, and repeat as appropriate to create each desired lesion. Such a procedure may be conducted using a needle capable of producing a lesion symmetric to a central longitudinal axis of the needle (e.g., the needle of FIG. 9).

3. Thoracic RF Neurotomy of a Medial Branch Nerve.

This process may include using a needle that enables the creation of lesions which are offset from the central longitudinal axis of the needle. Successful treatment of thoracic z-joint pain using radiofrequency ablation of relevant medial branch nerves is challenging owing to the inconsistent medial branch location in the intertransverse space, especially levels T5-T8. A conventional RF cannula must be positioned at multiple locations within the intertransverse space to achieve the sufficient tissue ablation for successful medial branch neurotomy. The procedure will be described as being performed on an intertransverse space between adjacent ones 1301, 1302 of the T5 to T8 thoracic vertebrae using FIG. 14 and the needle 103 of FIGS. 2A-6. It should be understood that other embodiments of needles described herein may be used in the procedure.

The process may include obtaining an optimized segmental anteroposterior image at target level defined by meticulous counting from T1 and T12. This may be followed by obtaining an image that is ipsilateral oblique 8-15 degrees off sagittal plane of the spine to visualize costotransverse joint lucency clearly. This allows improved visualization of superior-lateral transverse process (especially in osteopenic patients). This angle aids in directing the probe to a thoracic anatomic safe zone medial to the lung, minimizing risk of pneumothorax.

The skin entry site for the needle 103 may be over the most inferior aspect of transverse process slightly medial to costotransverse joint. Inserting the needle 103 may include navigating the device over transverse process over bone to touch superior transverse process slightly medial to costotransverse joint. The process may include checking antero-posterior imaging to demonstrate active tip 201 of the needle 103 is at the superolateral corner of the transverse process. The process may also include checking a contralateral oblique (e.g., +/−15 degrees) image view to demonstrate the target transverse process in an elongate fashion. This view is useful for demonstrating the tip 201 of the needle 103 in relationship to the superolateral margin of the transverse process subadjacent to the targeted medial branch nerve. The process may include retracting the active tip 201 slightly (e.g., 1 mm to 3 mm).

The process may include rotating the needle 103 such that the midpoint 502 is oriented toward the intertransverse space between the vertebrae 1301, 1302 and the medial branch nerve 1303 that is positioned therein. Next, the filaments 206*a*, 206*b* may be advanced ventral into the intertransverse space between the vertebrae 1301, 1302 to the deployed position. The position of the needle 103 and deployed filaments 206*a*, 206*b* may be verified using fluoroscopy (e.g., using lateral imaging). The RF probe 401 may then be inserted into the lumen 222 such that RF energy emanating from the probe 103 will be conducted by the tip 201 and filaments 206*a*, 206*b* to the target medial branch nerve 1303. Stimulation (e.g., motor and/or sensory) may be performed to verify positioning. Next, RF energy may be applied to the RF probe 401. The RF energy emanating from the needle 103 may be preferentially biased toward the volume between the vertebrae 1301, 1302. The lesion created by such a procedure may, for example, have a maximum cross dimension of 8-10 mm, and may ablate a corresponding portion of the medial branch nerve 1303.

It is noted that thoracic RF neurotomy performed on other thoracic vertebrae may require different sized lesions. For example, thoracic RF neurotomy performed on the T3-T4 vertebrae may require a smaller lesion volume than the above-described procedure, and thoracic RF neurotomy performed on the T1-T2 vertebrae may require a still smaller lesion volume. As described herein, the deployment of the filaments of the needle 103 may be varied to achieve such desired target lesion volumes.

4. Cervical Medial Branch RF Neurotomy.

Embodiments of needles described herein (e.g., the needle 103 of FIG. 2A) are capable of creating a volume of tissue ablation necessary for complete denervation of the cervical zygapophyseal joints, including the C2/3 cervical zygapophyseal joint (z-joint). Tissue ablation for cervical z-joint using embodiments of needles described herein may be accomplished using a single placement and single heating cycle. Such single placement and single heating cycle may avoid unnecessary tissue damage from multiple placements of a conventional probe, and unintended injury to collateral tissue caused by excessive lesioning. The zone of ablation created by various embodiments of the device is designed to provide sufficient, and necessary tissue coagulation for a successful procedure, and thus may be expected to improve the outcomes of patients undergoing this spinal radiofrequency neurotomy.

Figure 15:
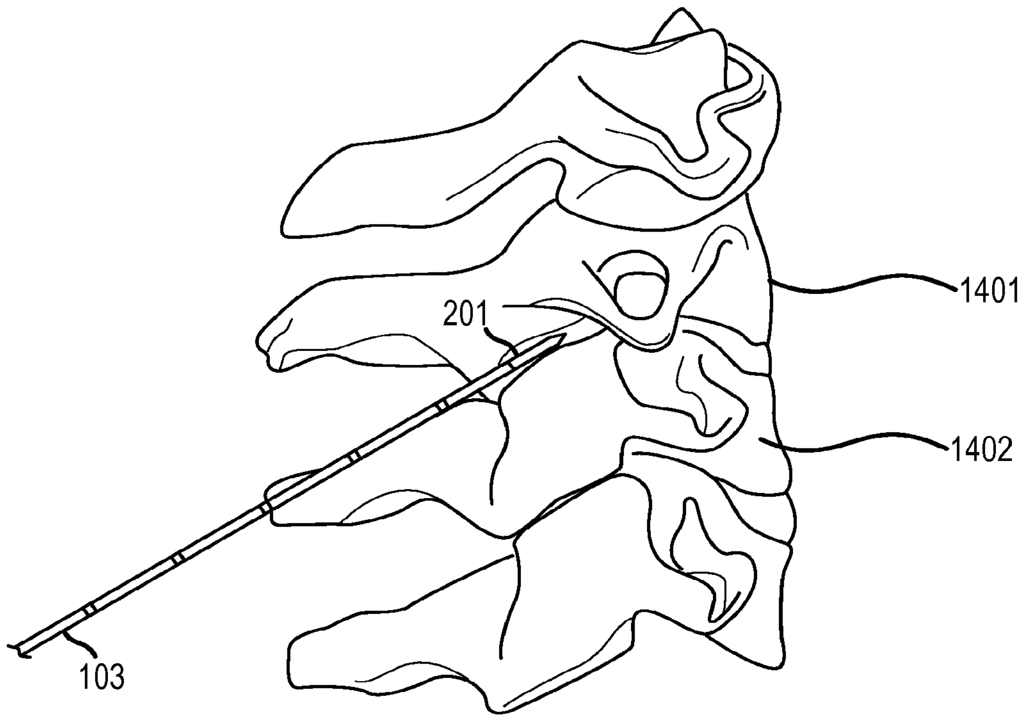
FIG. 15 is a perspective view of the needle of FIG. 2A positioned relative to the C2/3 cervical zygapophyseal joint (z joint) for performing cervical medial branch RF neurotomy on the third occipital nerve.

A cervical medial branch RF neurotomy procedure will be described as being performed on the third occipital nerve at the C2/3 z-joint using the needle 103 as shown in FIG. 15. In FIG. 15, the needle 103 is positioned between the C2 1401 and C3 1402 vertebrae.

In a first step, the patient may be placed in a prone position on a radiolucent table suited to performing fluoroscopically guided spinal procedures. Sedation may be administered. The patient's head may be rotated away from the targeted side. Sterile skin prep and draping may be performed using standard well-described surgical techniques.

For Third Occipital Nerve (TON) ablation (C2/3 joint innervation) the lateral aspect of the C2/3 Z-joint is located under either parasagittal or alternatively, ipsilateral oblique rotation of less than/equal to 30 degrees of obliquity relative to the true sagittal plane of the cervical spine. The skin entry point may be infiltrated with local anesthetic. Then the tip 201 of the needle 103 is moved over the most lateral aspect of bone of the articular pillar at the juncture of the C2/3 z-joint to a first position contacting bone proximate to the most posterior and lateral aspect of the z-joint complex Once boney contact is made, the needle 103 may be retracted a predetermined distance (e.g., 1-3 mm) and the filaments are deployed towards the lateral aspect of the C2/3 z-joint. The needle 103 may be rotated about a central longitudinal axis prior to filament deployment to ensure that deployment will occur in the desired direction.

Multiplanar fluoroscopic imaging may then be employed to verify that the tip and filaments are positioned as desired. For example, it may be verified that the filaments are positioned straddling the lateral joint lucency, and posterior to the C2/3 neural foramen. Useful imaging angles include anterior-posterior (AP), lateral, and contralateral oblique (Sluijter) views. To further verify adequate positioning of the needle 103, motor stimulation may be performed by delivering a voltage (of up to 2 volts) at 2 Hz to the tip 201 and filaments. Furthermore, sensory stimulation may be performed at appropriate voltage (e.g., 0.4 to 1 volt) and frequency (e.g., 50 Hz).

After position verification, RF energy may be applied to the tip and the plurality of filaments to generate heat that ablates a portion of the third occipital nerve. After lesioning, the device may be removed. For levels below the C2/3 z-joint, the procedure may be similar than as described above with respect to the third occipital nerve, with the exception that the initial boney contact target is at the waist of inflection point of the articular pillar.

Similar to the above procedures, other spinal RF procedures may benefit from the asymmetrical application of RF energy from embodiments of probes described herein. Such asymmetry may, for example, be used to project RF energy in a desired direction and/or limit the projection of RF energy in undesired directions. The configuration of the filaments may be selected for a particular application to produce a desired size, shape and location (relative to the needle tip) of a lesion within the patient. The location of the lesion may be offset distally and/or laterally from the tip of the needle as required for a particular application.

It will be appreciated that the delivery of RF energy to tissue in the anatomy is practiced for a multitude of reasons and embodiments of needles described herein may be adapted (modified or scaled) for use in other medical procedures. For example, embodiments of needles described herein could be used to deliver RF energy as a means to cauterize "feeder vessels," such as in bleeding ulcers and/or in orthopedic applications. Further, embodiments of needles described herein could also be adapted to procedures such as cardiac ablation, in which cardiac tissue is destroyed in an effort to restore a normal electrical rhythm in the hart. This application could further benefit from the ability of embodiments of needles described herein to deliver fluid through a lumen since, for example, emerging procedures in cardiac therapy require the ability to deliver stem cells, vascular endothelial growth factor (VEGF), or other growth factors to cardiac tissue. The ability to steer embodiments of the needle (previously discussed) may provide significant benefit to the in the field of cardiovascular drug delivery.

While various embodiments of the present invention have been described in detail, it is apparent that further modifications and adaptations of the invention will occur to those skilled in the art. However, it is to be expressly understood that such modifications and adaptations are within the spirit and scope of the present invention.

What is claimed is:

1. A radiofrequency neurotomy system comprising:
 a radiofrequency probe assembly that comprises;
  a radiofrequency probe that comprises a temperature sensor operable to measure temperature at a distal end of the radiofrequency probe; and
  a cable; and
 a radiofrequency neurotomy needle that comprises:
  a first hub;
  an elongate member fixedly attached to the first hub, the elongate member comprising a tube that is 16 gauge or smaller and a lumen within the tube, wherein a central longitudinal axis is disposed along a center of the elongate member;
  a tip at a distal end of the elongate member shaped to pierce tissue of a patient;
  an additional tube that is conductive, a portion of the additional tube being housed in the lumen of the elongate member;
  a plurality of filaments movable between a retracted position and a deployed position;
  a second hub interconnected to the plurality of filaments; and
  an actuator interconnected to the second hub and to the plurality of filaments, wherein rotation of the actuator relative to the first hub in a first direction causes the second hub to move axially to advance the plurality of filaments to the deployed position and rotation of the actuator relative to the first hub in a second direction that is opposite the first direction causes the second hub to move axially to retract the plurality of filaments to the retracted position,
 wherein:
  the radiofrequency probe is insertable into the additional tube that is in the lumen of the elongate member;
  the plurality of filaments are advanceable to the deployed position without concurrent advancement of the radiofrequency probe relative to the lumen; and
  when the radiofrequency probe is inserted into the additional tube and is interconnected to a radiofrequency generator via the cable, the radiofrequency probe is configured to transmit radiofrequency energy applied thereto that energizes the additional tube, and the plurality of filaments and the tip are configured to conduct and emanate the radiofrequency energy such that the radiofrequency probe, the tip, and the plurality of filaments form a single radiofrequency electrode.

2. The radiofrequency neurotomy system of claim 1, wherein the radiofrequency probe is integrated into the needle.

3. The radiofrequency neurotomy system of claim 2, wherein a distal end of the radiofrequency probe is near the tip when the plurality of filaments and the tip conduct and emanate the radiofrequency energy.

4. The radiofrequency neurotomy system of claim 1, wherein the additional tube physically contacts the tip.

5. The radiofrequency neurotomy system of claim 1, wherein a distal end of the radiofrequency probe is near the tip when the plurality of filaments and the tip conduct and emanate the radiofrequency energy.

6. The radiofrequency neurotomy system of claim 1, wherein the radiofrequency probe is configured to be inserted into the additional tube during use of the radiofrequency neurotomy needle in the patient, and wherein the radiofrequency probe extends through the first hub when inserted into the additional tube.

7. The radiofrequency neurotomy system of claim 1, wherein:
 the radiofrequency neurotomy system further comprises a projection;
 the actuator comprises a helical track sized to accommodate the projection; and
 as the actuator is rotated relative to the first hub, the helical track and the projection, in combination, cause the second hub to move axially.

8. The radiofrequency neurotomy system of claim 7, wherein rotational motion of the actuator relative to the first hub is not transmitted to the second hub.

9. The radiofrequency neurotomy system of claim 1, wherein each filament of the plurality of filaments comprises a distal end that defines a point, and wherein an average of all points of the plurality of filaments is offset from the central longitudinal axis of the elongate member when the plurality of filaments are in the deployed position.

10. The radiofrequency neurotomy system of claim 1, wherein the plurality of filaments are at least partially disposed within the elongate member when in the retracted position.

11. The radiofrequency neurotomy system of claim 10, wherein distal tips of the plurality of filaments extend distally beyond a distal point of the tip when the plurality of filaments are in the deployed position.

12. The radiofrequency neurotomy system of claim 1, wherein a single member runs along at least part of the elongate member and the plurality of filaments are interconnected to the single member.

13. The radiofrequency neurotomy system of claim 12, wherein the plurality of filaments are interconnected to the single member at a position proximal to the tip.

14. The radiofrequency neurotomy system of claim 1, wherein the plurality of filaments exit from the tip at a common location and form a fan-like arrangement as they are deployed.

15. The radiofrequency neurotomy system of claim 1, wherein the plurality of filaments are configured to achieve a lesion having a pyramidal shape when in the deployed position within the patient.

16. The radiofrequency neurotomy system of claim 1, wherein the elongate member and the tip are a single unitary structure.

17. The radiofrequency neurotomy system of claim 1, wherein the radiofrequency probe, the plurality of filaments, and the tip form a monopolar electrode.

18. The radiofrequency neurotomy system of claim 1, wherein the plurality of filaments comprise a shape memory alloy, and wherein a pre-set bias is present in the plurality of filaments such that the plurality of filaments are curved when in the deployed position.

19. The radiofrequency neurotomy system of claim 1, wherein the temperature sensor of the radiofrequency probe assembly comprises a thermocouple.

20. The radiofrequency neurotomy system of claim 1, wherein the radiofrequency probe is insertable into the additional tube after the plurality of filaments have been advanced to the deployed position.

21. The radiofrequency neurotomy system of claim 1, wherein:

the radiofrequency probe extends through the first hub when the radiofrequency probe is inserted into the additional tube;

the radiofrequency neurotomy needle further comprises a projection and the actuator comprises a helical track sized to accommodate the projection;

as the actuator is rotated relative to the first hub, the helical track and the projection, in combination, cause the second hub to move axially;

rotational motion of the actuator relative to the first hub is not transmitted to the second hub;

each filament of the plurality of filaments comprises a distal end that defines a point, and an average of all points of the plurality of filaments is offset from the central longitudinal axis of the elongate member when the plurality of filaments are in the deployed position;

the plurality of filaments are at least partially disposed within the elongate member when in the retracted position;

the plurality of filaments are configured to achieve a lesion having a pyramidal shape when in the deployed position within the patient;

the plurality of filaments comprise a shape memory alloy; and a pre-set bias is present in the plurality of filaments such that the plurality of filaments are curved when in the deployed position.

22. The radiofrequency neurotomy system of claim 21, wherein a distal end of the radiofrequency probe is near the tip when the plurality of filaments and the tip conduct and emanate the radiofrequency energy.

23. The radiofrequency neurotomy system of claim 22, wherein distal tips of the plurality of filaments extend distally beyond a distal point of the tip when the plurality of filaments are in the deployed position, and wherein when the radiofrequency neurotomy needle is placed generally perpendicular to a surface of a bone of the patient and the deployed filaments are proximate to the surface, the radiofrequency neurotomy needle is configured to achieve a lesion width along the surface that is wider than what the radiofrequency neurotomy needle would create if the plurality of filaments were not deployed.

24. The radiofrequency neurotomy system of claim 23, wherein the tube of the elongate member is 18 gauge.

25. The radiofrequency neurotomy system of claim 23, wherein a single member runs along at least part of the elongate member and the plurality of filaments are interconnected to the single member at a position proximal to the tip.

26. The radiofrequency neurotomy system of claim 5, wherein the plurality of filaments exit from the tip at a common location and form a fan-like arrangement as they are deployed.

27. The radiofrequency neurotomy system of claim 23, wherein the radiofrequency probe, the plurality of filaments, and the tip form a monopolar electrode.

28. The radiofrequency neurotomy system of claim 23, wherein the radiofrequency probe is integrated into the needle.

29. The radiofrequency neurotomy system of claim 23, wherein the radiofrequency probe is insertable into the additional tube after the plurality of filaments have been advanced to the deployed position within the patient.

30. The radiofrequency neurotomy system of claim 1, wherein the elongate member is 18 gauge.

31. The radiofrequency neurotomy system of claim 1, wherein the radiofrequency neurotomy needle is sized for use in spinal radiofrequency neurotomy.

32. The radiofrequency neurotomy system of claim 1, wherein when the radiofrequency neurotomy needle is placed generally perpendicular to a surface of a bone of the patient and the deployed filaments are proximate to the surface, the radiofrequency neurotomy needle is configured to achieve a lesion width along the surface that is wider than what the radiofrequency neurotomy needle would create if the plurality of filaments were not deployed.

33. The radiofrequency neurotomy system of claim 11, wherein when the radiofrequency neurotomy needle is placed generally perpendicular to a surface of a bone of the patient and the deployed filaments are proximate to the surface, the radiofrequency neurotomy needle is configured to achieve a lesion width along the surface that is wider than what the radiofrequency neurotomy needle would create if the plurality of filaments were not deployed.

34. The radiofrequency neurotomy system of claim 1, wherein the number of filaments is three.

35. The radiofrequency neurotomy system of claim 34, wherein tips of the three filaments form a polygon that has a centroid when the three filaments are in the deployed position, and wherein the centroid is offset from the central longitudinal axis such that the three filaments are configured to produce a lesion that is offset from the central longitudinal axis.

36. The radiofrequency neurotomy system of claim 1, wherein adjacent filaments are positioned about 120 degrees apart from each other about the central longitudinal axis.

37. The radiofrequency neurotomy system of claim 1, wherein each of the plurality of filaments is curved away from the central longitudinal axis when in the deployed position.

38. The radiofrequency neurotomy system of claim 1, wherein the additional tube comprises an additional lumen that is configured to transport fluid from a fluid source and is configured to subsequently accept the radiofrequency probe therein.

39. The radiofrequency neurotomy system of claim 38, where a maximum cross-dimension of the additional lumen is less than about 0.85 millimeters.

* * * * *